United States Patent
Diem et al.

(10) Patent No.: US 10,611,823 B2
(45) Date of Patent: Apr. 7, 2020

(54) CD137 BINDING FIBRONECTIN TYPE III DOMAINS

(71) Applicant: Janssen Biotech, Inc., Horsham, PA (US)

(72) Inventors: Michael Diem, Havertown, PA (US); Rebecca Hawkins, Harleysville, PA (US); Steven Jacobs, North Wales, PA (US); Manuel Sepulveda, Princeton Junction, NJ (US)

(73) Assignee: HANSSEN BIOTECH, INC, Horsham, PA (US)

( * ) Notice: Subject to any disclaimer, the term of this patent is extended or adjusted under 35 U.S.C. 154(b) by 93 days.

(21) Appl. No.: 15/840,303

(22) Filed: Dec. 13, 2017

(65) Prior Publication Data

US 2018/0162929 A1 Jun. 14, 2018

Related U.S. Application Data

(60) Provisional application No. 62/434,064, filed on Dec. 14, 2016.

(51) Int. Cl.

| | |
|---|---|
| C07K 14/78 | (2006.01) |
| G01N 33/53 | (2006.01) |
| G01N 33/574 | (2006.01) |
| G01N 33/566 | (2006.01) |
| C07K 14/705 | (2006.01) |
| A61P 35/00 | (2006.01) |
| C12N 15/85 | (2006.01) |
| G01N 33/68 | (2006.01) |
| C07K 14/71 | (2006.01) |
| C07K 19/00 | (2006.01) |
| A61K 38/39 | (2006.01) |

(52) U.S. Cl.
CPC .............. *C07K 14/78* (2013.01); *A61P 35/00* (2018.01); *C07K 14/705* (2013.01); *C07K 14/70596* (2013.01); *C12N 15/85* (2013.01); *G01N 33/53* (2013.01); *G01N 33/574* (2013.01); *G01N 33/57492* (2013.01); *G01N 33/6893* (2013.01); *A61K 38/39* (2013.01); *C07K 2319/31* (2013.01); *C07K 2319/40* (2013.01)

(58) Field of Classification Search
CPC ............ C07K 14/705; C07K 14/70596; C07K 14/47; C07K 14/78; C07K 2319/00; C07K 2319/31; A61K 38/17; A61K 38/39
See application file for complete search history.

(56) References Cited

U.S. PATENT DOCUMENTS 7,288,638 B2 10/2007 Jure-Kunkel et al.

OTHER PUBLICATIONS

Diem et al. Selection of high-affinity Centyrin FN3 domains from a simply library diversified at a combination of strand and loop positions. Protein Engin Design Selection 27(10): 419-429, 2014.*
Jacobs et al. Design of novel FN3 domains with high stability by a consensus sequence approach. Protein Engineer Design Selection 25(3): 107-117, 2012.*
Cooper et al., "4-1BB (CD137) controls the clonal expansion and survival of CD8 T cells in vivo but does not contribute the development of cytotoxicity", Eur. J. Immunol., vol. 32, pp. 521-529, 2002.
Odegrip et al., "CIS display: In vitro selection of peptides from libraries of protein-DNA complexes," Proceedings of the National Academy of Science USA, vol. 101, No. 9, pp. 2806-2810 (2004).
Gramaglia et al., "Co-stimulation of antigen-specific CD4 T cells by 4-1BB ligand," Eur. J. Immunol., vol. 30, pp. 392-402 (2000).
DeBenedette et al., "Role of 4-1BB Ligand in Costimulation of T Lymphocyte Growth and its Upregulation on M12 B Lymphomas by cAMP," J. Exp. Med., vol. 181, pp. 985-992 (1995).
Langstein et al., "CD137 Induces Proliferation and Endomitosis in Monocytes," Blood, vol. 94, No. 9, pp. 3161-3168 (1999).
Langstein et al., "CD137 (ILA/4-1BB), a Member of the TNF Receptor Family, Induces Monocyte Activation via Bidirectional Signaling," The Journal of Immunology, vol. 160, pp. 2488-2494 (1998).
Lee et al., "4-1BB Promotes the Survival of CD8+ T Lymphocytes by Increasing Expression of Bcl-xL and Bfl-11," The Journal of Immunol., vol. 169, pp. 4882-4888 (2002).
Michel et al., "A soluble form of CD137 (ILA/4-1BB), a member of the TNF receptor family, is released by activated lymphocytes and is detectable in sera of patients with rheumatoid arthritis," Eur. J. Immunol., vol. 28, pp. 290-295 (1998).
Michel et al., "CD137-induced apoptosis is independent of CD95," Immunology, vol. 98, pp. 42-46 (1999).
Schwarz et al., "ILA, a Member of the Human Nerve Growth Factor/Tumor Necrosis Factor Receptor Family, Regulates T-Lymphocyte Proliferation and Survival," Blood, vol. 87, No. 7, pp. 2839-2845 (Apr. 1, 1996).
Shuford et al., "4-1BB Costimulatory Signals Preferentially Induce CD8+ T Cell Proliferation and Lead to the Amplification In Vivo of Cytotoxic T Cell Responses," J. Exp. Med., vol. 186, No. 1, pp. 47-55 (Jul. 7, 1997).
Takahashi et al., "Cutting Edge: 4-1BB Is a Bona Fide CD8 T Cell Survival Signal," J Immunol., vol. 162, pp. 5037-5040 (1999).
Alderson et al., "Molecular and Biological Characterization of Human 4-1BB and its Ligand", Eur. J. Immunol., vol. 24, pp. 2219-2227, 1994.
Hurtado et al., "Potential role of 4-1BB in T cell Activation Comparison with the Costimulatory Molecule CD28", Journal of Immunology, vol. 155, pp. 3360-3367, 1995.
Hurtado et al., "Signals through 4-1BB are Costimulatory to previously activated splenic T cells and inhibit activation-induced cell death", Journal of Immunology, vol. 158, pp. 2600-2609, 1997.
Maus et al., "Ex vivo expansion of polyclonal and antigen-specific cytotoxic T lymphocytes by artificial APCs expressing ligands for the T-cell receptor, CD28 and 4-1BB", Nature Biotechnology, vol. 20, pp. 143-148, Feb. 2002.

(Continued)

*Primary Examiner* — Bridget E Bunner
(74) *Attorney, Agent, or Firm* — Pepper Hamilton LLP

(57) ABSTRACT

FN3 domains that specifically bind to CD137, their conjugates, isolated nucleotides encoding the molecules, vectors, host cells, and methods of making and using them are useful in therapeutic and diagnostic applications.

11 Claims, No Drawings

Specification includes a Sequence Listing.

(56) References Cited

OTHER PUBLICATIONS

Michel et al., "Expression of soluble CD137 correlates with activation-induced cell death of lymphocytes", Cytokine, vol. 12, No. 6, pp. 742-746, 2000.
Zhou et al., "Characterization of human homologue of 4-1BB and its ligand", Immunology Letters, vol. 45, pp. 67-73, 1995.
Pauly et al., "CD137 is expressed by follicular dendritic cells and costimulates B lymphocyte activation in germinal centers", Journal of Leukocyte Biology, vol. 72, pp. 35-42, Jul. 2002.
Langstein et al., "Identification of CD137 as a potent monocyte survival factor", Journal of Leukocyte Biology, vol. 65, pp. 829-833, Jun. 1999.
Kwon et al., "cDNA sequences of two inducible T-cell genes", Proc. Natl. Acad. Sci., vol. 86, pp. 1963-1967, Mar. 1989.

\* cited by examiner

CD137 BINDING FIBRONECTIN TYPE III DOMAINS

CROSS REFERENCE TO RELATED APPLICATIONS

This application claims the benefit of U.S. Provisional Application Ser. No. 62/434,064, filed 14 Dec. 2016. The entire contents of the aforementioned application are incorporated herein by reference in their entireties.

FIELD OF THE INVENTION

The present invention relates to fibronectin type III domains that specifically bind to cluster of differentiation 137 (CD137) and methods of making and using the molecules.

BACKGROUND OF THE INVENTION

Advances in understanding of the requirements for tumor antigen recognition and immune effector function indicate that a potential strategy to enhance an anti-tumor immune response is to provide co-stimulation through an auxiliary molecule. The current model for T-cell activation postulates that naive T-cells require two signals for full activation: (i) a signal provided through the binding of processed antigens presented to the T-cell receptor by major histocompatibility complex (MHC) class I molecules; and (ii) an additional signal provided by the interaction of co-stimulatory molecules on the surface of T-cells and their ligands on antigen presenting cells.

CD137 (4-1BB) is a member of the TNF receptor superfamily and is an activation-induced T-cell costimulatory molecule. The receptor was initially described in mice (B. Kwon et al., *P.N.A.S.* USA, 86:1963-7 (1989)), and later identified in humans (M. Alderson et al., *Eur. J. Immunol.*, 24: 2219-27 (1994); Z. Zhou et al., *Immunol. Lett.*, 45:67 (1995)). The interaction of CD137 and the CD137 ligand (4-1BBL) activates an important costimulatory pathway. Signaling via CD137 upregulates survival genes, enhances cell division, induces cytokine production, and prevents activation-induced cell death in T cells. The importance of the CD137 pathway has been underscored in a number of diseases, including cancer (see, e.g., U.S. Pat. No. 7,288,638).

Expression of CD137 has been shown to be predominantly on cells of lymphoid lineage such as activated T-cells, activated Natural Killer (NK) cells, NKT-cells, CD4CD25 regulatory T-cells, and also on activated thymocytes, and intraepithelial lymphocytes. In addition, CD137 has also been shown to be expressed on cells of myeloid origin like dendritic cells, monocytes, neutrophils, and eosinophils. Even though CD137 expression is mainly restricted to immune/inflammatory cells, there have been reports describing its expression on endothelial cells associated with a small number of tissues from inflammatory sites and tumors.

The physiological events observed following CD137 stimulation on T-cells are mediated by NF-κB and PI3K/ERK1/2 signals with separate physiological functions. NF-κB signals trigger expression of Bcl-XL, an anti-apoptotic molecule, thus resulting in increased survival, whereas PI3K and ERK1/2 signals are specifically responsible for CD137-mediated cell cycle progression (H. Lee et al., *J. Immunol.*, 169(9):4882-8 (2002)). The effect of CD137 activation on the inhibition of activation-induced cell death was shown in vitro by Hurtado et al. (J. Hurtado et al., *J. Immunol.*, 158(6):2600-9 (1997)), and in an in vivo system in which anti-CD137 monoclonal antibodies (mabs) were shown to produce long-term survival of superantigen-activated CD8+ T-cells by preventing clonal deletion (C. Takahashi et al., *J. Immunol.*, 162:5037 (1999)). Later, two reports demonstrated, under different experimental conditions, that the CD137 signal regulated both clonal expansion and survival of CD8+ T-cells (D. Cooper et al., *Eur. J. Immunol.*, 32(2):521-9 (2002); M. Maus et al., *Nat. Biotechnol.*, 20:143 (2002)).

Altogether, CD137 stimulation results in enhanced expansion, survival, and effector functions of newly primed CD8+ T-cells, acting, in part, directly on these cells. Both CD4+ and CD8+ T-cells have been shown to respond to CD137 stimulation, however, it appears that enhancement of T-cell function is greater in CD8+ cells ((W. Shuford et al., *J. Exp. Med.*, 186(1):47-55 (1997); I. Gramaglia et al., *Eur. J. Immunol.*, 30(2):392-402 (2000); C. Takahashi et al., *J. Immunol.*, 162:5037 (1999)). Based on the critical role of CD137 stimulation in CD8+ T-cell function and survival, agonism of the CD137/CD137L system provides a plausible approach for the treatment of tumors and viral pathogens.

Alternatively, while it has been shown that agonistic antibodies to CD137 and the ligand to CD137 enhance lymphocyte activation, the CD137 protein has the opposite effect. It inhibits proliferation of activated T lymphocytes and induces programmed cell death. These T cell-inhibitory activities of CD137 require immobilisation of the protein, arguing for transmission of a signal through the ligand/coreceptor (Schwarz et al., *Blood* 87, 2839-2845 (1996); Michel et al., *Immunology* 98, 42-46 (1999)).

The known human CD137 ligand is expressed constitutively by monocytes and its expression is inducible in T lymphocytes (Alderson et al., *Eur. J. Immunol.* 24, 2219-2227 (1994)). Monocytes are activated by immobilised CD137 protein and their survival is profoundly prolonged by CD137. (Langstein et al., *J. Immunol.* 160, 2488-2494 (1998); Langstein et al., *J. Leuk. Biol.* 65, 829-833 (1999)). CD137 also induces proliferation in peripheral monocytes (Langstein et al., 1999b). Macrophage colony-stimulating factor (M-CSF) is essential for the proliferative and survival-enhancing activities of CD137 (Langstein et al., *J. Leuk. Biol.* 65, 829-833 (1999); Langstein et al., *Blood* 94, 3161-3168 (1999)).

Signalling through CD137 ligand has also been demonstrated in B cells where it enhances proliferation and immunoglobulin synthesis. This occurs at interactions of B cells with CD137-expressing T cells or follicular dendritic cells (Pauly et al., *J. Leuk. Biol.* 72, 35-42 (2002)). It was postulated that similarly to the CD40 receptor/ligand system, which mediates T cell help to B cells after first antigen encounter, the CD137 receptor/ligand system may mediate co-stimulation of B cells by FDC during affinity maturation (Pauly et al., *J. Leuk. Biol.* 72, 35-42 (2002)).

Furthermore, soluble forms of CD137 are generated by differential splicing and are selectively expressed by activated T cells (Michel et al., *Eur. J. Immunol.* 28, 290-295 (1998)). Soluble CD137 is antagonistic to membrane-bound or immobilised CD137, and levels of soluble CD137 correlate with activation induced cell death in T cells (DeBenedette et al., *J. Exp. Med.* 181, 985-992 (1995); Hurtado et al., *J. Immunol.* 155, 3360-3367 (1995); Michel et al., *Cytokine* 12, 742-746 (2000)).

Thus, considering the complicated picture for CD137 involvement in divergent mechanisms of action and different cell types, there exists a need for reagents to accurately detect CD137 in tumor tissues and other samples and for new therapeutics that modulate the interaction between CD137 and the 4-1BBL ligand or that modulate the interaction between CD137 and other cellular targets.

SUMMARY OF THE INVENTION

The invention provides an isolated FN3 domain that specifically binds to CD137 protein.

The invention also provides an isolated FN3 domain that specifically binds to CD137 protein comprising the amino acid sequence of SEQ ID NOs: 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, or 224.

The invention also provides an isolated polynucleotide encoding the FN3 domain that specifically binds to CD137 protein.

The invention also provides a vector comprising the polynucleotide.

The invention also provides a host cell comprising the vector.

The invention also provides a method of producing the FN3 domain that specifically binds to CD137 protein, comprising culturing the isolated host cell under conditions that the FN3 domain that specifically binds to CD137 protein is expressed, and purifying the FN3 domain that specifically binds to CD137 protein.

The invention also provides a pharmaceutical composition comprising the FN3 domain that specifically binds to CD137 protein and a pharmaceutically acceptable carrier.

The invention also provides an anti-idiotypic antibody that specifically binds the FN3 domain that specifically binds to CD137 protein.

The invention also provides a kit comprising the FN3 domain.

The invention also provides a method of detecting CD137-expressing cancer cells in a tumor tissue, comprising
obtaining a sample of the tumor tissue from a subject; and
detecting whether CD137 protein is expressed in the tumor tissue by contacting the sample of the tumor tissue with the FN3 domain that specifically binds CD137 protein comprising the amino acid sequence of one of SEQ ID NOs: 45-224 and detecting the binding between CD137 protein and the FN3 domain.

The invention also provides a method of isolating CD137 expressing cells, comprising obtaining a sample from a subject;
contacting the sample with the FN3 domain that specifically binds to CD137 protein comprising the amino acid sequence of one of SEQ ID NOs: 45-224, and
isolating the cells bound to the FN3 domains.

The invention also provides a method of detecting CD137-expressing cancer cells in a tumor tissue, comprising
conjugating the FN3 domain that specifically binds to CD137 protein comprising the amino acid sequence of one of SEQ ID NOs: 45-224 to a detectable label to form a conjugate;
administering the conjugate to a subject; and
visualizing the CD137 expressing cancer cells to which the conjugate is bound.

DETAILED DESCRIPTION OF THE INVENTION

As used in this specification and the appended claims, the singular forms "a," "an," and "the" include plural referents unless the content clearly dictates otherwise. Thus, for example, reference to "a cell" includes a combination of two or more cells, and the like.

"Fibronectin type III (FN3) domain" (FN3 domain) refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the 3rd FN3 domain of tenascin (TN3), or the 10th FN3 domain of fibronectin (FN10).

"Centyrin" refers to a FN3 domain that is based on the consensus sequence of the 15 different FN3 domains present in human tenascin C.

The term "capture agent" refers to substances that bind to a particular type of cells and enable the isolation of that cell from other cells. Exemplary capture agents are magnetic beads, ferrofluids, encapsulating reagents, molecules that bind the particular cell type and the like.

"Sample" refers to a collection of similar fluids, cells, or tissues isolated from a subject, as well as fluids, cells, or tissues present within a subject. Exemplary samples are tissue biopsies, fine needle aspirations, surgically resected tissue, organ cultures, cell cultures and biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium and lavage fluids and the like.

"Substituting" or "substituted" or 'mutating" or "mutated" refers to altering, deleting of inserting one or more amino acids or nucleotides in a polypeptide or polynucleotide sequence to generate a variant of that sequence.

"Variant" refers to a polypeptide or a polynucleotide that differs from a reference polypeptide or a reference polynucleotide by one or more modifications for example, substitutions, insertions or deletions.

"Specifically binds" or "specific binding" refers to the ability of the FN3 domain of the invention to bind CD137 with a dissociation constant ($K_D$) of about $1 \times 10^{-6}$ M or less, for example about $1 \times 10^{-7}$ M or less, about $1 \times 10^{-8}$ M or less, about $1 \times 10^{-9}$ M or less, about $1 \times 10^{-19}$ M or less, about $1 \times 10^{-11}$ M or less, about $1 \times 10^{-12}$ M or less, or about $1 \times 10^{-13}$ M or less. Alternatively, "specific binding" refers to the ability of the FN3 domain of the invention to bind CD137 at least 5-fold above the negative control in standard ELISA assay. The isolated FN3 domain of the invention that specifically binds CD137 may, however, have cross-reactivity to other related antigens, for example to the same predetermined antigen from other species (homologs), such as *Macaca Fascicularis* (cynomolgous monkey, cyno) or *Pan troglodytes* (chimpanzee).

"Library" refers to a collection of variants. The library may be composed of polypeptide or polynucleotide variants.

"Stability" refers to the ability of a molecule to maintain a folded state under physiological conditions such that it retains at least one of its normal functional activities, for example, binding to a predetermined antigen such as CD137.

"CD137" refers to human CD137 protein having the amino acid sequence of SEQ ID NO:44.

"Tencon" refers to the synthetic fibronectin type III (FN3) domain having the sequence shown in SEQ ID NO:1 and described in U.S. Pat. Publ. No. 2010/0216708.

A "cancer cell" or a "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

"Vector" refers to a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than about 50 amino acids may be referred to as "peptides".

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Subject" includes any human or nonhuman animal. "Nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

"Isolated" refers to a homogenous population of molecules (such as synthetic polynucleotides or a polypeptide such as FN3 domains) which have been substantially separated and/or purified away from other components of the system the molecules are produced in, such as a recombinant cell, as well as a protein that has been subjected to at least one purification or isolation step. "Isolated FN3 domain" refers to an FN3 domain that is substantially free of other cellular material and/or chemicals and encompasses FN3 domains that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

Compositions of Matter

The present invention provides fibronectin type III (FN3) domains that specifically bind human CD137 protein (SEQ ID NO:44). These molecules can be used in therapeutic and diagnostic applications and in imaging. The present invention provides polynucleotides encoding the FN3 domains of the invention or complementary nucleic acids thereof, vectors, host cells, and methods of making and using them.

The invention provides an isolated FN3 domain that specifically binds CD137.

The FN3 domain of the invention may bind CD137 with a dissociation constant ($K_D$) of less than about $1 \times 10^{-7}$ M, for example less than about $1 \times 10^{-8}$ M, less than about $1 \times 10^{-9}$ M, less than about $1 \times 10^{-10}$ M, less than about $1 \times 10^{-11}$ M, less than about $1 \times 10^{-12}$ M, or less than about $1 \times 10^{-13}$ M as determined by surface plasmon resonance or the Kinexa method, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are made with standardized solutions of protein scaffold and antigen, and a standardized buffer, such as the buffer described herein.

The FN3 domain of the invention may bind CD137 at least 5-fold above the signal obtained for a negative control in standard ELISA assay.

In some embodiments, the FN3 domain that specifically binds CD137 comprises an initiator methionine (Met) linked to the N-terminus of the molecule.

In some embodiments, the FN3 domain that specifically binds CD137 comprises a cysteine (Cys) linked to a C-terminus of the FN3 domain.

The addition of the N-terminal Met and/or the C-terminal Cys may facilitate expression and/or conjugation of half-life extending molecules.

In some embodiments, the FN3 domain that specifically binds CD137 is internalized into a cell.

Internalization of the FN3 domain may facilitate delivery of a cytotoxic agent into tumor cells.

In some embodiments, the FN3 domain that specifically binds CD137 inhibits binding of the CD137 ligand (4-1BBL) to CD137.

Inhibition of binding of 4-1BBL to CD137 by the FN3 domains of the invention may be assessed using competition ELISA. In an exemplary assay, 1 µg/ml recombinant human CD137 is bound on wells of microtiter plates, the wells are washed and blocked, and 10 µg/ml of the test FN3 domain is added. Without washing, 7.5 μg/ml 4-1BBL is added into the wells and incubated for 30 min, after which 0.5 μg/ml anti-4-1BBL antibodies are added and incubated for 30 min. The plates are washed and 0.5 μg/mL neutravidin-HRP conjugate polyclonal antibody is added and incubated for 30 minutes. The plates are washed and POD Chemiluminescence substrate added immediately prior to reading the luminescence signal. The FN3 domains of the invention inhibit binding of 4-1BBL to CD137 when the binding of 4-1BBL is reduced by at least about 80%, 85%, 90%, 95% or 100%.

In some embodiments, the FN3 domain that specifically binds CD137 is a CD137 antagonist.

In some embodiments, the FN3 domain that specifically binds CD137 is a CD137 agonist.

"Antagonist" refers to a FN3 domain that specifically binds CD137 that suppresses at least one activity of CD137 function by inhibiting CD137 binding to to its natural ligand 4-1BB1 or inhibiting CD137 binding to other molecules. A molecule is an antagonist when the at least one reaction or activity is suppressed by at least about 30%, 40%, 45%, 50%, 55%, 60%, 65%, 70%, 75%, 80%, 85%, 90%, 95%, or 100% more than the at least one reaction or activity suppressed in the absence of the antagonist (e.g., negative control), or when the suppression is statistically significant when compared to the suppression in the absence of the antagonist. A typical reaction or activity that is induced by 4-1BBL binding to CD137 is upregulation of survival genes, enhanced cell division, induced cytokine production, and prevention of activation-induced cell death in T cells.

The antagonistic FN3 domains that specifically bind CD137 may be used in the treatment of autoimmune or inflammatory diseases and in general diseases in which suppression of T cell responses is desirable.

"Agonist" refers to a FN3 domain that specifically binds CD137 that induces at least one reaction or activity that is induced by CD137. The FN3 domain is an agonist when the at least one reaction or activity is induced by at least about 30%, 40%, 45%, 50%, 55%, 60%, 65%, 70%, 75%, 80%, 85%, 90%, 95%, or 100% greater than the at least one reaction or activity induced in the absence of the agonist (e.g., negative control), or when the induction is statistically significant when compared to the induction in the absence of the agonist. A typical reaction or activity that is induced by 4-1BBL binding to CD137 is upregulation of survival genes, enhanced cell division, induced cytokine production, and prevention of activation-induced cell death in T cells.

The agonistic FN3 domains that specifically bind CD137 may be used, for example, in the treatment of cancer or viral infections and in general in treatment of diseases in which activation of T cell responses is desirable.

In some embodiments, the FN3 domain that specifically binds CD137 does not inhibit 4-1BBL binding to CD137.

In some embodiments, the FN3 domain that specifically binds CD137 is based on Tencon sequence of SEQ ID NO:1 or Tencon 27 sequence of SEQ ID NO:4, optionally having substitutions at residues positions 11, 14, 17, 37, 46, 73, or 86 (residue numbering corresponding to SEQ ID NO:4).

The invention also provides an isolated FN3 domain that specifically binds CD137 comprising the amino acid sequence of SEQ ID NOs: 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, or 224.

The invention also provides an isolated FN3 domain that specifically binds CD137 comprising the amino acid sequence of SEQ ID NO:45.

The invention also provides an isolated FN3 domain that specifically binds CD137 comprising the amino acid sequence of SEQ ID NO:46.

The invention also provides an isolated FN3 domain that specifically binds CD137 comprising the amino acid sequence of SEQ ID NO:47.

The invention also provides an isolated FN3 domain that specifically binds CD137 comprising the amino acid sequence of SEQ ID NO:48.

The invention also provides an isolated FN3 domain that specifically binds CD137 comprising the amino acid sequence of SEQ ID NO:49.

The invention also provides an isolated FN3 domain that specifically binds CD137 comprising the amino acid sequence of SEQ ID NO:50.

The invention also provides an isolated FN3 domain that specifically binds CD137 comprising the amino acid sequence of SEQ ID NO:51.

The invention also provides an isolated FN3 domain that specifically binds CD137 comprising the amino acid sequence of SEQ ID NO:52.

The invention also provides an isolated FN3 domain that specifically binds CD137 comprising the amino acid sequence of SEQ ID NO:53.

The invention also provides an isolated FN3 domain that specifically binds CD137 comprising the amino acid sequence of SEQ ID NO:54.

The invention also provides an isolated FN3 domain that specifically binds CD137 comprising the amino acid sequence of SEQ ID NO:55.

The invention also provides an isolated FN3 domain that specifically binds CD137 comprising the amino acid sequence of SEQ ID NO:56.

The invention also provides an isolated FN3 domain that specifically binds CD137 comprising the amino acid sequence of SEQ ID NO:57.

The invention also provides an isolated FN3 domain that specifically binds CD137 comprising the amino acid sequence of SEQ ID NO:58.

The invention also provides an isolated FN3 domain that specifically binds CD137 comprising the amino acid sequence of SEQ ID NO:59.

The invention also provides an isolated FN3 domain that specifically binds CD137 comprising the amino acid sequence of SEQ ID NO:60.

The invention also provides an isolated FN3 domain that specifically binds CD137 comprising the amino acid sequence of SEQ ID NO:61.

The invention also provides an isolated FN3 domain that specifically binds CD137 comprising the amino acid sequence of SEQ ID NO:62.

The invention also provides an isolated FN3 domain that specifically binds CD137 comprising the amino acid sequence of SEQ ID NO:63.

The invention also provides an isolated FN3 domain that specifically binds CD137 comprising the amino acid sequence of SEQ ID NO:64.

The invention also provides an isolated FN3 domain that specifically binds CD137 comprising the amino acid sequence of SEQ ID NO:65.

The invention also provides an isolated FN3 domain that specifically binds CD137 comprising the amino acid sequence of SEQ ID NO:66.

The invention also provides an isolated FN3 domain that specifically binds CD137 comprising the amino acid sequence of SEQ ID NO:67.

The invention also provides an isolated FN3 domain that specifically binds CD137 comprising the amino acid sequence of SEQ ID NO:68.

The invention also provides an isolated FN3 domain that specifically binds CD137 comprising the amino acid sequence of SEQ ID NO:69.

The invention also provides an isolated FN3 domain that specifically binds CD137 comprising the amino acid sequence of SEQ ID NO:70.

The invention also provides an isolated FN3 domain that specifically binds CD137 comprising the amino acid sequence of SEQ ID NO:71.

The invention also provides an isolated FN3 domain that specifically binds CD137 comprising the amino acid sequence of SEQ ID NO:72.

The invention also provides an isolated FN3 domain that specifically binds CD137 comprising the amino acid sequence of SEQ ID NO:73.

The invention also provides an isolated FN3 domain that specifically binds CD137 comprising the amino acid sequence of SEQ ID NO:74.

The invention also provides an isolated FN3 domain that specifically binds CD137 comprising the amino acid sequence of SEQ ID NO:75.

The invention also provides an isolated FN3 domain that specifically binds CD137 comprising the amino acid sequence of SEQ ID NO:76.

The invention also provides an isolated FN3 domain that specifically binds CD137 comprising the amino acid sequence of SEQ ID NO:77.

The invention also provides an isolated FN3 domain that specifically binds CD137 comprising the amino acid sequence of SEQ ID NO:78.

The invention also provides an isolated FN3 domain that specifically binds CD137 comprising the amino acid sequence of SEQ ID NO:79.

The invention also provides an isolated FN3 domain that specifically binds CD137 comprising the amino acid sequence of SEQ ID NO:80.

The invention also provides an isolated FN3 domain that specifically binds CD137 comprising the amino acid sequence of SEQ ID NO:81.

The invention also provides an isolated FN3 domain that specifically binds CD137 comprising the amino acid sequence of SEQ ID NO:82.

The invention also provides an isolated FN3 domain that specifically binds CD137 comprising the amino acid sequence of SEQ ID NO:83.

The invention also provides an isolated FN3 domain that specifically binds CD137 comprising the amino acid sequence of SEQ ID NO:84.

The invention also provides an isolated FN3 domain that specifically binds CD137 comprising the amino acid sequence of SEQ ID NO:85.

The invention also provides an isolated FN3 domain that specifically binds CD137 comprising the amino acid sequence of SEQ ID NO:86.

The invention also provides an isolated FN3 domain that specifically binds CD137 comprising the amino acid sequence of SEQ ID NO:87.

The invention also provides an isolated FN3 domain that specifically binds CD137 comprising the amino acid sequence of SEQ ID NO:88.

The invention also provides an isolated FN3 domain that specifically binds CD137 comprising the amino acid sequence of SEQ ID NO:89.

The invention also provides an isolated FN3 domain that specifically binds CD137 comprising the amino acid sequence of SEQ ID NO:90.

The invention also provides an isolated FN3 domain that specifically binds CD137 comprising the amino acid sequence of SEQ ID NO:91.

The invention also provides an isolated FN3 domain that specifically binds CD137 comprising the amino acid sequence of SEQ ID NO:92.

The invention also provides an isolated FN3 domain that specifically binds CD137 comprising the amino acid sequence of SEQ ID NO:93.

The invention also provides an isolated FN3 domain that specifically binds CD137 comprising the amino acid sequence of SEQ ID NO:94.

The invention also provides an isolated FN3 domain that specifically binds CD137 comprising the amino acid sequence of SEQ ID NO:95.

The invention also provides an isolated FN3 domain that specifically binds CD137 comprising the amino acid sequence of SEQ ID NO:96.

The invention also provides an isolated FN3 domain that specifically binds CD137 comprising the amino acid sequence of SEQ ID NO:97.

The invention also provides an isolated FN3 domain that specifically binds CD137 comprising the amino acid sequence of SEQ ID NO:98.

The invention also provides an isolated FN3 domain that specifically binds CD137 comprising the amino acid sequence of SEQ ID NO:99.

The invention also provides an isolated FN3 domain that specifically binds CD137 comprising the amino acid sequence of SEQ ID NO:100.

The invention also provides an isolated FN3 domain that specifically binds CD137 comprising the amino acid sequence of SEQ ID NO:101.

The invention also provides an isolated FN3 domain that specifically binds CD137 comprising the amino acid sequence of SEQ ID NO:102.

The invention also provides an isolated FN3 domain that specifically binds CD137 comprising the amino acid sequence of SEQ ID NO:103.

The invention also provides an isolated FN3 domain that specifically binds CD137 comprising the amino acid sequence of SEQ ID NO:104.

The invention also provides an isolated FN3 domain that specifically binds CD137 comprising the amino acid sequence of SEQ ID NO:105.

The invention also provides an isolated FN3 domain that specifically binds CD137 comprising the amino acid sequence of SEQ ID NO:106.

The invention also provides an isolated FN3 domain that specifically binds CD137 comprising the amino acid sequence of SEQ ID NO:107.

The invention also provides an isolated FN3 domain that specifically binds CD137 comprising the amino acid sequence of SEQ ID NO:108.

The invention also provides an isolated FN3 domain that specifically binds CD137 comprising the amino acid sequence of SEQ ID NO:109.

The invention also provides an isolated FN3 domain that specifically binds CD137 comprising the amino acid sequence of SEQ ID NO:110.

The invention also provides an isolated FN3 domain that specifically binds CD137 comprising the amino acid sequence of SEQ ID NO:111.

The invention also provides an isolated FN3 domain that specifically binds CD137 comprising the amino acid sequence of SEQ ID NO:112.

The invention also provides an isolated FN3 domain that specifically binds CD137 comprising the amino acid sequence of SEQ ID NO:113.

The invention also provides an isolated FN3 domain that specifically binds CD137 comprising the amino acid sequence of SEQ ID NO:114.

The invention also provides an isolated FN3 domain that specifically binds CD137 comprising the amino acid sequence of SEQ ID NO:115.

The invention also provides an isolated FN3 domain that specifically binds CD137 comprising the amino acid sequence of SEQ ID NO:116.

The invention also provides an isolated FN3 domain that specifically binds CD137 comprising the amino acid sequence of SEQ ID NO:117.

The invention also provides an isolated FN3 domain that specifically binds CD137 comprising the amino acid sequence of SEQ ID NO:118.

The invention also provides an isolated FN3 domain that specifically binds CD137 comprising the amino acid sequence of SEQ ID NO:119.

The invention also provides an isolated FN3 domain that specifically binds CD137 comprising the amino acid sequence of SEQ ID NO:120.

The invention also provides an isolated FN3 domain that specifically binds CD137 comprising the amino acid sequence of SEQ ID NO:121.

The invention also provides an isolated FN3 domain that specifically binds CD137 comprising the amino acid sequence of SEQ ID NO:122.

The invention also provides an isolated FN3 domain that specifically binds CD137 comprising the amino acid sequence of SEQ ID NO:123.

The invention also provides an isolated FN3 domain that specifically binds CD137 comprising the amino acid sequence of SEQ ID NO:124.

The invention also provides an isolated FN3 domain that specifically binds CD137 comprising the amino acid sequence of SEQ ID NO:125.

The invention also provides an isolated FN3 domain that specifically binds CD137 comprising the amino acid sequence of SEQ ID NO:126.

The invention also provides an isolated FN3 domain that specifically binds CD137 comprising the amino acid sequence of SEQ ID NO:127.

The invention also provides an isolated FN3 domain that specifically binds CD137 comprising the amino acid sequence of SEQ ID NO:128.

The invention also provides an isolated FN3 domain that specifically binds CD137 comprising the amino acid sequence of SEQ ID NO:129.

The invention also provides an isolated FN3 domain that specifically binds CD137 comprising the amino acid sequence of SEQ ID NO:130.

The invention also provides an isolated FN3 domain that specifically binds CD137 comprising the amino acid sequence of SEQ ID NO:131.

The invention also provides an isolated FN3 domain that specifically binds CD137 comprising the amino acid sequence of SEQ ID NO:132.

The invention also provides an isolated FN3 domain that specifically binds CD137 comprising the amino acid sequence of SEQ ID NO:133.

The invention also provides an isolated FN3 domain that specifically binds CD137 comprising the amino acid sequence of SEQ ID NO:134.

The invention also provides an isolated FN3 domain that specifically binds CD137 comprising the amino acid sequence of SEQ ID NO:135.

The invention also provides an isolated FN3 domain that specifically binds CD137 comprising the amino acid sequence of SEQ ID NO:136.

The invention also provides an isolated FN3 domain that specifically binds CD137 comprising the amino acid sequence of SEQ ID NO:137.

The invention also provides an isolated FN3 domain that specifically binds CD137 comprising the amino acid sequence of SEQ ID NO:138.

The invention also provides an isolated FN3 domain that specifically binds CD137 comprising the amino acid sequence of SEQ ID NO:139.

The invention also provides an isolated FN3 domain that specifically binds CD137 comprising the amino acid sequence of SEQ ID NO:140.

The invention also provides an isolated FN3 domain that specifically binds CD137 comprising the amino acid sequence of SEQ ID NO:141.

The invention also provides an isolated FN3 domain that specifically binds CD137 comprising the amino acid sequence of SEQ ID NO:142.

The invention also provides an isolated FN3 domain that specifically binds CD137 comprising the amino acid sequence of SEQ ID NO:143.

The invention also provides an isolated FN3 domain that specifically binds CD137 comprising the amino acid sequence of SEQ ID NO:144.

The invention also provides an isolated FN3 domain that specifically binds CD137 comprising the amino acid sequence of SEQ ID NO:145.

The invention also provides an isolated FN3 domain that specifically binds CD137 comprising the amino acid sequence of SEQ ID NO:146.

The invention also provides an isolated FN3 domain that specifically binds CD137 comprising the amino acid sequence of SEQ ID NO:147.

The invention also provides an isolated FN3 domain that specifically binds CD137 comprising the amino acid sequence of SEQ ID NO:148.

The invention also provides an isolated FN3 domain that specifically binds CD137 comprising the amino acid sequence of SEQ ID NO:149.

The invention also provides an isolated FN3 domain that specifically binds CD137 comprising the amino acid sequence of SEQ ID NO:150.

The invention also provides an isolated FN3 domain that specifically binds CD137 comprising the amino acid sequence of SEQ ID NO:151.

The invention also provides an isolated FN3 domain that specifically binds CD137 comprising the amino acid sequence of SEQ ID NO:152.

The invention also provides an isolated FN3 domain that specifically binds CD137 comprising the amino acid sequence of SEQ ID NO:153.

The invention also provides an isolated FN3 domain that specifically binds CD137 comprising the amino acid sequence of SEQ ID NO:154.

The invention also provides an isolated FN3 domain that specifically binds CD137 comprising the amino acid sequence of SEQ ID NO:155.

The invention also provides an isolated FN3 domain that specifically binds CD137 comprising the amino acid sequence of SEQ ID NO:156.

The invention also provides an isolated FN3 domain that specifically binds CD137 comprising the amino acid sequence of SEQ ID NO:157.

The invention also provides an isolated FN3 domain that specifically binds CD137 comprising the amino acid sequence of SEQ ID NO:158.

The invention also provides an isolated FN3 domain that specifically binds CD137 comprising the amino acid sequence of SEQ ID NO:159.

The invention also provides an isolated FN3 domain that specifically binds CD137 comprising the amino acid sequence of SEQ ID NO:160.

The invention also provides an isolated FN3 domain that specifically binds CD137 comprising the amino acid sequence of SEQ ID NO:161.

The invention also provides an isolated FN3 domain that specifically binds CD137 comprising the amino acid sequence of SEQ ID NO:162.

The invention also provides an isolated FN3 domain that specifically binds CD137 comprising the amino acid sequence of SEQ ID NO:163.

The invention also provides an isolated FN3 domain that specifically binds CD137 comprising the amino acid sequence of SEQ ID NO:164.

The invention also provides an isolated FN3 domain that specifically binds CD137 comprising the amino acid sequence of SEQ ID NO:165.

The invention also provides an isolated FN3 domain that specifically binds CD137 comprising the amino acid sequence of SEQ ID NO:166.

The invention also provides an isolated FN3 domain that specifically binds CD137 comprising the amino acid sequence of SEQ ID NO:167.

The invention also provides an isolated FN3 domain that specifically binds CD137 comprising the amino acid sequence of SEQ ID NO:168.

The invention also provides an isolated FN3 domain that specifically binds CD137 comprising the amino acid sequence of SEQ ID NO:169.

The invention also provides an isolated FN3 domain that specifically binds CD137 comprising the amino acid sequence of SEQ ID NO:170.

The invention also provides an isolated FN3 domain that specifically binds CD137 comprising the amino acid sequence of SEQ ID NO:171.

The invention also provides an isolated FN3 domain that specifically binds CD137 comprising the amino acid sequence of SEQ ID NO:172.

The invention also provides an isolated FN3 domain that specifically binds CD137 comprising the amino acid sequence of SEQ ID NO:173.

The invention also provides an isolated FN3 domain that specifically binds CD137 comprising the amino acid sequence of SEQ ID NO:174.

The invention also provides an isolated FN3 domain that specifically binds CD137 comprising the amino acid sequence of SEQ ID NO:175.

The invention also provides an isolated FN3 domain that specifically binds CD137 comprising the amino acid sequence of SEQ ID NO:176.

The invention also provides an isolated FN3 domain that specifically binds CD137 comprising the amino acid sequence of SEQ ID NO:177.

The invention also provides an isolated FN3 domain that specifically binds CD137 comprising the amino acid sequence of SEQ ID NO:178.

The invention also provides an isolated FN3 domain that specifically binds CD137 comprising the amino acid sequence of SEQ ID NO:179.

The invention also provides an isolated FN3 domain that specifically binds CD137 comprising the amino acid sequence of SEQ ID NO:180.

The invention also provides an isolated FN3 domain that specifically binds CD137 comprising the amino acid sequence of SEQ ID NO:181.

The invention also provides an isolated FN3 domain that specifically binds CD137 comprising the amino acid sequence of SEQ ID NO:182.

The invention also provides an isolated FN3 domain that specifically binds CD137 comprising the amino acid sequence of SEQ ID NO:183.

The invention also provides an isolated FN3 domain that specifically binds CD137 comprising the amino acid sequence of SEQ ID NO:184.

The invention also provides an isolated FN3 domain that specifically binds CD137 comprising the amino acid sequence of SEQ ID NO:185.

The invention also provides an isolated FN3 domain that specifically binds CD137 comprising the amino acid sequence of SEQ ID NO:186.

The invention also provides an isolated FN3 domain that specifically binds CD137 comprising the amino acid sequence of SEQ ID NO:187.

The invention also provides an isolated FN3 domain that specifically binds CD137 comprising the amino acid sequence of SEQ ID NO:188.

The invention also provides an isolated FN3 domain that specifically binds CD137 comprising the amino acid sequence of SEQ ID NO:189.

The invention also provides an isolated FN3 domain that specifically binds CD137 comprising the amino acid sequence of SEQ ID NO:190.

The invention also provides an isolated FN3 domain that specifically binds CD137 comprising the amino acid sequence of SEQ ID NO:191.

The invention also provides an isolated FN3 domain that specifically binds CD137 comprising the amino acid sequence of SEQ ID NO:192.

The invention also provides an isolated FN3 domain that specifically binds CD137 comprising the amino acid sequence of SEQ ID NO:193.

The invention also provides an isolated FN3 domain that specifically binds CD137 comprising the amino acid sequence of SEQ ID NO:194.

The invention also provides an isolated FN3 domain that specifically binds CD137 comprising the amino acid sequence of SEQ ID NO:195.

The invention also provides an isolated FN3 domain that specifically binds CD137 comprising the amino acid sequence of SEQ ID NO:196.

The invention also provides an isolated FN3 domain that specifically binds CD137 comprising the amino acid sequence of SEQ ID NO:197.

The invention also provides an isolated FN3 domain that specifically binds CD137 comprising the amino acid sequence of SEQ ID NO:198.

The invention also provides an isolated FN3 domain that specifically binds CD137 comprising the amino acid sequence of SEQ ID NO:199.

The invention also provides an isolated FN3 domain that specifically binds CD137 comprising the amino acid sequence of SEQ ID NO:200.

The invention also provides an isolated FN3 domain that specifically binds CD137 comprising the amino acid sequence of SEQ ID NO:201.

The invention also provides an isolated FN3 domain that specifically binds CD137 comprising the amino acid sequence of SEQ ID NO:202.

The invention also provides an isolated FN3 domain that specifically binds CD137 comprising the amino acid sequence of SEQ ID NO:203.

The invention also provides an isolated FN3 domain that specifically binds CD137 comprising the amino acid sequence of SEQ ID NO:204.

The invention also provides an isolated FN3 domain that specifically binds CD137 comprising the amino acid sequence of SEQ ID NO:205.

The invention also provides an isolated FN3 domain that specifically binds CD137 comprising the amino acid sequence of SEQ ID NO:206.

The invention also provides an isolated FN3 domain that specifically binds CD137 comprising the amino acid sequence of SEQ ID NO:207.

The invention also provides an isolated FN3 domain that specifically binds CD137 comprising the amino acid sequence of SEQ ID NO:208.

The invention also provides an isolated FN3 domain that specifically binds CD137 comprising the amino acid sequence of SEQ ID NO:209.

The invention also provides an isolated FN3 domain that specifically binds CD137 comprising the amino acid sequence of SEQ ID NO:210.

The invention also provides an isolated FN3 domain that specifically binds CD137 comprising the amino acid sequence of SEQ ID NO:211.

The invention also provides an isolated FN3 domain that specifically binds CD137 comprising the amino acid sequence of SEQ ID NO:212.

The invention also provides an isolated FN3 domain that specifically binds CD137 comprising the amino acid sequence of SEQ ID NO:213.

The invention also provides an isolated FN3 domain that specifically binds CD137 comprising the amino acid sequence of SEQ ID NO:214.

The invention also provides an isolated FN3 domain that specifically binds CD137 comprising the amino acid sequence of SEQ ID NO:215.

The invention also provides an isolated FN3 domain that specifically binds CD137 comprising the amino acid sequence of SEQ ID NO:216.

The invention also provides an isolated FN3 domain that specifically binds CD137 comprising the amino acid sequence of SEQ ID NO:217.

The invention also provides an isolated FN3 domain that specifically binds CD137 comprising the amino acid sequence of SEQ ID NO:218.

The invention also provides an isolated FN3 domain that specifically binds CD137 comprising the amino acid sequence of SEQ ID NO:219.

The invention also provides an isolated FN3 domain that specifically binds CD137 comprising the amino acid sequence of SEQ ID NO:220.

The invention also provides an isolated FN3 domain that specifically binds CD137 comprising the amino acid sequence of SEQ ID NO:221.

The invention also provides an isolated FN3 domain that specifically binds CD137 comprising the amino acid sequence of SEQ ID NO:222.

The invention also provides an isolated FN3 domain that specifically binds CD137 comprising the amino acid sequence of SEQ ID NO:223.

The invention also provides an isolated FN3 domain that specifically binds CD137 comprising the amino acid sequence of SEQ ID NO:224.

In some embodiments, the isolated FN3 domain that specifically binds CD137 comprises an initiator methionine (Met) linked to the N-terminus of the molecule.

In some embodiments, the isolated FN3 domain that specifically binds CD137 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 45-224.

Conjugates of the FN3 Domains that Specifically Bind CD137 of the Invention

The invention also provides an isolated FN3 domain that specifically binds CD137 conjugated to a heterologous molecule(s).

In some embodiments, the heterologous molecule is a detectable label or a cytotoxic agent.

The invention also provides an FN3 domain that specifically binds CD137 conjugated to a detectable label.

The invention also provides an FN3 domain that specifically binds CD137 conjugated to a cytotoxic agent.

In some embodiments, the detectable label is also a cytotoxic agent.

The FN3 domains that specifically bind CD137 of the invention conjugated to a detectable label can be used to evaluate expression of CD137 on samples such as tumor tissue in vivo or in vitro.

Detectable label includes compositions that when conjugated to the FN3 domains that specifically bind CD137 of the invention renders the latter detectable, via spectroscopic, photochemical, biochemical, immunochemical, or chemical means.

Exemplary detectable labels include radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, cintillants, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In other cases the detectable label emits a signal as a result of being stimulated by an external field.

Exemplary radioactive isotopes may be γ-emitting, Auger-emitting, β-emitting, an alpha-emitting or positron-emitting radioactive isotope. Exemplary radioactive isotopes include $^3$H, $^{11}$C, $^{13}$C, $^{15}$N, $^{18}$F, $^{19}$F, $^{55}$Co, $^{57}$Co, $^{60}$Co, $^{61}$Cu, $^{62}$Cu, $^{64}$Cu, $^{67}$Cu, $^{68}$Ga, $^{72}$As, $^{75}$Br, $^{86}$Y, $^{89}$Zr, $^{90}$Sr, $^{94m}$Tc, $^{99m}$Tc, $^{115}$In, $^{123}$I, $^{124}$I, $^{125}$I, $^{131}$I, $^{211}$At, $^{212}$Bi, $^{213}$Bi, $^{223}$Ra, $^{226}$Ra, $^{225}$Ac and $^{227}$Ac.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e., iodine) to 83 (i.e., bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^+$, $Ca^{2+}$, $Cr^{2+}$, $Cr^{3+}$, $Cr^{6+}$, $Co^{2+}$, $Co^{3+}$, $Cu^+$, $Cu^{2+}$, $Cu^{3+}$, $Ga^{3+}$, $Gd^{3+}$, $Au^+$, $Au^{3+}$, $Fe^{2+}$, $Fe^{3+}$, $F^{3+}$, $Pb^{2+}$, $Mn^{2+}$, $Mn^{3+}$, $Mn^{7+}$, $Hg^{2+}$, $Ni^{2+}$, $Ni^{3+}$, $Ag^+$, $Sr^{2+}$, $Sn^{2+}$, $Sn^{4+}$, and $Zn^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyante (FITC), fluorescein thiosemicarbazide, rhodamine, Texas Red, CyDyes (e.g., Cy3, Cy5, Cy5.5), Alexa Fluors (e.g., Alexa488, Alexa555, Alexa594; Alexa647), near infrared (NIR) (700-900 nm) fluorescent dyes, and carbocyanine and aminostyryl dyes.

The FN3 domains that specifically bind CD137 conjugated to a detectable label may be used as an imaging agent to evaluate tumor distribution, diagnosis for the presence of tumor cells and/or, recurrence of tumor.

In some embodiments, the FN3 domains that specifically bind CD137 of the invention are conjugated to a cytotoxic agent.

In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The FN3 domains that specifically bind CD137 conjugated to a cytotoxic agent of the invention may be used in the targeted delivery of the cytotoxic agent to CD137 expressing tumor cell, and intracellular accumulation therein, wherein systemic administration of these unconjugated cytotoxic agents may result in unacceptable levels of toxicity to normal cells.

In some embodiments, the cytotoxic agent is daunomycin, doxorubicin, methotrexate, vindesine, bacterial toxins such as diphtheria toxin, ricin, geldanamycin, maytansinoids or calicheamicin. The cytotoxic agent may elicit their cytotoxic and cytostatic effects by mechanisms including tubulin binding, DNA binding, or topoisomerase inhibition.

In some embodiments, the cytotoxic agent is an enzymatically active toxins such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In some embodiments, the cytotoxic agent is a radionuclide, such as $^{212}$Bi, $^{131}$I, $^{131}$In, $^{90}$Y, and $^{186}$Re.

In some embodiments, the cytotoxic agent is dolastatins or dolostatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancerand antifungal activity. The dolastatin or auristatin drug moiety may be attached to the FN3 domain of the invention through the N (amino) terminus or the C (carboxyl) terminus of the peptidic drug moiety (WO 02/088172), or via any cysteine engineered into the FN3 domain.

The FN3 domains that specifically bind CD137 of the invention may be conjugated to a detectable label using known methods.

In some embodiments, the detectable label is complexed with a chelating agent.

In some embodiments, the detectable label is conjugated to the FN3 domain that specifically binds CD137 of the invention via a linker.

The detectable label or the cytotoxic moiety may be linked directly, or indirectly, to the FN3 domain that specifically binds CD137 of the invention using known methods. Suitable linkers are known in the art and include, for example, prosthetic groups, non-phenolic linkers (derivatives of N-succinimidyl-benzoates; dodecaborate), chelating moieties of both macrocyclics and acyclic chelators, such as derivatives of 1,4,7,10-tetraazacyclododecane-1,4,7,10,tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene) and other chelating moieties. Suitable peptide linkers are well known.

In some embodiment, the FN3 domain that specifically binds CD137 is removed from the blood via renal clearance.

Isolation of CD137 Binding FN3 Domains from a Library Based on Tencon Sequence

Tencon (SEQ ID NO:1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, may be randomized in order to construct libraries of fibronectin type III (FN3) domains that may be used to select novel molecules that bind CD137. Table 1 shows positions and sequences of each loop and beta-strand in Tencon (SEQ ID NO:1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence. The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is described in U.S. Pat. Publ. No. 2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO:1), and which variants display improve thermal stability. Exemplary Tencon variants are described in US Pat. Publ. No. 2011/0274623, and include Tencon27 (SEQ ID NO:4) having substitutions E11R, L17A, N46V and E86I when compared to Tencon of SEQ ID NO:1.

TABLE 1

Tencon topology

| FN3 domain | Tencon (SEQ ID NO: 1) |
| --- | --- |
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http:_//www_s-loning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well-known IUB code.

The FN3 domains that specifically bind CD137 of the invention may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci USA 101, 2806-2810, 2004), and assaying the library for specific binding to PSMA by any method known in the art and described in the Example. Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains that specifically bind CD137 are further characterized for their binding to CD137, modulation of CD137 activity, internalization, stability, and other desired characteristics.

The FN3 domains that specifically bind CD137 of the invention may be generated using any FN3 domain as a template to generate a library and screening the library for molecules specifically binding CD137 using methods provided within. Exemplar FN3 domains that may be used are the 3rd FN3 domain of tenascin C (TN3) (SEQ ID NO:32), Fibcon (SEQ ID NO:33), and the 10th FN3 domain of fibronectin (FN10) (SEQ ID NO:34). Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak, Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/085462; U.S. Pat. Nos. 6,969,108; 6,172,197; 5,223,409; 6,582,915; 6,472,147).

In some embodiments. the FN3 domain that specifically binds CD137 is based on Tencon sequence of SEQ ID NO:1 or Tencon27 sequence of SEQ ID NO:4, the SEQ ID NO:1 or the SEQ ID NO:4, optionally having substitutions at residues positions 11, 14, 17, 37, 46, 73, and/or 86.

The FN3 domains that specifically bind CD137 of the invention may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr Opin Biotechnol, 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO:1) are residue positions 11, 14, 17, 37, 46, 73, or 86, and are described in US Pat. Publ. No. 2011/0274623. Substitutions corresponding to these residues may be incorporated to the FN3 domain containing molecules of the invention.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three dimensional structure.

In one embodiment, the FN3 domain that specifically binds CD137 of the invention may exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the $T_m$.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid (CH3COOH), halogenated acetic acids), hydrophobic molecules (e.g. phospholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domain that specifically binds CD137 may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include (GS)$_2$, (SEQ ID NO:35), (GGGS)$_2$ (SEQ ID NO:36), (GGGGS)$_5$ (SEQ ID NO:37), (AP)$_2$ (SEQ ID NO:38), (AP)$_5$ (SEQ ID NO:39), (AP)$_{10}$ (SEQ ID NO:40), (AP)$_{20}$ (SEQ ID NO:41) and A(EAAAK)$_5$AAA (SEQ ID NO:42). The dimers and multimers may be linked to each other in a N- to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Half-Life Extending Moieties

The FN3 domains that specifically bind CD137 may incorporate other subunits for example via covalent interaction. In one aspect of the invention, the FN3 domains that specifically bind CD137 further comprise a half-life extending moiety. Exemplary half-life extending moieties are albumin, albumin variants, albumin-binding proteins and/or domains, transferrin and fragments and analogues thereof, and Fc regions. An exemplary albumin variant is shown in SEQ ID NO:43. Amino acid sequences of the human Fc regions are well known, and include IgG1, IgG2, IgG3, IgG4, IgM, IgA and IgE Fc regions.

All or a portion of an antibody constant region may be attached to the FN3 domain that specifically binds CD137 to impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and may be further modified by modifying residues in the Fc responsible for these activities (for review; see Strohl, *Curr Opin Biotechnol.* 20, 685-691, 2009).

Additional moieties may be incorporated into the FN3 domains that specifically bind CD137 such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules of the invention.

A pegyl moiety may for example be added to the FN3 domain that specifically binds CD137 by incorporating a cysteine residue to the C-terminus of the molecule, or engineering cysteines into residue positions that face away from the CD137 binding face of the molecule, and attaching a pegyl group to the cysteine using well known methods.

FN3 domains that specifically bind CD137 incorporating additional moieties may be compared for functionality by several well-known assays. For example, altered properties due to incorporation of Fc domains and/or Fc domain variants may be assayed in Fc receptor binding assays using soluble forms of the receptors, such as the FcγRT, FcγRII, FcγRIII or FcRn receptors, or using well known cell-based assays measuring for example ADCC or CDC, or evaluating pharmacokinetic properties of the molecules of the invention in in vivo models.

Polynucleotides, Vectors, Host Cells

The invention also provides nucleic acids encoding the FN3 domains specifically binding CD137 as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof. Certain exemplary polynucleotides are disclosed herein, however, other polynucleotides which, given the degeneracy of the genetic code or codon preferences in a given expression system, encode the FN3 domains of the invention are also within the scope of the invention.

The invention also provides an isolated polynucleotide encoding the FN3 domain specifically binding CD137 comprising the amino acid sequence of SEQ ID NOs: 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, or 224.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such as PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

The invention also provides a vector comprising at least one polynucleotide of the invention. Such vectors may be plasmid vectors, viral vectors, vectors for baculovirus expression, transposon based vectors or any other vector suitable for introduction of the polynucleotides of the invention into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

The invention also provides a host cell comprising the vector of the invention. The FN3 domain that specifically bind CD137 may be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

The invention also provides a method of producing the isolated FN3 domain that specifically binds CD137, comprising culturing the isolated host cell of the invention under conditions such that the isolated FN3 domain that specifically binds CD137 is expressed, and purifying the FN3 domain.

The FN3 domains that specifically bind CD137 may be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography, or high performance liquid chromatography (HPLC).

Anti-Idiotypic Antibodies

The present invention also provides an anti-idiotypic antibody binding to the FN3 domain.

The invention also provides an anti-idiotypic antibody that specifically binds the FN3 domain comprising the amino acid sequences of one of SEQ ID NOs: 45-224.

Kits

The invention also provides a kit comprising the FN3 domain that specifically binds CD137.

The kit may be used for therapeutic uses and as a diagnostic kit.

In some embodiments, the kit comprises the FN3 domain that specifically binds CD137 and reagents for detecting the FN3 domain. The kit can include one or more other elements including: instructions for use; other reagents, e.g., a label, an agent useful for chelating, or otherwise coupling, a radioprotective composition; devices or other materials for preparing the FN3 domain that specifically binds CD137 for administration for imaging, diagnostic or therapeutic purpose; pharmaceutically acceptable carriers; and devices or other materials for administration to a subject.

In some embodiments, the kit comprises the FN3 domain that specifically binds CD137 comprising the amino acid sequences of one of SEQ ID NOs: 45-224.

Uses of CD137 Binding FN3 Domains of the Invention

The FN3 domains that specifically bind CD137 may be used to diagnose, monitor, modulate, treat, alleviate, help prevent the incidence of, or reduce the symptoms of human disease or specific pathologies in cells, tissues, organs, fluid, or, generally, a host. The FN3 domains that specifically bind CD137 may also be used in imaging CD137 positive tumor tissue in a subject. The methods of the invention may be used with an animal patient belonging to any classification. Examples of such animals include mammals such as humans, rodents, dogs, cats and farm animals.

The invention provides a method of diagnosing a subject having, or who is likely to develop cancer of a tissue based on the expression of CD137 by cells of the cancer tissue, methods of predicting success of immunotherapy, methods of prognosis, and methods of treatment.

The invention also provides a method of detecting CD137-expressing cancer cells in a tumor tissue, comprising
 obtaining a sample of the tumor tissue from a subject;
 detecting whether CD137 is expressed in the tumor tissue by contacting toe sample of the tumor tissues with the FN3 domain that specifically binds CD137 comprising the amino acid sequence of one of SEQ ID NOs: 45-224 and detecting the binding between CD137 and the FN3 domain.

The tissue can be tissue of any organ or anatomical system, for example lung, epithelial, connective, vascular, muscle, neural, skeletal, lymphatic, prostate, cervical, breast, spleen, gastric, intestinal, oral, esophageal, uterine, ovarian, renal or testicular tissue.

CD137 expression may be evaluated using known methods, such as immunohistochemistry or ELISA.

The invention also provides a method of isolating CD137 expressing cells, comprising
 obtaining a sample from a subject;
 contacting the sample with the FN3 domain that specifically binds CD137 comprising the amino acid sequence of one of SEQ ID NOs: 45-224, and
 isolating the cells bound to the FN3 domains.

The invention also provides a method of detecting CD137-expressing cancer cells in a tumor tissue, comprising
 conjugating the FN3 domain that specifically binds CD137 comprising the amino acid sequence of one of SEQ ID NOs: 45-224 to a detectable label to form a conjugate;
 administering the conjugate to a subject; and
 visualizing the CD137 expressing cancer cells to which the conjugate is bound.

The invention also provides a method of treating a subject having cancer, comprising administering to the subject a FN3 domain that specifically binds CD137 of the invention.

In some embodiments, the subject has a solid tumor.

In some embodiments, the subject has a hematological malignancy.

In some embodiments, the solid tumor is a melanoma.

In some embodiments, the solid tumor is a lung cancer.

In some embodiments, the solid tumor is a non-small cell lung cancer (NSCLC).

In some embodiments, the solid tumor is a squamous non-small cell lung cancer (NSCLC).

In some embodiments, the solid tumor is a non-squamous NSCLC.

In some embodiments, the solid tumor is a lung adenocarcinoma.

In some embodiments, the solid tumor is a renal cell carcinoma (RCC).

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer.

In some embodiments, the solid tumor is castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is pancreatic cancer.

In some embodiments, the solid tumor is a thyroid cancer.

In some embodiments, the solid tumor is a squamous cell carcinoma of the head and neck.

In some embodiments, the solid tumor is a carcinomas of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

In some embodiments, the solid tumor is a genitourinary cancer.

In some embodiments, the solid tumor is an endometriosis.

In some embodiments, the solid tumor is a cervical cancer.

In some embodiments, the solid tumor is a metastatic lesion of the cancer.

In some embodiments, the hematological malignancy is a lymphoma, a myeloma or a leukemia.

In some embodiments, the hematological malignancy is a B cell lymphoma.

In some embodiments, the hematological malignancy is Burkitt's lymphoma.

In some embodiments, the hematological malignancy is Hodgkin's lymphoma.

In some embodiments, the hematological malignancy is a non-Hodgkin's lymphoma.

In some embodiments, the hematological malignancy is a myelodysplastic syndrome.

In some embodiments, the hematological malignancy is an acute myeloid leukemia (AML).

In some embodiments, the hematological malignancy is a chronic myeloid leukemia (CML).

In some embodiments, the hematological malignancy is a chronic myelomonocytic leukemia (CMML).

In some embodiments, the hematological malignancy is a multiple myeloma (MM).

In some embodiments, the hematological malignancy is a plasmacytoma. In some embodiments, the cancer is kidney cancer.

"Treat" or "treatment" refers to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the FN3 domains that specifically bind CD137 of the invention may vary according to factors such as the disease state, age, sex, and weight of the individual. Exemplary indicators of an effective FN3 domain that specifically binds CD137 is improved well-being of the patient, decrease or shrinkage of the size of a tumor, arrested or slowed growth of a tumor, and/or absence of metastasis of cancer cells to other locations in the body.

Administration/Pharmaceutical Compositions

The invention provides for pharmaceutical compositions of the FN3 domains that specifically bind CD137, optionally conjugated to a detectable label or a cytotoxic drug of the invention and a pharmaceutically acceptable carrier. For therapeutic use, the FN3 domains that specifically bind CD137 of the invention may be prepared as pharmaceutical compositions containing an effective amount of the domain or molecule as an active ingredient in a pharmaceutically acceptable carrier. "Carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules of the invention in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21st Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the FN3 domains of the invention may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

While having described the invention in general terms, the embodiments of the invention will be further disclosed in the following examples that should not be construed as limiting the scope of the claims.

EXAMPLES

Example 1. Construction of Tencon Libraries with Randomized Loops

Tencon (SEQ ID NO:1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets.

Tencon:
(SEQ ID NO: 1)
LPAPKNLVVSEVTEDSLRLSWTAPDAAFDSFLIQYQESEKVGEAINLTVP

GSERSYDLTGLKPGTEYTVSIYGVKGGHRSNPLSAEFTT;

Various libraries were generated using the tencon scaffold and various design strategies. In general, libraries TCL1 and TCL2 produced good binders. Generation of TCL1 and TCL2 libraries are described in detail in Int. Pat. Publ. No. WO/2014081944A2.

Construction of TCL1 Library

A library designed to randomize only the FG loop of Tencon (SEQ ID NO:1), TCL1, was constructed for use with the cis-display system (Jacobs et al., Protein Engineering, Design, and Selection, 25:107-117, 2012). In this system, a single-strand DNA incorporating sequences for a Tac promoter, Tencon library coding sequence, RepA coding sequence, cis-element, and ori element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and ori elements. These two halves are combined by restriction digest in order to produce the entire construct. The TCL1 library was designed to incorporate random amino acids only in the FG loop of Tencon, KGGHRSN (SEQ ID NO:55). NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity.

TCL1 library
(SEQ ID NO: 2)
LPAPKNLVVSEVTEDSLRLSWTAPDAAFDSFLIQYQESEKVGEAINLTVP

GSERSYDLTGLKPGTEYTVSIYGVX$_{7-12}$PLSAEFTT;

wherein $X_1$, $X_2$, $X_3$, $X_4$, $X_5$, $X_6$, $X_7$ is any amino acid; and $X_8$, $X_9$, $X_{10}$, $X_{11}$ and $X_{12}$ are any amino acid or deleted Construction of TCL2 Library TCL2 library was constructed in which both the BC and the FG loops of Tencon were randomized and the distribution of amino acids at each position was strictly controlled. Table 3 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" in Table 2 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TCL2 library
(SEQ ID NO: 3)
LPAPKNLVVSEVTEDSLRLSWX$_1$X$_2$X$_3$X$_4$X$_5$X$_6$X$_7$X$_8$SFLIQYQESEKVG

EAINLTVPGSERSYDLTGLKPGTEYTVSIYGVX$_9$X$_{10}$X$_{11}$X$_{12}$X$_{13}$SX$_{14}$

X$_{15}$LSAEFTT;

wherein $X_1$ is Ala, Arg, Asn, Asp, Glu, Gln, Gly, His, Ile, Leu, Lys, Phe, Pro, Ser, Thr, Trp, Tyr or Val;

$X_2$ is Ala, Arg, Asn, Asp, Glu, Gln, Gly, His, Ile, Leu, Lys, Phe, Pro, Ser, Thr, Trp, Tyr or Val;

$X_3$ Ala, Arg, Asn, Asp, Glu, Gln, Gly, His, Ile, Leu, Lys, Phe, Pro, Ser, Thr, Trp, Tyr or Val;

$X_4$ is Ala, Arg, Asn, Asp, Glu, Gln, Gly, His, Ile, Leu, Lys, Phe, Pro, Ser, Thr, Trp, Tyr or Val;

$X_5$ is Ala, Arg, Asn, Asp, Glu, Gln, Gly, His, Ile, Leu, Lys, Phe, Pro, Ser, Thr, Trp, Tyr or Val;

$X_6$ is Ala, Arg, Asn, Asp, Glu, Gln, Gly, His, Ile, Leu, Lys, Phe, Pro, Ser, Thr, Trp, Tyr or Val;

$X_7$ is Phe, Ile, Leu, Val or Tyr;

$X_8$ is Asp, Glu or Thr;

$X_9$ is Ala, Arg, Asn, Asp, Glu, Gln, Gly, His, Ile, Leu, Lys, Phe, Pro, Ser, Thr, Trp, Tyr or Val;

$X_{10}$ is Ala, Arg, Asn, Asp, Glu, Gln, Gly, His, Ile, Leu, Lys, Phe, Pro, Ser, Thr, Trp, Tyr or Val;

$X_{11}$ is Ala, Arg, Asn, Asp, Glu, Gln, Gly, His, Ile, Leu, Lys, Phe, Pro, Ser, Thr, Trp, Tyr or Val;

$X_{12}$ is Ala, Arg, Asn, Asp, Glu, Gln, Gly, His, Ile, Leu, Lys, Phe, Pro, Ser, Thr, Trp, Tyr or Val;

$X_{13}$ is Ala, Arg, Asn, Asp, Glu, Gln, Gly, His, Ile, Leu, Lys, Phe, Pro, Ser, Thr, Trp, Tyr or Val;

$X_{14}$ is Ala, Arg, Asn, Asp, Glu, Gln, Gly, His, Ile, Leu, Lys, Phe, Pro, Ser, Thr, Trp, Tyr or Val; and $X_{15}$ is Ala, Arg, Asn, Asp, Glu, Gln, Gly, His, Ile, Leu, Lys, Phe, Pro, Ser, Thr, Trp, Tyr or Val.

TABLE 2

Residue distribution in the TCL2 library

| Residue Position* | WT residues | Distribution in the TCL2 library |
|---|---|---|
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |

TABLE 2-continued

Residue distribution in the TCL2 library

| Residue Position* | WT residues | Distribution in the TCL2 library |
|---|---|---|
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

Subsequently, these libraries were improved by various ways, including building of the libraries on a stabilized Tencon framework (U.S. Pat. No. 8,569,227) that incorporates substitutions E11R/L17A/N46V/E86I (Tencon27; SEQ ID NO:4) when compared to the wild type tencon as well as altering of the positions randomized in the BC and FG loops. Tencon27 is described in Int. Pat. Appl. No. WO2013049275. From this, new libraries designed to randomize only the FG loop of Tencon (library TCL9), or a combination of the BC and FG loops (library TCL7) were generated. These libraries were constructed for use with the cis-display system (Odegrip et al., Proc Natl Acad Sci USA 101: 2806-2810, 2004). The details of this design are shown below:

```
Stabilized Tencon (Tencon27)
                                      (SEQ ID NO: 4)
LPAPKNLVVSRVTEDSARLSWTAPDAAFDSFLIQYQESEKVGEAIVLTVP

GSERSYDLTGLKPGTEYTVSIYGVKGGHRSNPLSAIFTT

TCL7 (randomized FG and BC loops)
                                      (SEQ ID NO: 5)
LPAPKNLVVSRVTEDSARLSWX₁X₂X₃X₄X₅X₆X₇X₈X₉FDSFLIQYQES

EKVGEAIVLTVPGSERSYDLTGLKPGTEYTVSIYGVX₁₀X₁₁X₁₂X₁₃

X₁₄X₁₅X₁₆X₁₇X₁₈X₁₉SNPLSAIFTT;
``` wherein
$X_1, X_2, X_3, X_4, X_5, X_6, X_{10}, X_{11}, X_{12}, X_{13}, X_{14}, X_{15}$ and $X_{16}$ is A, D, E, F, G, H, I, K, L, N, P, Q, R, S, T, V, W or Y; and $X_7, X_8, X_9, X_{17}, X_{18}$ and $X_{19}$, is A, D, E, F, G, H, I, K, L, N, P, Q, R, S, T, V, W, Y or deleted.

```
TCL9 (randomized FG loop)
                                      (SEQ ID NO: 6)
LPAPKNLVVSRVTEDSARLSWTAPDAAFDSFLIQYQESEKVGEAIVLTVP

GSERSYDLTGLKPGTEYTVSIYGV X₁X₂X₃X₄X₅X₆X₇X₈X₉X₁₀X₁₁

X₁₂SNPLSAIFTT;
```

$X_1, X_2, X_3, X_4, X_5, X_6$ and $X_7$, is A, D, E, F, G, H, I, K, L, N, P, Q, R, S, T, V, W or Y; and
$X_8, X_9, X_{10}, X_{11}$ and $X_{12}$ is A, D, E, F, G, H, I, K, L, N, P, Q, R, S, T, V, W, Y or deleted.

For library construction, DNA fragments encoding randomized BC loops (lengths 6-9 positions) or FG loops (lengths 7-12 positions) were synthesized using Slonomics technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31). For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO:9) and Sloning-Rev (SEQ ID NO:10).

The 3' fragment of the library is a constant DNA sequence containing elements for display, including a PspOMI restriction site, the coding region of the repA gene, and the cis- and ori elements. PCR reactions were performed to amplify this fragment using a plasmid (pCR4Blunt) (Invitrogen) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 µg) of 3' repA DNA in the presence of NotI and PspOMI enzyme and T4 ligase at 37° C. overnight. The ligated library product was amplified by using 12 cycles of PCR with oligos POP2250 (SEQ ID NO:11) and DigLigRev (SEQ ID NO:12). For each sub-library, the resulting DNA from 12 PCR reactions were combined and purified by Qiagen spin column. The yield for each sub-library of TCL9 ranged from 32-34 µg.

Construction of FG/BC Loop Libraries (TCL7)

The TCL7 library provides for a library with randomized Tencon BC and FG loops. In this library, BC loops of lengths 6-9 amino acids were mixed combinatorially with randomized FG loops of 7-12 amino acids in length. Synthetic Tencon fragments BC6, BC7, BC8, and BC9 (SEQ ID NOs: 13-16, respectively) were produced to include the Tencon gene encoding for the N-terminal portion of the protein up to and including residue VX such that the BC loop is replaced with either 6, 7, 8, or 9 randomized amino acids. These fragments were synthesized prior to the discovery of L17A, N46V and E831 mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide encoding for amino acid A17 (130mer-L17A, SEQ ID NO:17) was produced by PCR using oligos POP2222ext (SEQ ID NO:18) and LS1114 (SEQ ID NO:19). This was done to include the L17A mutation in the library (CEN5243). Next, DNA fragments encoding for Tencon residues R18-V75 including randomized BC loops were amplified by PCR using BC6, BC7, BC8, or BC9 as a template and oligos LS1115 (SEQ ID NO:20) and LS1117 (SEQ ID NO:21). This PCR step introduced a BsaI site at the 3' end. These DNA fragments were subsequently joined by overlapping PCR using oligos POP2222ext and LS1117 as primers. The resulting PCR product of 240 bp was pooled and purified by Qiagen PCR purification kit. The purified DNA was digested with BsaI-HF and gel purified.

Fragments encoding the FG loop were amplified by PCR using FG7, FG8, FG9, FG10, FG11, and FG12 as templates with oligonucleotides SDG10 (SEQ ID NO:22) and SDG24 (SEQ ID NO:23) to incorporate a BsaI restriction site and N46V and E861 variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID NO:24) and SDG28 SEQ ID NO:25). 7.5 µg of each reaction product were then digested with Not1 and cleaned up with a Qiagen PCR purification column. 5.2 µg of this DNA, was ligated to an equal molar amount of RepA DNA fragment (~14 µg) digested with PspOMI and the product amplified by PCR using oligos POP2222.

Example 2: Generation of Tencon Libraries Having Alternative Binding Surfaces

The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc Natl Acad Sci USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat Biotechnol 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO:7), was designed into Tencon27 scaffold (SEQ ID NO:4).

A full description of the methods used to construct this library is described in US. Pat. Publ. No. 2013/0226834.

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered (Table 3). TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J Mol Biol 377: 1518-1528, 2008) as described in Table 3. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and I86 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 3.

TCL14 library (SEQ ID NO: 7):
LPAPKNLVVSRVTEDSARLSWTAPDAAFDSFX$_1$IX$_2$YX$_3$EX$_4$X$_5$X$_6$X$_7$GE

AIVLTVPGSERSYDLTGLKPGTEYX$_8$VX$_9$IX$_{10}$GVKGGX$_{11}$X$_{12}$SX$_{13}$PL

SAIFTT;

wherein
X$_1$, X$_2$, X$_3$, X$_4$, X$_5$, X$_6$, X$_7$, X$_8$, X$_9$, X$_{10}$, X$_{11}$, X$_{12}$ and X$_{13}$ are A, D, E, F, G, H, I, K, L, N, P, Q, R, S, T, V, W, Y, C or M.

TCL24 Library
(SEQ ID NO: 8)
LPAPKNLVVSRVTEDSARLSWTAPDAAFDSFX$_1$IX$_2$YX$_3$EX$_4$X$_5$X$_6$X$_7$GE

AIX$_8$LX$_9$VPGSERSYDLTGLKPGTEYX$_{10}$VX$_{11}$IX$_{12}$GVKGGX$_{13}$X$_{14}$S

X$_{15}$PLX$_{16}$AX$_{17}$FTT;

wherein
X$_1$, X$_2$, X$_3$, X$_4$, X$_5$, X$_6$, X$_{10}$, X$_{11}$, X$_{12}$, X$_{13}$, X$_{14}$, X$_{15}$, X$_{16}$ and X$_{17}$ are A, D, E, F, G, H, I, K, L, N, P, Q, R, S, T, V, Y or W.

TABLE 3

Amino acid frequency (%) at each randomized position for TCL21, TCL23, and TCL24.

| Amino Acid | TCL19 | TCL21 | TCL23 | TCL24 |
|---|---|---|---|---|
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra library technology (Isogenica) in order to control amino acid distributions. TCL19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., *Proc Natl Acad Sci USA* 101: 2806-2810, 2004) as described above for the loop libraries.

Example 3: Selection of Fibronectin Type III (FN3) Domains that Bind CD137

Panning

FN3 domains specific for human CD137 were selected via CIS-Display (Odegrip et al 2004) using recombinant biotinylated CD137 protein (Fc-fusion protein, R&D Systems 838-4B). For in vitro transcription and translation (ITT), 3 μg of DNA from Centyrin libraries TCL18, TCL19, TCL21, TCL23, and TCL24 (See accompanying library description document) were incubated at 30° C. with 0.1 mM complete amino acids, 1× S30 premix components, and 15 μL of S30 extract (Isogenica) in a total volume of 50 pt. After 1 hour, 375 μL of blocking solution (2% BSA in PBS, Invitrogen) was added and reactions were incubated on a cold block for 15 minutes. Unbound library members were removed by successive washes with TBST and TBS. After washing, DNA was eluted from the target protein by heating to 75° C. for 10 minutes and amplified by PCR using KOD polymerase for further rounds of panning. High affinity binders were isolated by successively lowering the concentration of target CD137 during each round from 400 nM to 100 nM and increasing the washing stringency.

Outputs from the fifth round panning were subjected to four additional rounds of off-rate selection. Library transcription and translation was performed as described above after which, the ITT reactions were incubated with biotinylated recombinant CD137 proteins and captured on neutravidin or streptavidin coated magnetic beads, before being washed in TBST extensively then subsequently washed in 5 uM cold recombinant CD137 protein for 1 hour. The biotinylated target antigen concentration was reduced from 25 nM in rounds 6 and 7 to 2.5 nM in rounds 8 and 9.

Following panning, genes encoding the selected FN3 domains were amplified by PCR, subcloned into a pET vector modified to include a ligase independent cloning site, and transformed into BL21 (DE3) (Stratagene) cells for soluble expression in *E. coli* using standard molecular biology techniques. A gene sequence encoding a C-terminal poly-histidine tag was added to each Centyrin to enable purification and detection. Cultures were grown to an optical density of 0.6-0.8 in TB medium supplemented with 100 μg/mL carbenicillin in 1 mL 96-well blocks at 37° C. before the addition of IPTG to 1 mM, at which point the temperature was reduced to 30° C. Cells were harvested approximately 16 hours later by centrifugation and frozen at −20° C. Cell lysis was achieved by incubating each pellet in 0.6 mL of BugBuster® HT lysis buffer (Novagen EMD Biosciences) supplemented with 0.2 mg/mL lysozyme with shaking at room temperature for 30 minutes.

Biochemical Screening for FN3 Domains that Recombinant CD137

Streptavidin-coated Maxisorp plates (Nunc catalog 436110) were blocked for 1 h in Starting Block T20 (Pierce) and then coated with biotinylated CD137 (using same antigen as in panning) or negative controls (an unrelated Fc-fused recombinant protein and human serum albumin) for 1 h. Plates were rinsed with TBST and diluted lysate was applied to plates for 1 h. Following additional rinses, wells were treated with HRP-conjugated anti-Centyrin antibody (PAB25) for 1 h and then assayed with POD (Roche catalog 11582950001). The DNA from Centyrin lysates with signals at least 10-fold ELISA signal above that of Fc and HSA controls were sequenced resulting in 78 (Table 1) and 102 (Table 2) unique, readable Centyrin sequences isolated from Round 5 and Round 9 screening respectively.

High-Throughput Expression of Anti-CD137 FN3 Domains

102 Isolated clones from unique hits identified by biochemical binding ELISA from Round 9 were combined for growth into 96-well block plate; clones grew in 1 mL cultures (LB media supplemented with kanamycin for selection) at 37° C. overnight with shaking. For protein expression in 96-block plates, 1 mL TB media supplemented with kanamycin was inoculated with 50 uL of the overnight culture and grown at 37° C. with continual shaking at 300 rpm until $OD_{600}$=0.6-1. Once the target OD was reached, protein expression was induced with addition of IPTG to 1 mM; plates were transferred to 30° C. (300 rpm) for overnight growth. Overnight cultures were centrifuged to harvest the cells; bacterial pellets were stored at −80° C. until ready for use. Pellets were lysed with BugBuster® HT lysis buffer (Novagen EMD Biosciences) and His-tagged FN3 domains purified from the clarified lysates with His MultiTrap™ HP plates (GE Healthcare) and eluted in buffer containing 20 mM sodium phosphate, 500 mM sodium chloride, and 250 mM imidazole at pH 7.4. Purified samples were exchanged into PBS pH 7.4 for analysis using PD MultiTrap™ G-25 plates (GE Healthcare).

Size Exclusion Chromatography Analysis

Size exclusion chromatography was used to determine the aggregation state of anti-CD137 FN3 domains. Aliquots (10 μL) of each purified Centyrin were injected onto a Superdex 75 5/150 column (GE Healthcare) at a flow rate of 0.3 mL/min in a mobile phase of PBS pH 7.4. Elution from the column was monitored by absorbance at 280 nm. Tencon protein was included in each run as a control. Agilent ChemStation software was used to analyse the elution profiles. 46 anti-CD137 FN3 domains demonstrated a retention time between 5.2 and 6.4 minutes and only a single SEC peak indicative of monomeric protein.

TABLE 4

Summary of Round 5 Screening Hits

| FN3 Domain | ELISA CD137-Fc (RLU) | ELISA Fc Control (RLU) | ELISA HSA (RLU) | SEQ ID No. |
|---|---|---|---|---|
| ISOP120AR5P1D2 | 907520 | 640 | 640 | 45 |
| ISOP120AR5P1C3 | 927040 | 320 | 240 | 46 |
| ISOP120AR5P1H3 | 769280 | 400 | 480 | 47 |
| ISOP120AR5P1C4 | 708240 | 320 | 240 | 48 |
| ISOP120AR5P1B5 | 500640 | 400 | 320 | 49 |
| ISOP120AR5P1C5 | 425120 | 320 | 160 | 50 |
| ISOP120AR5P1G7 | 568000 | 560 | 480 | 51 |
| ISOP120AR5P1G8 | 541200 | 320 | 320 | 52 |
| ISOP120AR5P1D9 | 636320 | 320 | 320 | 53 |
| ISOP120AR5P1F11 | 714800 | 480 | 320 | 54 |
| ISOP120AR5P1B12 | 864240 | 400 | 480 | 55 |
| ISOP120BR5P1C1 | 437680 | 480 | 480 | 56 |
| ISOP120BR5P1F1 | 541920 | 480 | 480 | 57 |
| ISOP120BR5P1D2 | 360800 | 720 | 240 | 58 |
| ISOP120BR5P1E2 | 882480 | 5680 | 4960 | 59 |
| ISOP120BR5P1F2 | 298800 | 400 | 240 | 60 |
| ISOP120BR5P1D3 | 1138560 | 240 | 400 | 61 |
| ISOP120BR5P1H3 | 874560 | 2000 | 720 | 62 |
| ISOP120BR5P1E4 | 942320 | 320 | 560 | 63 |
| ISOP120BR5P1G4 | 580240 | 480 | 400 | 64 |
| ISOP120BR5P1A5 | 503040 | 640 | 400 | 65 |
| ISOP120BR5P1E6 | 779120 | 320 | 400 | 66 |
| ISOP120BR5P1B7 | 564560 | 400 | 480 | 67 |
| ISOP120BR5P1C7 | 306240 | 880 | 240 | 68 |
| ISOP120BR5P1D8 | 941680 | 480 | 320 | 69 |
| ISOP120BR5P1E8 | 906160 | 480 | 640 | 70 |
| ISOP120BR5P1B9 | 358000 | 560 | 400 | 71 |
| ISOP120BR5P1C9 | 1272800 | 320 | 560 | 72 |
| ISOP120BR5P1D9 | 1224720 | 560 | 560 | 73 |
| ISOP120BR5P1A10 | 573280 | 36160 | 26560 | 74 |
| ISOP120BR5P1G11 | 485440 | 480 | 560 | 75 |
| ISOP120GR5P1E1 | 1022960 | 320 | 320 | 76 |
| ISOP120GR5P1G3 | 1335760 | 320 | 320 | 77 |
| ISOP120GR5P1F5 | 1283680 | 400 | 400 | 78 |
| ISOP120GR5P1H6 | 721440 | 400 | 400 | 79 |
| ISOP120GR5P1E7 | 1130720 | 400 | 480 | 80 |
| ISOP120GR5P1A10 | 626640 | 400 | 400 | 81 |
| ISOP120GR5P1C10 | 501840 | 240 | 480 | 82 |

TABLE 4-continued

Summary of Round 5 Screening Hits

| FN3 Domain | ELISA CD137-Fc (RLU) | ELISA Fc Control (RLU) | ELISA HSA (RLU) | SEQ ID No. |
|---|---|---|---|---|
| ISOP120GR5P1A11 | 1045760 | 480 | 320 | 83 |
| ISOP120GR5P1B11 | 875360 | 320 | 160 | 84 |
| ISOP120GR5P1H11 | 1310560 | 640 | 320 | 85 |
| ISOP120HR5P1E2 | 1319040 | 720 | 2880 | 86 |
| ISOP120HR5P1A3 | 1076480 | 560 | 240 | 87 |
| ISOP120HR5P1B4 | 1185360 | 320 | 320 | 88 |
| ISOP120HR5P1G4 | 346880 | 320 | 480 | 89 |
| ISOP120HR5P1H4 | 630480 | 480 | 320 | 90 |
| ISOP120HR5P1B5 | 519520 | 320 | 240 | 91 |
| ISOP120HR5P1A6 | 1292720 | 640 | 400 | 92 |
| ISOP120HR5P1G6 | 2035360 | 400 | 320 | 93 |
| ISOP120HR5P1A7 | 986800 | 400 | 480 | 94 |
| ISOP120HR5P1D7 | 1104240 | 320 | 320 | 95 |
| ISOP120HR5P1E7 | 363120 | 480 | 480 | 96 |
| ISOP120HR5P1H7 | 1527200 | 640 | 480 | 97 |
| ISOP120HR5P1H8 | 2217040 | 320 | 400 | 98 |
| ISOP120HR5P1D9 | 404720 | 480 | 400 | 99 |
| ISOP120HR5P1F9 | 1177120 | 400 | 400 | 100 |
| ISOP120ER5P1B4 | 499360 | 400 | 400 | 101 |
| ISOP120ER5P1F4 | 536720 | 320 | 400 | 102 |
| ISOP120ER5P1H4 | 1070240 | 480 | 560 | 103 |
| ISOP120ER5P1E5 | 413120 | 240 | 320 | 104 |
| ISOP120ER5P1B6 | 1351600 | 160 | 400 | 105 |
| ISOP120ER5P1C6 | 495360 | 320 | 400 | 106 |
| ISOP120ER5P1H6 | 588560 | 320 | 480 | 107 |
| ISOP120ER5P1A7 | 1114080 | 400 | 400 | 108 |
| ISOP120ER5P1A8 | 1897040 | 400 | 320 | 109 |
| ISOP120ER5P1E10 | 810320 | 720 | 400 | 110 |
| ISOP120ER5P1A11 | 1144160 | 320 | 320 | 111 |
| ISOP120ER5P1B12 | 1441520 | 720 | 800 | 112 |
| ISOP120FR5P1F1 | 1228320 | 480 | 640 | 113 |
| ISOP120FR5P1C2 | 388960 | 240 | 400 | 114 |
| ISOP120FR5P1H5 | 459680 | 400 | 560 | 115 |
| ISOP120FR5P1A6 | 1404240 | 400 | 320 | 116 |
| ISOP120FR5P1H6 | 356880 | 320 | 320 | 117 |
| ISOP120FR5P1D7 | 1178800 | 400 | 480 | 118 |
| ISOP120FR5P1F8 | 1197120 | 240 | 400 | 119 |
| ISOP120FR5P1E9 | 1183360 | 320 | 400 | 120 |
| ISOP120FR5P1E10 | 953040 | 240 | 320 | 121 |
| ISOP120FR5P1A11 | 920080 | 480 | 480 | 122 |

TABLE 5

Summary of Round 9 Screening Hits

| FN3 Domain Clone | ELISA CD137 (RLU) | ELISA Fc Control (RLU) | ELISA HSA (RLU) | SEC Retention Time (min) | SEC Peak Height (mAU) | Monomeric | SEQ ID No. |
|---|---|---|---|---|---|---|---|
| ISOP193AR9P1A11 | 8659280 | 1440 | 320 | No peak | | FALSE | 123 |
| ISOP193AR9P1A6 | 6739840 | 960 | 480 | No peak | | FALSE | 124 |
| ISOP193AR9P1B10 | 8120400 | 1520 | 480 | 5.355 | 84.76 | TRUE | 125 |
| ISOP193AR9P1B12 | 2762240 | 2240 | 1440 | 5.712 | 39.72 | TRUE | 126 |
| ISOP193AR9P1B4 | 5744400 | 960 | 480 | 5.495 | 94.79 | TRUE | 127 |
| ISOP193AR9P1C10 | 7143200 | 3520 | 960 | No peak | | FALSE | 128 |
| ISOP193AR9P1E6 | 4179680 | 1200 | 720 | No peak | | FALSE | 129 |
| ISOP193AR9P1F4 | 3836000 | 1520 | 720 | 5.664 | 80.79 | TRUE | 130 |
| ISOP193AR9P1F9 | 4710240 | 1600 | 560 | 5.317 | 142.48 | TRUE | 131 |
| ISOP193AR9P1G11 | 5892800 | 2240 | 960 | 5.234 | 225.17 | | 132 |
| ISOP193AR9P1G5 | 4022880 | 1120 | 720 | 5.315 | 191.85 | FALSE | 133 |
| ISOP193AR9P1G8 | 4255040 | 1440 | 720 | No peak | 1.40 | FALSE | 134 |
| ISOP193AR9P1H8 | 3716320 | 3040 | 1040 | 5.982 | 36.60 | TRUE | 135 |
| ISOP193BR9P1B10 | 9733920 | 2640 | 1200 | 5.884 | 66.69 | TRUE | 136 |
| ISOP193BR9P1B12 | 6551440 | 14000 | 2880 | No peak | | FALSE | 137 |
| ISOP193BR9P1E6 | 4625840 | 2560 | 560 | 6.326 | 5.13 | FALSE | 138 |
| ISOP193BR9P1G11 | 4988080 | 56880 | 9600 | No peak | | FALSE | 139 |
| ISOP193BR9P1G2 | 6145520 | 15920 | 2160 | No peak | | FALSE | 140 |
| ISOP193BR9P1G3 | 4710400 | 1360 | 640 | 7.974 | 7.68 | FALSE | 141 |
| ISOP193BR9P1G6 | 8092720 | 2640 | 960 | 6.045 | 11.68 | TRUE | 142 |
| ISOP193BR9P1G9 | 3725520 | 1200 | 720 | 6.028 | 4.71 | FALSE | 143 |

TABLE 5-continued

Summary of Round 9 Screening Hits

| FN3 Domain Clone | ELISA CD137 (RLU) | ELISA Fc Control (RLU) | ELISA HSA (RLU) | SEC Retention Time (min) | SEC Peak Height (mAU) | Monomeric | SEQ ID No. |
|---|---|---|---|---|---|---|---|
| ISOP193BR9P1H2 | 3502960 | 11840 | 3280 | 6.055 | 55.87 | FALSE | 144 |
| ISOP193BR9P1H3 | 5257440 | 2080 | 1360 | No peak | | FALSE | 145 |
| ISOP193BR9P1H6 | 8857840 | 8320 | 2880 | 5.787 | 64.85 | FALSE | 146 |
| ISOP193ER9P1A10 | 14863840 | 1120 | 240 | No peak | | FALSE | 147 |
| ISOP193ER9P1A11 | 12781600 | 1200 | 640 | 6.015 | 35.38 | TRUE | 148 |
| ISOP193ER9P1A3 | 14185440 | 3040 | 880 | 5.73 | 136.02 | TRUE | 149 |
| ISOP193ER9P1A4 | 9806400 | 960 | 480 | 5.738 | 61.50 | TRUE | 150 |
| ISOP193ER9P1A8 | 14274800 | 1440 | 400 | 5.892 | 14.52 | TRUE | 151 |
| ISOP193ER9P1B4 | 16089360 | 1600 | 320 | No peak | | FALSE | 152 |
| ISOP193ER9P1B5 | 12675520 | 1200 | 400 | 6.033 | 8.43 | TRUE | 153 |
| ISOP193ER9P1C10 | 8866800 | 2480 | 560 | 5.704 | 179.28 | TRUE | 154 |
| ISOP193ER9P1C4 | 15455120 | 960 | 320 | 6.032 | 18.18 | TRUE | 155 |
| ISOP193ER9P1C8 | 16680560 | 1040 | 400 | 5.862 | 19.39 | TRUE | 156 |
| ISOP193ER9P1C9 | 14280160 | 880 | 560 | 5.668 | 20.02 | TRUE | 157 |
| ISOP193ER9P1D4 | 16022720 | 1120 | 480 | 5.843 | 22.38 | TRUE | 158 |
| ISOP193ER9P1D7 | 10954000 | 1680 | 400 | 5.92 | 80.79 | TRUE | 159 |
| ISOP193ER9P1E1 | 14972480 | 1200 | 560 | 5.755 | 18.97 | TRUE | 160 |
| ISOP193ER9P1E2 | 15691600 | 1040 | 560 | 6.296 | 20.36 | TRUE | 161 |
| ISOP193ER9P1E4 | 12645760 | 1680 | 480 | 5.762 | 118.21 | TRUE | 162 |
| ISOP193ER9P1E8 | 16401200 | 880 | 480 | 5.699 | 16.07 | TRUE | 163 |
| ISOP193ER9P1F11 | 11182240 | 2240 | 400 | No peak | | FALSE | 164 |
| ISOP193ER9P1F7 | 15148960 | 1200 | 480 | 5.856 | 7.39 | TRUE | 165 |
| ISOP193ER9P1F9 | 14980400 | 1840 | 400 | 7.819 | 4.92 | FALSE | 166 |
| ISOP193ER9P1G11 | 14840160 | 1440 | 560 | 5.859 | 17.01 | TRUE | 167 |
| ISOP193ER9P1G2 | 7192960 | 1680 | 720 | 5.677 | 24.15 | TRUE | 168 |
| ISOP193ER9P1G4 | 13819760 | 1440 | 320 | 5.979 | 2.54 | FALSE | 169 |
| ISOP193ER9P1G5 | 15073600 | 1440 | 400 | No peak | | FALSE | 170 |
| ISOP193ER9P1G9 | 12900320 | 1280 | 400 | 5.781 | 6.70 | TRUE | 171 |
| ISOP193ER9P1H11 | 2080000 | 1360 | 640 | 5.991 | 39.63 | TRUE | 172 |
| ISOP193ER9P1H2 | 5183360 | 1360 | 560 | 5.833 | 53.11 | TRUE | 173 |
| ISOP193ER9P1H3 | 10515760 | 1520 | 400 | 6.073 | 7.45 | FALSE | 174 |
| ISOP193FR9P1A11 | 5784000 | 3520 | 880 | No peak | | FALSE | 175 |
| ISOP193FR9P1A5 | 9072080 | 95120 | 26240 | 6.033 | 8.14 | TRUE | 176 |
| ISOP193FR9P1C1 | 14116720 | 36800 | 8160 | 5.866 | 3.99 | FALSE | 177 |
| ISOP193FR9P1C5 | 8660800 | 79280 | 19200 | 6.377 | 20.91 | TRUE | 178 |
| ISOP193FR9P1C9 | 12306480 | 21040 | 4000 | 7.257 | 5.36 | FALSE | 179 |
| ISOP193FR9P1D1 | 8132800 | 1680 | 640 | No peak | | FALSE | 180 |
| ISOP193FR9P1D5 | 6046880 | 51680 | 10800 | 5.948 | 4.84 | TRUE | 181 |
| ISOP193FR9P1D7 | 2195360 | 15040 | 2640 | 6.077 | 1.98 | FALSE | 182 |
| ISOP193FR9P1E1 | 11602480 | 2000 | 880 | 5.84 | 28.48 | FALSE | 183 |
| ISOP193FR9P1E10 | 2051600 | 133120 | 31040 | 5.9 | 46.84 | TRUE | 184 |
| ISOP193FR9P1F8 | 8573040 | 25680 | 5040 | 5.652 | 3.10 | FALSE | 185 |
| ISOP193FR9P1G10 | 8908880 | 2480 | 880 | 6.864 | 2.25 | FALSE | 186 |
| ISOP193FR9P1G11 | 10788560 | 60640 | 10960 | 5.945 | 5.46 | TRUE | 187 |
| ISOP193FR9P1G2 | 7864240 | 2560 | 880 | No peak | | FALSE | 188 |
| ISOP193FR9P1G4 | 13950480 | 1840 | 640 | 5.834 | 5.47 | TRUE | 189 |
| ISOP193FR9P1G7 | 5500720 | 42320 | 10960 | 5.897 | 9.89 | TRUE | 190 |
| ISOP193FR9P1G8 | 14458880 | 25120 | 5040 | 5.874 | 5.87 | FALSE | 191 |
| ISOP193FR9P1G9 | 12761120 | 33600 | 6800 | 6.413 | 6.02 | FALSE | 192 |
| ISOP193FR9P1H6 | 11204000 | 88320 | 23040 | 5.712 | 7.91 | TRUE | 193 |
| ISOP193FR9P1H9 | 2420400 | 2000 | 800 | 5.987 | 23.27 | TRUE | 194 |
| ISOP193GR9P1A7 | 2153840 | 1040 | 480 | 5.634 | 10.89 | TRUE | 195 |
| ISOP193GR9P1B3 | 3457040 | 880 | 320 | 5.768 | 3.78 | FALSE | 196 |
| ISOP193GR9P1E10 | 10452960 | 1360 | 480 | No peak | | FALSE | 197 |
| ISOP193GR9P1F6 | 9846640 | 1360 | 400 | 5.656 | 4.72 | FALSE | 198 |
| ISOP193GR9P1F7 | 3480640 | 880 | 400 | 5.712 | 2.95 | FALSE | 199 |
| ISOP193GR9P1G9 | 3052480 | 960 | 480 | 5.645 | 7.32 | TRUE | 200 |
| ISOP193GR9P1H2 | 5314000 | 1360 | 640 | No peak | | FALSE | 201 |
| ISOP193HR9P1A10 | 12663280 | 5680 | 1520 | No peak | | FALSE | 202 |
| ISOP193HR9P1A11 | 16644800 | 28320 | 4240 | No peak | | FALSE | 203 |
| ISOP193HR9P1A5 | 14895120 | 6080 | 2080 | No peak | | FALSE | 204 |
| ISOP193HR9P1A6 | 14635040 | 24960 | 5120 | No peak | | FALSE | 205 |
| ISOP193HR9P1A7 | 14786080 | 48880 | 12640 | 6.013 | 9.21 | TRUE | 206 |
| ISOP193HR9P1B11 | 16579440 | 14960 | 4080 | No peak | | FALSE | 207 |
| ISOP193HR9P1B7 | 16384560 | 12960 | 2240 | No peak | | FALSE | 208 |
| ISOP193HR9P1C7 | 3436800 | 71360 | 10000 | 5.69 | 2.15 | FALSE | 209 |
| ISOP193HR9P1C8 | 18185520 | 1360 | 560 | 6.475 | 4.54 | TRUE | 210 |
| ISOP193HR9P1D11 | 14160720 | 48720 | 6240 | 5.936 | 5.80 | TRUE | 211 |
| ISOP193HR9P1D8 | 6271280 | 10880 | 2640 | 5.79 | 4.93 | TRUE | 212 |
| ISOP193HR9P1E2 | 9022400 | 13120 | 3840 | 5.801 | 4.22 | FALSE | 213 |
| ISOP193HR9P1E3 | 17767600 | 1120 | 640 | 6.564 | 3.11 | FALSE | 214 |
| ISOP193HR9P1E6 | 11258560 | 20080 | 3040 | 5.859 | 3.13 | FALSE | 215 |
| ISOP193HR9P1E8 | 16318560 | 3120 | 1520 | No peak | | FALSE | 216 |

TABLE 5-continued

Summary of Round 9 Screening Hits

| FN3 Domain Clone | ELISA CD137 (RLU) | ELISA Fc Control (RLU) | ELISA HSA (RLU) | SEC Retention Time (min) | SEC Peak Height (mAU) | Monomeric | SEQ ID No. |
|---|---|---|---|---|---|---|---|
| ISOP193HR9P1F10 | 15810240 | 1280 | 960 | No peak | | FALSE | 217 |
| ISOP193HR9P1F8 | 16086000 | 31280 | 6080 | No peak | | FALSE | 218 |
| ISOP193HR9P1G10 | 15586960 | 1360 | 800 | 6.226 | 2.97 | FALSE | 219 |
| ISOP193HR9P1G4 | 17180000 | 960 | 560 | 6.293 | 2.54 | FALSE | 220 |
| ISOP193HR9P1G5 | 15137440 | 24160 | 3360 | 5.913 | 9.58 | TRUE | 221 |
| ISOP193HR9P1G6 | 11499680 | 8160 | 1200 | No peak | | FALSE | 222 |
| ISOP193HR9P1H10 | 14818080 | 43920 | 10080 | 6.107 | 2.19 | FALSE | 223 |
| ISOP193HR9P1H7 | 4604800 | 49840 | 13680 | 6.035 | 1.81 | FALSE | 224 |

Example 4: Characterization of Fibronectin Type III (FN3) Domains that Bind CD137

Fluorescence-Activated Cell Sorting (FACS)

Cell surface binding was analyzed via flow cytometry. Cenyrins were prepared at a maximal concentration of 500 nM in the presence of 125 nM anti His-mIgG1 antibody and then serially diluted in PBS/1% FCS buffer. Samples were then applied to approx 100 000 CHO-K1 cells expressing the extracellular domain of human CD137 on their surface. Unbound Centyrin/Antibody complexes were washed away and bound FN3 domains were detected by the addition of goat anti mouse-FITC labeled antibody. Samples were then acquired by flow cytometry. Subsequently, Mean fluorescence intensity was plotted against the log Centyrin concentration and EC50 values were calculated by nonlinear regression using GraphPad Prism.

Binding Analysis with Biacore

For selected FN3 domains, binding to recombinant CD137-Fc was evaluated using surface plasmon resonance (Biacore T100). For each cycle approximately 500 RU of recombinant human CD137-Fc-IgG1 was captured via an anti human IgG immobilized on the surface of a CM5 chip. Once CD137-Fc protein was captured, increasing concentrations of Centyrin candidates were injected for 120 s and dissociation was then analyzed for 240 s. A flow cell immobilized with just the anti human IgG1 antibody served as reference flow cell. Kd values were subsequently extrapolated using a 1:1 kinetic binding model (BiaEvaluation software).

TABLE 6

Centyrin binding analysis by FACS and Biacore

| Centyrin Clone | EC50 FACS (nM) | Biacore (Kd) |
|---|---|---|
| ISOP193AR9P1B4 | 13.93 | n.d. |
| ISOP193AR9P1F4 | n.a. | n.d. |
| ISOP193AR9P1H8 | n.a. | n.d. |
| ISOP193AR9P1F9 | 218 | n.d. |
| ISOP193AR9P1B10 | 1.205 | n.d. |
| ISOP193AR9P1G11 | 10.48 | n.d. |
| ISOP193AR9P1B12 | n.a. | n.d. |
| ISOP193BR9P1G6 | n.a. | n.d. |
| ISOP193BR9P1B10 | 134 | n.d. |
| ISOP193GR9P1A7 | 605.6 | n.d. |
| ISOP193GR9P1G9 | n.a. | n.d. |
| ISOP193GR9P1F11 | 508.9 | n.d. |
| ISOP193HR9P1C8 | 3.268 | n.d. |
| ISOP193ER9P1E1 | 12.55 | 1.059E-08 |
| ISOP193ER9P1E2 | 15.31 | 1.094E-08 |
| ISOP193ER9P1G2 | 22.94 | 6.563E-08 |
| ISOP193ER9P1H2 | 27.46 | n.d. |
| ISOP193ER9P1A3 | 10.22 | 8.3E-09 |
| ISOP193ER9P1A4 | 27.1 | 1.172E-07 |
| ISOP193ER9P1C4 | 18.91 | 1.31E-08 |
| ISOP193ER9P1D4 | 12.86 | 9.552E-09 |
| ISOP193ER9P1E4 | 278.7 | n.d. |
| ISOP193ER9P1B5 | 7.342 | n.d. |
| ISOP193ER9P1D5 | 29.61 | n.d. |
| ISOP193ER9P1C7 | 19.07 | n.d. |
| ISOP193ER9P1F7 | 24.99 | n.d. |
| ISOP193ER9P1A8 | 16.96 | n.d. |
| ISOP193ER9P1C8 | 12.43 | n.d. |
| ISOP193ER9P1E8 | 17.67 | n.d. |
| ISOP193ER9P1C9 | 14.1 | 2.51E-08 |
| ISOP193ER9P1G9 | 15.26 | 5.986E-08 |
| ISOP193ER9P1C10 | 31.01 | 1.077E-07 |
| ISOP193ER9P1A11 | 10.56 | n.d. |
| ISOP193ER9P1G11 | 18.69 | n.d. |
| ISOP193ER9P1H11 | 184.5 | n.d. |
| ISOP193ER9P1B12 | 19.87 | n.d. |
| ISOP193FR9P1G4 | 26.93 | n.d. |
| ISOP193FR9P1H9 | 72.75 | n.d. |

SEQUENCES

SEQ ID NO: 1 = Original Tencon Sequence
LPAPKNLVVSEVTEDSLRLSWTAPDAAFDSFLIQYQESEKVGEAINLTVP
GSERSYDLTGLKPGTEYTVSIYGVKGGHRSNPLSAEFTT SEQ ID NO: 2 = TCL1 library
LPAPKNLVVSEVTEDSLRLSWTAPDAAFDSFLIQYQESEKVGEAINLTVP
GSERSYDLTGLKPGTEYTVSIYGV(X)$_{7-12}$PLSAEFTT;
wherein
$X_1$, $X_2$, $X_3$, $X_4$, $X_5$, $X_6$, $X_7$ is any amino acid; and
$X_8$, $X_9$, $X_{10}$, $X_{11}$ and $X_{12}$ are any amino acid or deleted SEQ ID NO: 3 = TCL2 library
LPAPKNLVVSEVTEDSLRLSWX$_1$X$_2$X$_3$X$_4$X$_5$X$_6$X$_7$X$_8$SFLIQYQESEKVG
EAINLTVPGSERSYDLTGLKPGTEYTVSIYGVX$_9$X$_{10}$X$_{11}$X$_{12}$X$_{13}$SX$_{14}$
X$_{15}$LSAEFTT;
wherein
$X_1$ is Ala, Arg, Asn, Asp, Glu, Gln, Gly, His, Ile, Leu, Lys, Phe, Pro, Ser, Thr, Trp, Tyr or Val;
$X_2$ is Ala, Arg, Asn, Asp, Glu, Gln, Gly, His, Ile, Leu, Lys, Phe, Pro, Ser, Thr, Trp, Tyr or Val;
$X_3$ Ala, Arg, Asn, Asp, Glu, Gln, Gly, His, Ile, Leu, Lys, Phe, Pro, Ser, Thr, Trp, Tyr or Val;
$X_4$ is Ala, Arg, Asn, Asp, Glu, Gln, Gly, His, Ile, Leu, Lys, Phe, Pro, Ser, Thr, Trp, Tyr or Val;
$X_5$ is Ala, Arg, Asn, Asp, Glu, Gln, Gly, His, Ile,

SEQUENCES

Leu, Lys, Phe, Pro, Ser, Thr, Trp, Tyr or Val;
$X_6$ is Ala, Arg, Asn, Asp, Glu, Gln, Gly, His, Ile, Leu, Lys, Phe, Pro, Ser, Thr, Trp, Tyr or Val;
$X_7$ is Phe, Ile, Leu, Val or Tyr;
$X_8$ is Asp, Glu or Thr;
$X_9$ is Ala, Arg, Asn, Asp, Glu, Gln, Gly, His, Ile, Leu, Lys, Phe, Pro, Ser, Thr, Trp, Tyr or Val;
$X_{10}$ is Ala, Arg, Asn, Asp, Glu, Gln, Gly, His, Ile, Leu, Lys, Phe, Pro, Ser, Thr, Trp, Tyr or Val;
$X_{11}$ is Ala, Arg, Asn, Asp, Glu, Gln, Gly, His, Ile, Leu, Lys, Phe, Pro, Ser, Thr, Trp, Tyr or Val;
$X_{12}$ is Ala, Arg, Asn, Asp, Glu, Gln, Gly, His, Ile, Leu, Lys, Phe, Pro, Ser, Thr, Trp, Tyr or Val;
$X_{13}$ is Ala, Arg, Asn, Asp, Glu, Gln, Gly, His, Ile, Leu, Lys, Phe, Pro, Ser, Thr, Trp, Tyr or Val;
$X_{14}$ is Ala, Arg, Asn, Asp, Glu, Gln, Gly, His, Ile, Leu, Lys, Phe, Pro, Ser, Thr, Trp, Tyr or Val; and
$X_{15}$ is Ala, Arg, Asn, Asp, Glu, Gln, Gly, His, Ile, Leu, Lys, Phe, Pro, Ser, Thr, Trp, Tyr or Val.

SEQ ID NO: 4 = Stabilized Tencon
LPAPKNLVVSRVTEDSARLSWTAPDAAFDSFLIQYQESEKVGEAIVLTVP
GSERSYDLTGLKPGTEYTVSIYGVKGGHRSNPLSAIFTT SEQ ID NO: 5 = TCL7 (FG and BC loops)
LPAPKNLVVSRVTEDSARLSWX$_1$X$_2$X$_3$X$_4$X$_5$X$_6$X$_7$X$_8$X$_9$FDSFLIQYQES
EKVGEAIVLTVPGSERSYDLTGLKPGTEYTVSIYGVX$_{10}$X$_{11}$X$_{12}$X$_{13}$
X$_{14}$X$_{15}$X$_{16}$X$_{17}$X$_{18}$X$_{19}$SNPLSAIFTT;
wherein
$X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ are A, D, E, F, G, H, I, K, L, N, P, Q, R, S, T, V, W or Y;
and
$X_7$, $X_8$, $X_9$, $X_{17}$, $X_{18}$ and $X_{19}$, are A, D, E, F, G, H, I, K, L, N, P, Q, R, S, T, V, W, Y or deleted SEQ ID NO: 6 = TCL9 (FG loop)
LPAPKNLVVSRVTEDSARLSWTAPDAAFDSFLIQYQESEKVGEAIVLTVP
GSERSYDLTGLKPGTEYTVSIYGVX$_1$X$_2$X$_3$X$_4$X$_5$X$_6$X$_7$X$_8$X$_9$X$_{10}$X$_{11}$
X$_{12}$SNPLSAIFTT;
wherein
$X_1$, $X_2$, $X_3$, $X_4$, $X_5$, $X_6$ and $X_7$, is A, D, E, F, G, H, I, K, L, N, P, Q, R, S, T, V, W or Y;
and
$X_8$, $X_9$, $X_{10}$, $X_{11}$ and $X_{12}$ is A, D, E, F, G, H, I, K, L, N, P, Q, R, S, T, V, W, Y or deleted.

TCL14 library (SEQ ID NO: 7):
LPAPKNLVVSRVTEDSARLSWTAPDAAFDSFX$_1$IX$_2$YX$_3$EX$_4$X$_5$X$_6$X$_7$GE
AIVLTVPGSERSYDLTGLKPGTEYX$_8$VX$_9$IX$_{10}$GVKGGX$_{11}$X$_{12}$SX$_{13}$PL
SAIFTT;
wherein
$X_1$, $X_2$, $X_3$, $X_4$, $X_5$, $X_6$, $X_7$, $X_8$, $X_9$, $X_{10}$, $X_{11}$, $X_{12}$ and $X_{13}$ are A, D, E, F, G, H, I, K, L, N, P, Q, R, S, T, V, W, Y, C or M.

TCL24 Library (SEQ ID NO: 8):
LPAPKNLVVSRVTEDSARLSWTAPDAAFDSFX$_1$IX$_2$YX$_3$EX$_4$X$_5$X$_6$X$_7$GE
AIX$_8$LX$_9$VPGSERSYDLTGLKPGTEYX$_{10}$VX$_{11}$IX$_{12}$GVKGGX$_{13}$X$_{14}$S
X$_{15}$PLX$_{16}$AX$_{17}$FTT;
wherein
$X_1$, $X_2$, $X_3$, $X_4$, $X_5$, $X_6$, $X_{10}$, $X_{11}$, $X_{12}$, $X_{13}$, $X_{14}$, $X_{15}$, $X_{16}$ and $X_{17}$ are A, D, E, F, G, H, I, K, L, N, P, Q, R, S, T, V, Y or W.

SEQ ID NO: 9 = Sloning-FOR
GTGACACGGCGGTTAGAAC

SEQ ID NO: 10 = Sloning-REV
GCCTTTGGGAAGCTTCTAAG

SEQ ID NO: 11 = POP2250
CGGCGGTTAGAACGCGGCTACAATTAATAC

SEQ ID NO: 12 = DigLigRev
CATGATTACGCCAAGCTCAGAA

SEQ ID NO: 13 = BC9
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTGAAGTTACCGAAGACTCTCTGCGTCTGTCTTGGNNN
NNNNNNNNNNNNNNNNNNNNNNNNTTYGACTCTTTCCTGATCCAGTACCA
GGAATCTGAAAAAGTTGGTGAAGCGATCAACCTGACCGTTCCGGGTTCTG
AACGTTCTTACGACCTGACCGGTCTGAAACCGGGTACCGAATACACCGTT
TCTATCTACGGTGTTCTTAGAAGCTTCCCAAAGGC

SEQ ID NO: 14 = BC8
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTGAAGTTACCGAAGACTCTCTGCGTCGTGTCTTGGNNN
NNNNNNNNNNNNNNNNNNNNTTYGACTCTTTCCTGATCCAGTACCAGGA
ATCTGAAAAAGTTGGTGAAGCGATCAACCTGACCGTTCCGGGTTCTGAAC
GTTCTTACGACCTGACCGGTCTGAAACCGGGTACCGAATACACCGTTTCT
ATCTACGGTGTTCTTAGAAGCTTCCCAAAGGC

SEQ ID NO: 15 = BC7
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTGAAGTTACCGAAGACTCTCTGCGTCTGTCTTGGNNN
NNNNNNNNNNNNNNNNNTTYGACTCTTTCCTGATCCAGTACCAGGAATC
TGAAAAAGTTGGTGAAGCGATCAACCTGACCGTTCCGGGTTCTGAACGTT
CTTACGACCTGACCGGTCTGAAACCGGGTACCGAATACACCGTTTCTATC
TACGGTGTTCTTAGAAGCTTCCCAAAGGC

SEQ ID NO: 16 = BC6
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTGAAGTTACCGAAGACTCTCTGCGTCTGTCTTGGNNN
NNNNNNNNNNNNNNNTTYGACTCTTTCCTGATCCAGTACCAGGAATCTGA
AAAAGTTGGTGAAGCGATCAACCTGACCGTTCCGGGTTCTGAACGTTCTT
ACGACCTGACCGGTCTGAAACCGGGTACCGAATACACCGTTTCTATCTAC
GGTGTTCTTAGAAGCTTCCCAAAGGC

SEQ ID NO: 17 = 130 mer-L17A
CGGCGGTTAGAACGCGGCTACAATTAATACATAACCCCATCCCCCTGTTG
ACAATTAATCATCGGCTCGTATAATGTGTGGAATTGTGAGCGGATAACAA
TTTCACACAGGAAACAGGATCTACCATGCTG SEQ ID NO: 18 = POP222ext
CGG CGG TTA GAA CGC GGC TAC AAT TAA TAC SEQ ID NO: 19 = LS1114
CCA AGA CAG ACG GGC AGA GTC TTC GGT AAC GCG AGA
AAC AAC CAG GTT TTT CGG CGC CGG CAG CATGGT AGA
TCC TGT TTC

SEQ ID NO: 20 = LS1115
CCG AAG ACT CTG CCC GTC TGT CTTGG

SEQ ID NO: 21 = LS1117
CAG TGG TCT CAC GGA TTC CTG GTA CTG GAT CAG AAA
AGA GTC GAA

SEQ ID NO: 22 = SDG10
CATGCGGTCTCTTCCGAAAAAGTTGGTGAAGCGATCGTCCTGACCGTTCC
GGGT

SEQ ID NO: 23 = SDG24
GGTGGTGAAGATCGCAGACAGCGGGTTAG

SEQ ID NO: 24 = POP2222
CGGCGGTTAGAACGCGGCTAC

SEQUENCES

SEQ ID NO: 25 = SDG28
AAGATCAGTTGCGGCCGCTAGACTAGAACCGCTGCCACCGCCGGTGGTGA
AGATCGCAGAC

SEQ ID NO: 26 = FG12
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTCGCGTTACCGAAGACTCTGCGCGTCTGTCTTGGACC
GCGCCGGACGCGGCGTTCGACTCTTTCCTGATCCAGTACCAGGAATCTGA
AAAAGTTGGTGAAGCGATCGTGCTGACCGTTCCGGGTTCTGAACGTTCTT
ACGACCTGACCGGTCTGAAACCGGGTACCGAATACACCGTTTCTATCTAC
GGTGTTNNNNNNNNNNNNNNNNNNNNNNNNNNNNNNNNNTCTAACCCC
GCTGTCTGCGATCTTCACCACCGGCGGTCACCATCACCATCACCATGGCA
GCGGTTCTAGTCTAGCGGCCGCAACTGATCTTGGC

SEQ ID NO: 27 = FG11
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTCGCGTTACCGAAGACTCTGCGCGTCTGTCTTGGACC
GCGCCGGACGCGGCGTTCGACTCTTTCCTGATCCAGTACCAGGAATCTGA
AAAAGTTGGTGAAGCGATCGTGCTGACCGTTCCGGGTTCTGAACGTTCTT
ACGACCTGACCGGTCTGAAACCGGGTACCGAATACACCGTTTCTATCTAC
GGTGTTNNNNNNNNNNNNNNNNNNNNNNNNNNNNNNNNTCTAACCCGCT
GTCTGCGATCTTCACCACCGGCGGTCACCATCACCATCACCATGGCAGCG
GTTCTAGTCTAGCGGCCGCAACTGATCTTGGC

SEQ ID NO: 28 = FG10
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTCGCGTTACCGAAGACTCTGCGCGTCTGTCTTGGACC
GCGCCGGACGCGGCGTTCGACTCTTTCCTGATCCAGTACCAGGAATCTGA
AAAAGTTGGTGAAGCGATCGTGCTGACCGTTCCGGGTTCTGAACGTTCTT
ACGACCTGACCGGTCTGAAACCGGGTACCGAATACACCGTTTCTATCTAC
GGTGTTNNNNNNNNNNNNNNNNNNNNNNNNNNNNNNNTCTAACCCGCTGTC
TGCGATCTTCACCACCGGCGGTCACCATCACCATCACCATGGCAGCGGTT
CTAGTCTAGCGGCCGCAACTGATCTTGGC

SEQ ID NO: 29 = FG9
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTCGCGTTACCGAAGACTCTGCGCGTCTGTCTTGGACC
GCGCCGGACGCGGCGTTCGACTCTTTCCTGATCCAGTACCAGGAATCTGA
AAAAGTTGGTGAAGCGATCGTGCTGACCGTTCCGGGTTCTGAACGTTCTT
ACGACCTGACCGGTCTGAAACCGGGTACCGAATACACCGTTTCTATCTAC
GGTGTTNNNNNNNNNNNNNNNNNNNNNNNNNNNNTCTAACCCGCTGTCTGC
GATCTTCACCACCGGCGGTCACCATCACCATCACCATGGCAGCGGTTCTA
GTCTAGCGGCCGCAACTGATCTTGGC

SEQ ID NO: 30 = FG8
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTCGCGTTACCGAAGACTCTGCGCGTCTGTCTTGGACC
GCGCCGGACGCGGCGTTCGACTCTTTCCTGATCCAGTACCAGGAATCTGA
AAAAGTTGGTGAAGCGATCGTGCTGACCGTTCCGGGTTCTGAACGTTCTT
ACGACCTGACCGGTCTGAAACCGGGTACCGAATACACCGTTTCTATCTAC
GGTGTTNNNNNNNNNNNNNNNNNNNNNNNNNNNTCTAACCCGCTGTCTGCGAT
CTTCACCACCGGCGGTCACCATCACCATCACCATGGCAGCGGTTCTAGTC
TAGCGGCCGCAACTGATCTTGGC

SEQ ID NO: 31 = FG7
GTGACACGGCGGTTAGAACGCGGCTACAATTAATACATAACCCCATCCCC
CTGTTGACAATTAATCATCGGCTCGTATAATGTGTGGAATTGTGAGCGGA
TAACAATTTCACACAGGAAACAGGATCTACCATGCTGCCGGCGCCGAAAA
ACCTGGTTGTTTCTCGCGTTACCGAAGACTCTGCGCGTCTGTCTTGGACC
GCGCCGGACGCGGCGTTCGACTCTTTCCTGATCCAGTACCAGGAATCTGA
AAAAGTTGGTGAAGCGATCGTGCTGACCGTTCCGGGTTCTGAACGTTCTT
ACGACCTGACCGGTCTGAAACCGGGTACCGAATACACCGTTTCTATCTAC
GGTGTTNNNNNNNNNNNNNNNNNNNNNNNNNNTCTAACCCGCTGTCTGCGATCTT
CACCACCGGCGGTCACCATCACCATCACCATGGCAGCGGTTCTAGTCTAG
CGGCCGCAACTGATCTTGGC

TABLE 7

FN3 Domains, Linkers, and Albumin variant

| Clone | SEQ ID NO: | AA Sequence |
|---|---|---|
| 3rd FN3 domain of tenascin C (TN3 | 32 | DAPSQIEVKDVTDTTALITWFKPLAEIDGIELTY GIKDVPGDRTTIDLTEDENQYSIGNLKPDTEYEV SLISRRGDMSSNPAKETFTT |
| Fibcon | 33 | LDAPTDLQVTNVTDTSITVSWTPPSATITGYRIT YTPSNGPGEPKELTVPPSSTSVTITGLTPGVEYV VSLYALKDNQESPPLVGTQTT |
| 10th FN3 domain of fibronectin | 34 | VSDVPRDLEVVAATPTSLLISWDAPAVTVRYYRI TYGETGGNSPVQEFTVPGSKSTATISGLKPGVDY TITVYAVTGRGDSPASSKPISINYRT |
| Linker | 35 | GSGS |
| Linker | 36 | GGGSGGGS |
| Linker | 37 | GGGGSGGGGSGGGGSGGGGSGGGGS |
| Linker | 38 | APAP |
| Linker | 39 | APAPAPAPAP |
| Linker | 40 | APAPAPAPAPAPAPAPAP |
| Linker | 41 | APAPAPAPAPAPAPAPAPAPAPAPAPAPAPAPAP APAPAP |
| Linker | 42 | EAAAKEAAAKEAAAKEAAAKEAAAKAAA |
| Albumin variant | 43 | DAHKSEVAHRFKDLGEENFKALVLIAFAQYLQQS PFEDHVKLVNEVTEFAKTCVADESAENCDKSLHT LFGDKLCTVATLRETYGEMADCCAKQEPERNECF LQHKDDNPNLPRLVRPEVDVMCTAFHDNEETFLK KYLYEIARRHPYFYAPELLFFAKRYKAAFTECCQ AADKAACLLPKLDELRDEGKASSAKQRLKCASLQ KFGERAFKAWAVARLSQRFPKAEFAEVSKLVTDL TKVHTECCHGDLLECADDRADLAKYICEDLPSLA NQDSISSKLKECCEKPLLEKSHCIAEVENDEMPA ADFVESKDVCKNYAEAKDVFLGMFLYEYARRHPD YSVVLLLRLAKTYETTLEKCCAAADPHECYAKVF DEFKPLVEEPQNLIKQNCELFEQLGEYKFQNALL VRYTKKVPQVSTPTLVEVSRNLGKVGSKCCKHPE AKRMPCAEDYLSVVLNQLCVLHEKTPVSDRVTKC CTESLVNRRPCFSALEVDETYVPKEFNAETFTFH ADICTLSEKERQIKKQTALVELVKHKPKATKEQL KAVMDDFAAFVEKCCKADDKETCFAEEGKKLVAA SQAALGL |

SEQ ID NO: 44 = human CD137
MGNSCYNIVATLLLVLNFERTRSLQDPCSNCPAGTFCDNNRNQICSPCPP

NSFSSAGGQRTCDICRQCKGVFRTRKECSSTSNAECDCTPGFHCLGAGCS

MCEQDCKQGQELTKKGCKDCCFGTFNDQKRGICRPWTNCSLDGKSVLVNG

TKERDVVCGPSPADLSPGASSVTPPAPAREPGHSPQIISFFLALTSTALL

FLLFFLTLRFSVVKRGRKKLLYIFKQPFMRPVQTTQEEDGCSCRFPEEEE

GGCEL

CD137 binding fibronectin type III domains
SEQ ID NO: 45 ISOP120AR5P1D2
LPAPKNLVVSRVTEDSARLSWDFAYFKFDSFLIQYQESEKVGEAIVLTVP

GSERSYDLTGLKPGTEYTVSIYGVGRFYTVYYSNPLSAIFTT

SEQ ID NO: 46 ISOP120AR5P1C3
LPAPKNLVVSRVTEDSARLSWSPVDADFTFDSFLIQYQESEKVGEAIVLT
VPGSERSYDLTGLKPGTEYTVSIYGVGRHYTVYDSNPLSAIFTT

SEQ ID NO: 47 ISOP120AR5P1H3
LPAPKNLVVSRVTEDSARLSWKWISHEPLEFDSFLIQYQESEKVGEAIVL
TVPGSERSYDLTGLKPGTEYTVSIYGVGRHYTVYDSNPLSAIFTT

SEQ ID NO: 48 ISOP120AR5P1C4
LPAPKNLVVSRVTEDSARLSWAFQWHIFDSFLIQYQESEKVGEAIVLTVP
GSERSYDLTGLKPGTEYTVSIYGVGQPYTVYDSNPLSAIFTT

SEQ ID NO: 49 ISOP120AR5P1B5
LPAPKNLVVSRVTEDYARLSWKYGEHIIWFDSFLIQYQESEKVGEAIVLT
VPGSERSYDLTGLKPGTEYTVSIYGVKGQHDHDSNPLSAIFTT

SEQ ID NO: 50 ISOP120AR5P1C5
LPAPKNLVVSRVTEDSARLSWTLPNIHFDSFLIQYQESEKVGEAIVLTVP
GSERSYDLTGLKPGTEYTVSIYGVGRHYTVYDSNPLSAIFTT

SEQ ID NO: 51 ISOP120AR5P1G7
LPAPKNLVVSRVTEDSARLSWSQHYLSPIPFDSFLIQYQESEKVGEAIVL
TVPGSERSYDLTGLKPGTEYTVSIYGVGRHYTVYDSNPLSAIFTT

SEQ ID NO: 52 ISOP120AR5P1G8
LPAPKNLVVSRVTEDSARLSWHATFGDPFDSFLIQYQESEKVGEAIVLTV
PGSERSYDLTGLKPGTEYTVSIYGVGRHYTVYDSNPLSAIFTT

SEQ ID NO: 53 ISOP120AR5P1D9
LPAPKNLVVSRVTEDSARLSWNTDWVHTFDSFLIQYQESEKVGEAIVLTV
PGSERSYDLTGLKPGTEYTVSIYGVGRHYTVYDSNPLSAIFTT

SEQ ID NO: 54 ISOP120AR5P1F11
LPAPKNLVVSRVTEDSARLSWTNEQITKYGFDSFLIQYQESEKVGEAIVL
TVPGSERSYDLTGLKPATEYTVSIYGVGRHYTVYDSNPLSAIFTT

SEQ ID NO: 55 ISOP120AR5P1B12
LPAPKNLVVSRVTEDSARLSWDGDKWANFKFDSFLIQYQESEKVGEAIVL
TVPGSERSYDLTGLKPGTEYTVSIYGVGLHYIVYDSNPLSAIFTT

SEQ ID NO: 56 ISOP120BR5P1C1
LPAPKNLVVSRVTEDSARLSWVREDAYAFDSFLIQYQESEKVGEAIVLTV
PGSERSYDLTGLKPGTEYTVSIYGVSSLHWVVHDSNPLSAIFTT

SEQ ID NO: 57 ISOP120BR5P1F1
LPAPKNLVVSRVTEDSARLSWTFHPTFEGFDSFLIQYQESEKVGEAIVLT
VPGSERSYDLTGLKPGTEYTVSIYGVKWTVLRPWLSNPLSAIFTT

SEQ ID NO: 58 ISOP120BR5P1D2
LPAPKNLVVSRVTEDSARLSWIRKHNHVKWFDSFLIQYQESEKVGEAIVL
TVPGSERSYDLTGLKPGTEYTVSIYGVGFLIDTDDSNPLSAIFTT

SEQ ID NO: 59 ISOP120BR5P1E2
LPAPKNLVVSRVTEDSARLSWAQELDHFDSFLIQYQESEKVGEAIVLTVP
GSERSYDLTGLKPGTEYTVSIYGVYWTWWVRWNSNPLSAIFTT

SEQ ID NO: 60 ISOP120BR5P1F2
LPAPKNLVVSRVTEDSARLSWTFHPTFEGFDSFLIQYQESEKVGEAIVLT
VPGSERSYDLTGLKPGTEYTVSIYGVKWYAGIGYPVSNPLSAIFTT

SEQ ID NO: 61 ISOP120BR5P1D3
LPAPKNLVVSRVTEDSARLSWSEHPTPFATFDSFLIQYQESEKVGEAIVL
TVPGSERSYDLTGLKPGTEYTVSIYGVWWVENHFPVSNPLSAIFTT

SEQ ID NO: 62 ISOP120BR5P1H3
LPAPKNLVVSRVTEDSARLSWEESRQFFDSFLIQYQESEKVGEAIVLTVP
GSERSYDLTGLKPGTEYTVSIYGVVHRAWLRWNGSNPLSAIFTT

SEQ ID NO: 63 ISOP120BR5P1E4
LPAPKNLVVSRVTEDSARLSWDDQFEDWFDSFLIQYQESEQVGEAIVLTV
PGSERSYDLTGLKPGTEYTVSIYGVHTRDWTAWNASNPLSAIFTT

SEQ ID NO: 64 ISOP120BR5P1G4
LPAPKNLVVSRVTEDSARLSWAGHYRKIRNFDSFLIQYQESEKVGEAIVL
TVPGSERSYDLTGLKPGTEYTVSIYGVKFPYYYATADSNPLSAIFTT

SEQ ID NO: 65 ISOP120BR5P1A5
LPAPKNLVVSRVTEDSARLSWAGHYRKIRNFDSFLIQYQESEKVGEAIVL
TVPGSKRSYDLTGLKPGTEYTVSIYGVKFPYYYATADSNPLSAIFTT

SEQ ID NO: 66 ISOP120BR5P1E6
LPAPKNLVVSRVTEDSARLSWLEGANAEFDSFLIQYQESEKVGEAIVLTV
PGSERSYDLTGLKPGTEYTVSIYGVHWVGPWYPVSNPLSAIFTT

SEQ ID NO: 67 ISOP120BR5P1B7
LPAPKNLVVSRVTEDSARLSWGAKTRQFDSFLIQYQESEKVGEAIVLTVP
GSERSYDLTGLKPGTEYTVSIYGVWWVENHFPVSNPLSAIFTT

SEQ ID NO: 68 ISOP120BR5P1C7
LPAPKNLVVSRVTEDSARLSWNVTQKEFDSFLIQYQESEKVGEAIVLTVP
GSERSYDLTGLKPGTEYTVSIYGVGNRYYTVYDSNPLSAIFTT

SEQ ID NO: 69 ISOP120BR5P1D8
LPAPKNLVVSRVTEDSARLSWKNHTQEWEFDSFLIQYQESEKVGEAIVLT
VPGSERSYDLTGLKPGTEYTVSIYGVPIAWLAWTSTSNPLSAIFTT

SEQ ID NO: 70 ISOP120BR5P1E8
LPAPKNLVVSRVTEDSARLSWNGGEYWVPRFDSFLIQYQESEKVGEAIVL
TVPGSERSYDLTGLKPGTEYTVSIYGVVWLQWISWTDSNPLSAIFTT

SEQ ID NO: 71 ISOP120BR5P1B9
LPAPKNLVVSRVTEDSARLSWAVEFNPTKFDSFLIQYQESEKVGEAIVLT
VPGSERSYDLTGLKPGTEYTVSIYGVWWFEQWYPVSNPLSAIFTT

SEQ ID NO: 72 ISOP120BR5P1C9
LPAPKNLVVSRVTEDSARLSWAWNRHDFDSFLIQYQESEKVGEAIVLTVP
GSERSYDLTGLKPGTEYTVSIYGVHWTVLRPFIDSNPLSAIFTT

SEQ ID NO: 73 ISOP120BR5P1D9
LPAPKNLVVSRVTEDSARLSWTINSHIFDSFLIQYQESEKVGEAIVLTVP
GSERSYDLTGLKPGTEYTVSIYGVWGTKYWQAQSNPLSAIFTT

SEQ ID NO: 74 ISOP120BR5P1A10
LPAPKNLVVSRVTEDSARLSWTEEDITHLRFDSFLIQYQESEKVGEAIVL
TVPGSERSYDLTGLKPGTEYTVSIYGVYWTWWVRWNSNPLSAIFTT

SEQ ID NO: 75 ISOP120BR5P1G11
LPAPKNLVVSRVTEDSARLSWTKRHFYTFDSFLIQYQESEKVGEAIVLTV
PGSERSYYLTGLKPGTENTVSIYGVHGNHPYTDAPANPLSAIFTT

SEQ ID NO: 76 ISOP120GR5P1E1
LPAPKNLVVSRVTEDSARLSWTAPDAAFDSFIIQYAEDSSWGEAINLHVP
GSERSYDLTGLKPGTEYHVHIYGVKGGEASNPLWAWFTT

SEQ ID NO: 77 ISOP120GR5P1G3
LPAPKNLVVSRVTEDSARLSWTAPDAAFDSFYIRYWEFCHSGEAIELSVP
GSERSYDLTGLKPGTEYFVRIVGVKGGRVSLPLGAKFTT

SEQ ID NO: 78 ISOP120GR5P1F5
LPAPKNLVVSRVTEDSARLSWTAPDAAFDSFEIDYWEVESEGEAIVLFVP
GSERSYDLTGLKPGTEYHVIVGVKGGTPSYPLWADFTT

SEQ ID NO: 79 ISOP120GR5P1H6
LPAPKNLVVSRVTEDSARLSWTNEQITKYGFDSFLIQYQESEKVGEAIVL
TVPGSERSYDLTGLKPGTEYTVSIYGVRHYTVYDSNPLSAIFTT

SEQ ID NO: 80 ISOP120GR5P1E7
LPAPKNLVVSRVTEDSARLSWTAPDAAFDSFEIDYWEVESEGEAIILFVP
GSERSYDLTGLKPGTEYHVHIVGVKGGTPSYPLWADFTT

SEQ ID NO: 81 ISOP120GR5P1A10
LPAPKNLVVSRVTEDSARLSWTAPDAAFDSFEIPYIEVETIGEAIWLHVP
GSERSYDLTGLKPGTEYSVGINGVKGGHTSNPLSARFTT

SEQ ID NO: 82 ISOP120GR5P1C10
LPAPKNLVVSRVTEDSARLSWTAPDGAFDSFEIPYIEVETIGEAIWLHVP
GSERSYDLTGLKPGTEYSVGINGVKGGHTSNPLSARFTT

SEQ ID NO: 83 ISOP120GR5P1A11
LPAPKNLVVSRVTEDSARLSWTAPDAAFDSFGIPYWEWTTEGEAIQLIVP
GSERSYDLTGLKPATEYHVHIVGVKGGSFSEPLPADFTT

SEQ ID NO: 84 ISOP120GR5P1B11
LPAPKNLVVSRVTEDSARLSWTAPDAAFDSFNIKYWEANLYGEAIVLTVP
GSERSYGLTGLKPGTEYRVHIRGVKGGINSFPLVAVFTT

SEQ ID NO: 85 ISOP120GR5P1H11
LPAPKNLVVSRVTEDSARLSWTAPDAAFDSFYIAYWEYWGNGEAIGLIVP
GSERSYDLTGLKPGTEYHVHIVGVKGGAGSVPLWANFTT

SEQ ID NO: 86 ISOP120HR5P1E2
LPAPKNLVVSHVTEDSARLSWTAPDAAFDSFEIYYLEGGRGEAIVLTVPG
SERSYDLTVLKPGTEYLGTIYGVKCGWASNPLSAIFTT

SEQ ID NO: 87 ISOP120HR5P1A3
LPAPKNLVVSRVTEDSARLSWTAPDAAFDSFEIYYAEFGYYGEAIVLTVP
GSERSYDLTGLKPGTEYTVTIYGVKGGWYSTPLSAIFTT

SEQ ID NO: 88 ISOP120HR5P1B4
LPAPKNLVVSRVTEDSARLSWTAPDAAFDSFSIYYGEYYNLGEAIVLTVP
GSERSYDLTGLKPGTEYVVTIYGVKGGGYSNPLSAIFTT

SEQ ID NO: 89 ISOP120HR5P1G4
LPAPKNLVVSRVTEDSARLSWTAPDAAFDSFEIYYREYWYSGEAIVLTVP
GSERSYDLTGLKPGTEYLVTIYGVKGGWYSDPLSAIFTT

SEQ ID NO: 90 ISOP120HR5P1H4
LPAPKNLVVSRVTEDSARLSWTAPDAAFDSFDILYLEPYQEGEAIVLTVP
GSERSYDLTGLKPGTEYLVTIYGVKGGYYSLPLSAIFTT

SEQ ID NO: 91 ISOP120HR5P1B5
LPAPKNLVVSRVTEDSARLSWTAPDAAFDSFIIRYIEEGYYGEAIVLTVP
GSERSYDLTGLKPGTEYHVGIEGVKGGYYSPLSAIFTT

SEQ ID NO: 92 ISOP120HR5P1A6
LPAPKNLVVSRVTEDSARLSWTAPDGAFDSFEIYYLEGGRGEAIVLTVPG
SERSYDLTGLKPGTEYLVTIYGIKCGWASNPLSAIFTT

SEQ ID NO: 93 ISOP120HR5P1G6
LPAPKNLVVSRVTEDSARLSWTAPDAAFDSFEIYYFELRLGGEAIVLTVP
GSERSYDLTGLKPGTEYLVTIYGVKGGLDSQPLSAIFTT

SEQ ID NO: 94 ISOP120HR5P1A7
LPAPKNLVVSRVTEDSARLSWTAPDAAFDSFEIYYAEPRYYGEAIVLTVP
GSERSYDLTGLKPGTEYTVTIYGVKGGYYSSPLSAIFTT

SEQ ID NO: 95 ISOP120HR5P1D7
LPAPKNLVVSRVTEDSARLSWTAPDAAFDSFDIYYLESWTRGEAIVLTVP
GSERSYDLTGLKPGTEYLVTIYGVKGGSYSRPLSAIFTT

SEQ ID NO: 96 ISOP120HR5P1E7
LPAPKNLVVSRVTEDSARLSWTAPDAAFDSFQIYYLEQLGYGEAIVLTVP
GSERSYDLTGLKPGTEYLVTIYGVKVCEQSYPLSAIFTT

SEQ ID NO: 97 ISOP120HR5P1H7
LPAPKNLVVSRVTEDSARLSWTAPDAAFDSFDIYYGEPGNLGEAIVLTVP
GSERSYDLTGLKPGTEYLVTIYGVKGGDYSSPLSAIFTT

SEQ ID NO: 98 ISOP120HR5P1H8
LPAPKNLVVSRVTEDSARLSWTAPDAAFDSFDIYYYELRLGGEAIVLTVP
GSERSYDLTGLKPGTEYLVTIYGVKGGYYSGPLSAIFTT

SEQ ID NO: 99 ISOP120HR5P1D9
LPAPKNLVVSRVTEDSARLSWTAPDAAFDSFDIYYRELDFQGEAIVLTVP
GSERSYDLTGLKPGTEYLVIIYGVKGGSYSYTLSAIFTT

SEQ ID NO: 100 ISOP120HR5P1F9
LPAPKNLVVSRVTEDSARLSWTAPDAAFDSFYIYYREHWTIGEAIVLTVP
GSERSYDLTGLKPGTEYLVTIYGVKGGAYSNPLSAIFTT

SEQ ID NO: 101 ISOP120ER5P1B4
LPAPKNLVVSRVTEDSARLSWTAPDAAFDSFSILYGEPPALGEAIVLTVP
GSERSYDLTGLKPGTEYWVTIYGVKGGVFSHPLSAIFTT

SEQ ID NO: 102 ISOP120ER5P1F4
LPAPKNLVVSRVTEDSARLSWTAPDAAFDSFVIRYIEDTVMGEAIVLTVP
GSERSYDLTGLKPGTEYHVSIEGVKGGPSSLPLSAIFTT

SEQ ID NO: 103 ISOP120ER5P1H4
LPAPKNLVVSRVTEDSARLSWTAPDAAFDSFNIMYLEDVQCGEAIVLTVP
GSERSYDLTGLKPGTEYHVGINGVKGGLRSFPLSAIFTT

SEQ ID NO: 104 ISOP120ER5P1E5
LPAPKNLVVSRVTEDSARLSWTAPDAAFDSFRISYLEDVYYGEAIVLTVP
GSERSYDLTGLKPGTEYHVGIHGVKGGIDSFPLSAIFTT

SEQ ID NO: 105 ISOP120ER5P1B6
LPAPKNLVVSRVTEDSARLSWTAPDAAFDSFDIYYGEHWKLGEAIVLTVQ
GSERSYDLTGLKPGTEYLVTIYGVKGGQWSFPLSAIFTT

SEQ ID NO: 106 ISOP120ER5P1C6
LPAPKNLVVSRVTEDSARLSWTAPDAAFDSFSIYYGEWHALGEAIVLTVP
GSERSYDLTGLKPGTEYVVTIYGVKGGTYSLPLSAISTT

SEQ ID NO: 107 ISOP120ER5P1H6
LPAPKNLVVSRVTEDSARLSWTAPDAAFDSFSIYYGEWHALGEAIVLTVP
GSERSYDLTGLKPGTEYVVTIYGVKGGTYSLPLSAIFTT

SEQ ID NO: 108 ISOP120ER5P1A7
LPAPKNLVVSRVTEDSARLSWTAPDAAFDSFNIGYYERIIPGEAIVLTVP
GSERSYDLTGLKPGTEYSVLICGVKGGKGSIPLSAIFTT

SEQ ID NO: 109 ISOP120ER5P1A8
LPAPKNLVVSRVTEDSARLSWTAPDAAFDSFDIYYFEHPVGGEAIVLTVP
GSERSYDLTGLKPGTEYLVTIYGVKGGYLSMPLSAIFTT

SEQ ID NO: 110 ISOP120ER5P1E10
LPAPKNLVVSRVTEDSARLSWTAPDAAFDSFEIYYMEDFHSGEAIVLTVP
GSERSYDLTGLKPGTEYWVTIYGVEGGTGSLPLSAIFTT

SEQ ID NO: 111 ISOP120ER5P1A11
LPAPKNLVVSRVTEDSARLSWTAPDAAFDSFEIYYKELRAEGEAIVLTVP
GSERSYDLTGLKPGTEYLVTIYGVKGGSVSIPLSAIFTT

SEQ ID NO: 112 ISOP120ER5P1B12
LPAPKNLVVSRVTEDSARLSWTAPDAAFDSFAIYYIEWTAYGEAIVLTVP
GSERSYDLTGLKPGTEYVVRISGVKCGIVSFPLSAIFTT

SEQ ID NO: 113 ISOP120FR5P1F1
LPAPKNLVVSRVTEDSARLSWTAPDAAFDSFTIYYFENENGGEAIVLTVP
GSERSYDLTGLKPGTEYLVTIYGVKGCDWSDPLSAIFTT

SEQ ID NO: 114 ISOP120FR5P1C2
LPAPKNLVVSRVTEDSARLSWTAPDAAFDSFDINYFEQPKGGEAIVLTVP
GSERSYDLTGLKPGTEYLVTIYGVKGGPYSPPLSAIFTT

SEQ ID NO: 115 ISOP120FR5P1H5
LPAPKNLVVSRVTEDSARLSWTAPDAAFDSLQIYYFEWVVGGEAIVLTVP
GSERSYDLTGLKLGTEYLVTIYGVKGGNFSDPLSAIFTT

SEQ ID NO: 116 ISOP120FR5P1A6
LPAPKNLVVSRVTEDSARLSWTAPDAAFDSFIIRYLEDISYGEAIVLTVP
GSERSYDLTGLKPGTEYHVGIEGVKGGNVSFPLSAIFTT

SEQ ID NO: 117 ISOP120FR5P1H6
LPAPKNLVVSRVTEDSARLSWTAPDAAFDSFGIPYLEDIEVGEAIVLTVP
GSERSYDLAGLKPGTEYHVGIYGVKGGEQSFPLSAIFTT

SEQ ID NO: 118 ISOP120FR5P1D7
LPAPKNLVVSRVTEDSARLSWTAPDAAFDSFIIRYLEDISYGEAIVLTVP
GSERSYDLTGLKPGTEYHVGIEGVKGGNVSWPLSAIFTT

SEQ ID NO: 119 ISOP120FR5P1F8
LPAPKNLVVSRVTEDSARLSWTAPDAAFDSFIIRYLEDISYGEAIVLTVP
GSERSYDLTGLKPGTEYHVGIEGVKGGNVSWPLSAIFTT

SEQ ID NO: 120 ISOP120FR5P1E9
LPAPKNLVVSRVTEDSARLSWTAPDAAFDSFIIYYPEYISNGEAIVLTVP
GSERSYDLTGLKPGTEYHVTIGVKGGHSWPLSAIFTT

SEQ ID NO: 121 ISOP120FR5P1E10
LPAPKNLVVSRVTEDSARLSWTAPDAAFDSFLIHYTEQPSKGEAIVLTVP
GSERSYDLTGLKPGTEYQVPIGVKGGTQSCPLSAIFTT

SEQ ID NO: 122 ISOP120FR5P1A11
LPAPKNLVVSRVTEDSARLSWTAPDAAFDSFTIYYFENENGGEAIVLTVP
GSERSYDLTGLKPGTEYLVTIYGVKGGHWSRPLSAIFTT

SEQ ID NO: 123 ISOP193AR9P1A11
LPAPKNLVVSRVTEDSARLSWALSSVHAYFDSFLIQYQESEKVGEAIVLT
VPGSERSYDLTGLKPGTEYTVSIYGVQYVDGFFKSNPLSAIFTT

SEQ ID NO: 124 ISOP193AR9P1A6
LPAPKNLVVSRVTEDSARLSWKFGEVAFDSFLIQYQESEKVGEAIVLTVP
GSERSYDLTGLKPGTEYTVSIYGVGRHYTVYDSNPLSAIFTT

SEQ ID NO: 125 ISOP193AR9P1B10
LPAPKNLVVSRVTEDSARLSWAFQWHIFDSFLIQYQESEKVGEAIVLTVP
GSERSYDLTGLKPGTEYTVSIYGVGRHYTVYDSNPLSAIFTT

SEQ ID NO: 126 ISOP193AR9P1B12
LPAPKNLVVSRVTEDSARLSWTNEQITKYGFDSFLIQYQESEKVGEAIVL
TVPGSERSYDLTGLKPGTEYTVSIYGVGAPYTVYDSNPLSAIFTT

SEQ ID NO: 127 ISOP193AR9P1B4
LPAPKNLVVSRVTEDSARLSWRDLQYHTFDSFLIQYQESEKVGEAIVLTV
PGSERSYDLTGLKPGTEYTVSIYGVGRHYTVYDSNPLSAIFTT

SEQ ID NO: 128 ISOP193AR9P1C10
LPAPKNLVVSRVTEDSARLSWPNHISIFDSFLIQYQESEKVGEAIVLTVP
GSERSYDLTGLKPGTEYTVSIYGVGRFYTVFDSNPLSAIFTT

SEQ ID NO: 129 ISOP193AR9P1E6
LPAPKNLVVSRVTEDSARLSWKFHSPTFDSFLIQYQESEKVGEAIVLTVP
GSERSYDLTGLKPGTEYTVSIYGVGRHYTVYDSNPLSAIVTT

SEQ ID NO: 130 ISOP193AR9P1F4
LPAPKNLVVSRVTEDSARLSWLEQEQFVNHFDSFLIQYQESEKVGEAIVL
TVPGSERSYDLTGLKPGTEYTVSIYGVQYVDGFFKSNPLSAIFTT

SEQ ID NO: 131 ISOP193AR9P1F9
LPAPKNLVVSRVTEDSARLSWPLFASDLNIFDSFLIQYQESEKVGEAIVL
TVPGSERSYDLTGLKPGTEYTVSIYGVGRHYTVYDSNPLSAIFTT

SEQ ID NO: 132 ISOP193AR9P1G11
LPAPKNLVVSRVTEDSARLSWTNEQITKYGFDSFLIQYQESEKVGEAIVL
TVPGSERSYDLTGLKPGTEYTVSIYGVGRHYTVYDSNPLSAIFTT

SEQ ID NO: 133 ISOP193AR9P1G5
LPAPKNLVVSRVTEDSARLSWRISDRLPLFDSFLIQYQESEKVGEAIVLT
VPGSERSYDLTGLKPGTEYTVSIYGVGRHYTVYDSNPLSAIFTT

SEQ ID NO: 134 ISOP193AR9P1G8
LPAPKNLVVSRVTEDSARLSWHATFGDPFDSFLIQYQESEKVGEAIVLTV
PGSERSYDLTGLKPGTEYTVSIYGVGRHYTVYDSNPLSAIFTT

SEQ ID NO: 135 ISOP193AR9P1H8
LPAPKNLVVSRVTEDSARLSWTNEQITKYGFDSFLIQYQESEKVGEAIVL
TVPGSERSYDLTGLKPGTEYTVSIYGVGRFYTVFDSNPLSAIFTT

SEQ ID NO: 136 ISOP193BR9P1B10
LPAPKNLVVSRVTEDSARLSWAWNRHDFDSFLIQYQESEKVGEAIVLTVP
GSERSYDLTGLKPGTEYTVSIYGVHWTVLRPFIDSNPLSAIFTT

SEQ ID NO: 137 ISOP193BR9P1B12
LPAPKNLVVSRVTEDSARLSWPDESRPVRFDSFLIQYQESEKVGEAIVLT
VPGSERSYDLTGLKPGTEYTVSIYGVLRPWIYATNDSNPLSAIFTT

SEQ ID NO: 138 ISOP193BR9P1E6
LPAPKNLVVSRVTEDSARLSWGAITALFDSFLIQYQESEKVGEAIVLTVP
GSERSYDLTGLKPGTEYTVSIYGVKFPYYYATADSNPLSAIFTT

SEQ ID NO: 139 ISOP193BR9P1G11
LPAPKNLVVSRVTEDSARLSWAGHYRKIRNFDSFLIQYQESEKVGEAIVL
TVPGSERSYDLTGLKPGTEYTVSIYGVKFPYYYATADSNPLSAIFTT

SEQ ID NO: 140 ISOP193BR9P1G2
LPAPKNLVVSRVTEDSARLSWAGHYRKIRNFDSFLIQYQESEKVGEAIVL
TVPGSERSYDLTGLKPGTEYTVSIYGVAEHWYYATQDSNPLSAIFTT

SEQ ID NO: 141 ISOP193BR9P1G3
LPAPKNLVVSRVTEDSARLSWAQSNQQFDSFLIQYQESEKVGEAIVLTVP
GSERSYDLTGLKPGTEYTVSIYGVVWQNWVAYNSNPLSAIFTT

```
SEQ ID NO: 142 ISOP193BR9P1G6
LPAPKNLVVSRVTEDSARLSWDDQFEDWFDSFLIQYQESEQVGEAIVLTV
PGSERSYDLTGLKPGTEYTVSIYGVHTRDWTAWNASNPLSAIFTT

SEQ ID NO: 143 ISOP193BR9P1G9
LPAPKNLVVSRVTEDSARLSWKQVTVAPEFDSFLIQYQESEKVGEAIVLT
VPGSERSYDLTGLKPGTEYTVSIYGVKFPYYYATADSNPLSAIFTT

SEQ ID NO: 144 ISOP193BR9P1H2
LPAPKNLVVSRVTEDSARLSWPDESRPVRFDSFLIQYQESEKVGEAIVLT
VPGSERSYDLTGLKPGTEYTVSIYGVHTRDWTAWNASNPLSAIFTT

SEQ ID NO: 145 ISOP193BR9P1H3
LPAPKNLVVSRVTEDSARLSWNRLDSEWVAFDSFLIQYQESEKVGEAIVL
TVPGSERSYDLTGLKPGTEYTVSIYGVVFRPWLAYNSNPLSAIFTT

SEQ ID NO: 146 ISOP193BR9P1H6
LPAPKNLVVSRVTEDSARLSWPDESRPVRFDSFLIQYQESEKVGEAIVLT
VPGSERSYDLTGLKPGTEYTVSIYGVVGQWKYATADSNPLSAIFTT

SEQ ID NO: 147 ISOP193ER9P1A10
LPAPKNLVVSRVTEDSARLSWTAPDAAFDSFDIYYFEHPVGGEAIVLTVP
GSERSYDLTGLKPGTEYLVTIYGVKGGHFSGPLSAIFTT

SEQ ID NO: 148 ISOP193ER9P1A11
LPAPKNLVVSRVTEDSARLSWTAPDAAFDSFAIQYQEYVAHGEAIVLTVP
GSERSYDLTGLKPGTEYHVRISGVKGGGVSWPLSAIFTT

SEQ ID NO: 149 ISOP193ER9P1A3
LPAPKNLVVSRVTEDSARLSWTTPDAAFDSFDIYYFEHPVGGEAIVLTVP
GSERSYDLTGLKPGTEYLVTIYGVKGGYLSKPLSAIFTT

SEQ ID NO: 150 ISOP193ER9P1A4
LPAPKNLIVSRVTEDSARLSWTAPDAAFDSFEIYYKELRAEGEAIVLTVP
GSERSYDLTGLKPGTEYLVTIYGVKGGSVSIPLSAIFTT

SEQ ID NO: 151 ISOP193ER9P1A8
LPAPKNLVVSRVTEDSARLSWTAPDAAFDSLDIYYFEHPVGGEAIVLTVP
GSERSYDLTGLKPGTEYLVTIYGVKGGYLSMPLSAIFTT

SEQ ID NO: 152 ISOP193ER9P1B4
LPAPKNLVVSHVTEDSARLSWTAPDAAFDSFDIYYFEHPVGGEAIVLTVP
GSERSYDLTGLKPGTEYLVTIYGVKGGYLSMPLSAIFTT

SEQ ID NO: 153 ISOP193ER9P1B5
LPAPKNLVVSRVTEDSARLSWTAPDAAFDSFAIQYQEYVAHGEAIVLTVP
GSERSYDLTGLKPGTEYHVRISGVKGGGVSWPLSAIVTT

SEQ ID NO: 154 ISOP193ER9P1C10
LLAPKNLVVSRVTEDSARLSWIAPDAAFDSFEIYYKELRAEGEAIVLTVP
GSERSYDLTGLKPGTEYLVTIYGVKGGSVSIPLSAIFTT

SEQ ID NO: 155 ISOP193ER9P1C4
LPAPKNLVVSRVTEDSARLSWTAPDAAFDSFDIYYFEHPVGGEAIVLTVP
GSERSYDLTGLKPGTEYLVTIYGVKGGIWSVPLSAIFTT

SEQ ID NO: 156 ISOP193ER9P1C8
LPAPKNLVVSRVTEDSARLSWTAPDAAFDSFDIYYFEHPVGGEAIVLTVP
GSERSYDLTGLKPGTEYLVTIYGVKGGTYSLPLSAIFTT

SEQ ID NO: 157 ISOP193ER9P1C9
LPAPKNLVVSRVTEDSARLSWTAPDAAFDSFDIYYFEHPVGGEAIVLTVP
GSERSYDLTGLKPGTEYLVTIYGVKGGELSKPLSAISTT

SEQ ID NO: 158 ISOP193ER9P1D4
LPAPKNLVVSRVTEDSARLSWTAPDAAFDSFDIYYFEHPVGGEAIVLTVP
GSERSYDLTGLKPGTEYLVTIYGVKGGTYSPPLSAIFTT

SEQ ID NO: 159 ISOP193ER9P1D7
LPAPKNLVVSRVTEDSARLSWTAPDAAFDSFDIYYGEHWKLGEAIVLTVP
GSERSYDLTGLKPGTEYLVTIYGVKGGMSSNPLSAIFTT

SEQ ID NO: 160 ISOP193ER9P1E1
LPAPKNLVVSRVTEDSARLSWTAPDAAFDSFDIYYFEHPVGGEAIVLTVP
GSERSYDLTGLKPGTEYLVTIYGVKGGSVSIPLSAIFTT

SEQ ID NO: 161 ISOP193ER9P1E2
LPAPKNLVVSRVTEDSARLSWTAPDAAFDSFDIYYFEHPVGGEAIVLTVP
GSERSYDLTGLKPGTEYLVTIYGVKGGFWSQPLSAIFTT

SEQ ID NO: 162 ISOP193ER9P1E4
LPAPKNLVVSRVTEDSARLSWTAPDAAFDSFAIIYQEYVKSGEAIVLTVP
GSERSYDLTGLKPGTEYHVRIGGVKGGLLSLPLSAIFTT

SEQ ID NO: 163 ISOP193ER9P1E8
LPAPKNLVVSRVTEDSARLSWTAPDAAFDSFDIYYFEHPVGGEAIVLTVP
GSERSYDLTGLKPGTEYLVTIYGVKGGELSKPLSAIFTT

SEQ ID NO: 164 ISOP193ER9P1F11
LPAPKNLVVSRVTEDSARLSWTAPDAAFDSFAIQYQEYVAHGEAIVLTVP
GSERSYDLTGLKPGTEYHVRISGVKGGGVSWPLSAISTT

SEQ ID NO: 165 ISOP193ER9P1F7
LPAPKNLVVSRVTEDSAHLSWTAPDAAFDSFDIYYFEHPVGGEAIVLTVP
GSERSYDLTGLKPGTEYLVTIYGVKGGYLSMPLSAIFTT

SEQ ID NO: 166 ISOP193ER9P1F9
LPAPKNLVVSRVTEDSARLSWTAPDAAFDSFHIYYGEHYNLGEAIVLTVP
GSERSYDLTGLKPGTEYLVTIYGVKGGFWSTPLSAIFTT

SEQ ID NO: 167 ISOP193ER9P1G11
LPAPKNLVVSRVTEDSARLSWTAPDAAFDSFDIYYFEHPVGGEAIVLTVP
GSERSYDLTGLKPGTEYLVTIYGVKGGYLSMPLSAIFTT

SEQ ID NO: 168 ISOP193ER9P1G2
LPAPKNLVVSRVTEDSARLSWTAPDAAFDSFDIYYFEQPVGGEAIVLTVP
GSERSYDLTGLKPGTEYLVTIYGVKGGYLSMPLSAIFTT

SEQ ID NO: 169 ISOP193ER9P1G4
LPAPKNLVVSRVTEDSARLSWTAPDAAFDSFDIYYFEHPVGGEAIVLTVP
GSERSYDLTGLKPGTEYLVTIYGVKGGNFSFPLSAIFTT

SEQ ID NO: 170 ISOP193ER9P1G5
LPAPKNLVVSRVTEDSARLSWTAPDAAFDSFDIYYFEHPVGGEAIVLTVP
GSERSYDLTGLKPGTEYLVTIYGVKGGYLSMPLSAIFTT

SEQ ID NO: 171 ISOP193ER9P1G9
LPAPKNLVVSRVTEDSARLSWTAPDAAFDSFDIYYFEHPVGGEAIVLTVP
GSERSYDLTGLKPGTEYLVTIYGVKGGNGSSPLSAIFTT

SEQ ID NO: 172 ISOP193ER9P1H11
LPAPKNLVVSRVTEDSARLSWTAPDAAFDSFDIYYFEHPVGGEAIVLTVP
GSERSYDLTGLKPGTEYLVAIYGVKGGVFSHPLSAIFTT

SEQ ID NO: 173 ISOP193ER9P1H2
LPAPKNLVVSRVTEDSARLSWTAPDAAFDSFRISYLEDVYYGEAIVLTVP
GSERSYDLTGLKPGTEYHVGIHGVKGGIDSFPLSAIFTT
```

```
SEQ ID NO: 174 ISOP193ER9P1H3
LPAPKNLVVSRVTEDSARLSWTAPDAAFDSFEIYYLEVRNRGEAIVLTVP

GSERSYDLTGLKPGTEYHVGIAGVKGGFHSFPLSAIFTT

SEQ ID NO: 175 ISOP193FR9P1A11
LPAPKNLVVSRVTEDSARLSWTAPDAAFDSFAIQYWEGWEWGEAIVLTVP

GSERSYDLTGLKPGTEYLVTIYGVKGGHWSRPLSAIFTT

SEQ ID NO: 176 ISOP193FR9P1A5
LPAPKNLVVSRVTEDSARLSWTAPDAAFDSFEIYYIEPIAPGEAIVLTVP

GSERSYDLTGLKPGTEYWVTIYGVKGCDWSDPLSAIFTT

SEQ ID NO: 177 ISOP193FR9P1C1
LPAPKNLVVSRVTEDSARLSWTAPDAAFDSFEIYYFENENGGEAIVLTVP

GSERSYDLTGLKPGTEYLVTIYGVKGCDWSDPLSAIFTT

SEQ ID NO: 178 ISOP193FR9P1C5
LPAPKNLVVSRVTEDSARLSWTAPDAAFDSFHIYYLEQYSRGEAIVLTVP

GSERSYDLTGLKPGTEYLVTIYGVKGCDWSDPLSAIFTT

SEQ ID NO: 179 ISOP193FR9P1C9
LPAPKNLVVSRVTEDSARLSWTAPDAAFDSFQIYYFEWVVGGEAIVLTVP

GSERSYDLTGLKPGTEYLVTIYGVKGCDWSDPLSAIFTT

SEQ ID NO: 180 ISOP193FR9P1D1
LPAPKNLVVSRVTEDSARLSWTAPDAAFDSFFIQYLEDVTNGEAIVLTVP

GSERSYDLTGLKPGTEYRVPIAGVKGGRDSQPLSAIFTT

SEQ ID NO: 181 ISOP193FR9P1D5
LPAPKNLVVSRVTEDSARLSWTAPDAAFDSFYIRYIEDVDFGEAIVLTVP

GSERSYDLTGLKPGTEYLVTIYGVKGCDWSDPLSAIFTT

SEQ ID NO: 182 ISOP193FR9P1D7
LPAPKNLVVSRVTEDSARLSWTAPDAAFDSFEIYYAEYFKNGEAIVLTVP

GSERSYDLTGLKPGTEYLVTIYGVKGCDWSDPLSAISTT

SEQ ID NO: 183 ISOP193FR9P1E1
LPAPKNLVVSRVTEDSARLSWTAPDAAFDSFIIRYLEDISYGEAIVLTVP

GSERSYDLTGLKPGTEYHVGIEGVKGGNVSWPLSAIFTT

SEQ ID NO: 184 ISOP193FR9P1E10
LPAPKNLVVSRVTEDSARLSWTTPDAAFDSFHIHYLEGEWGGEAIVLTVP

GSERSYDLTGLKPGTEYLVTIYGVKGCDWSDPLSAIFTT

SEQ ID NO: 185 ISOP193FR9P1F8
LPAPKNLVVSRVTEDSARLSWTAPDAAFDSFDINYFENELGGEAIVLTVP

GSERSYDLTGLKPGTEYLVTIYGVKGCDWSDPLSAIFTT

SEQ ID NO: 186 ISOP193FR9P1G10
LPAPKNLVVSRVTEDSARLSWTAPDAAFDSFTIYYFENENGGEAIVLTVP

GSERSYDLTGLKPGTEYLVTIYGVKGGHWSRPLSAIFTT

SEQ ID NO: 187 ISOP193FR9P1G11
LPAPKNLVVSRVTEDSARLSWTAPDAAFDSFTIYYFENENGGEAIVLTVP

GSERSYDLTGLKPGTEYLVTIYGVKGCDWSDPLSAIFTT

SEQ ID NO: 188 ISOP193FR9P1G2
LPAPKNLVVSRVTEDSARLSWTAPDAAFDSFTIYYFENENGGEAIVLTVP

GSERSYDLTGLKPDTEYLVTIYGVKGGHWSRPLSAIFTT

SEQ ID NO: 189 ISOP193FR9P1G4
LPAPKNLVVSRVTEDSARLSWTAPDAAFDSFEIYYFENELGGEAIVLTVP

GSERSYDLTGLKPGTEYLVTIYGVKGGDWSDPLSAIFTT

SEQ ID NO: 190 ISOP193FR9P1G7
LPAPKNLVVSRVTEDSARLSWTAPDAAFDSFHIHYLEGEWGGEAIVLTVP

GSERSYDLTGLKPGTEYLVTIYGVKGCDWSDPLSAIFTT

SEQ ID NO: 191 ISOP193FR9P1G8
LPAPKNLVVSRVTEDSARLSWTAPDAAFDSFEIYYFENELGGEAIVLTVP

GSERSYDLTGLKPGTEYLVTIYGVKGCDWSDPLSAIFTT

SEQ ID NO: 192 ISOP193FR9P1G9
LPAPKNLFVSRVTEDSARLSWTAPDAAFDSFQIYYREQWWDGEAIVLTVP

GSERSYDLTGLKPGTEYLVTIYGVKGCDWSDPLSAIFTT

SEQ ID NO: 193 ISOP193FR9P1H6
LPAPKNLVVSRVTEDSARLSWTAPDAAFDSFDINYFEQPKGGEAIVLTVP

GSERSYDLTGLKPGTEYLVTIYGVKGCDWSDPLSAIFTT

SEQ ID NO: 194 ISOP193FR9P1H9
LPAPKNLVVSRVTEDSARLSWTAPDAAFDSFEIYYDELRNPGEAIVLTVP

GSERSYDLTGLKPGTEYAVTIYGVKGGRYSPPLSAIFTT

SEQ ID NO: 195 ISOP193GR9P1A7
LPAPKNLVVSRVTEDSARLSWTAPDAAFDSFAIFYHEFANPGEAIDLPVP

GSERSYDLTGLKPGTEYDVRIYGVKGGTASIPLDAEFTT

SEQ ID NO: 196 ISOP193GR9P1B3
LPAPKNLVVSRVTEDSARLSWTAPDAAFDSFAIGYVEWTANGEAIVLIVP

GSERSYDLTGLKPGTEYVVRIRGGVKGGDSSFPLRADFTT

SEQ ID NO: 197 ISOP193GR9P1E10
LPAPKNLVVSRVTEDSARLSWTAPDAAFDSFAISYTESIRQGEAIWLWVP

GSERSYDLTGLKPGTEYEVTIGGVKGGIRSYPLWAWFTT

SEQ ID NO: 198 ISOP193GR9P1F6
LPAPKNLVVSRVTEDSARLSWTAPDAAFDSFEIDYWEVESEGEAIVLFVP

GSERSYDLTGLKPGTEYHVHIVGVKGGTPSYPLWADFTT

SEQ ID NO: 199 ISOP193GR9P1F7
LPAPKNLVVSRVTEDSARLSWTAPDAAFDSFDIPYVEYYPSGEAIVLNVP

GSERSYDLTGLKPGTEYGVTIWGIKGGNESVPLTARFTT

SEQ ID NO: 200 ISOP193GR9P1G9
LPAPKNLVVSRVTEDSARLSWTAPDAAFDSFAIFYHEFANSGEAIDLPVP

GSERSYDLTGLKPGTEYDVRIYGVKGGTASIPLDAEFTT

SEQ ID NO: 201 ISOP193GR9P1H2
LPAPKNLVVSRVTEDSARLSWTAPDAAFDSFEIPYIEVETIGEAIWLHVP

GSERSYDLTGLKPGTEYSVGINGVKGGHTSNPLSARFTT

SEQ ID NO: 202 ISOP193HR9P1A10
LPAPKNLVVSRVTEDSARLSWTAPDAAFDSFDIYYLEPWGGGEAIVLTVP

GSERSYDLTGLKPGTEYWVTIYGVKVCLGSNPLSAIFTT

SEQ ID NO: 203 ISOP193HR9P1A11
LPAPKNLVVSRVTEDSARLSWTAPDAAFDSFEIYYLEGGRGEAIVLTVPG

SERSYDLTGLKPGTEYLVTIYGVKCGWASNPLSAIFTT

SEQ ID NO: 204 ISOP193HR9P1A5
LPAPKNLVVSRVTEDSARLSWTAPDAAFDSFDIYYYELRLGGEAIVLTVP

GSERSYDLTGLKPGTEYLVTIYGVKGCGYSAPLSAIVTT

SEQ ID NO: 205 ISOP193HR9P1A6
LPAPKNLVVSRVTEDSARLSWTAPDAAFDSFDIYYYELRLGGEAIVLTVP

GSERSYDLTGLKPGTEYLVSIYGVKGCGYSDPLSAIFTT
```

SEQ ID NO: 206 ISOP193HR9P1A7
LPAPKNLVVSRVTEDSARLSWTAPDAAFDSFDIYYYELRLGGEAIVLTVP

GSERSYDLTGLKPGTEYLVTIYGVKVCNASTPLSAIFTT

SEQ ID NO: 207 ISOP193HR9P1B11
LPAPKNLVVSRVTEDSARLSWTAPDAAFDSFEIYYFELRLGGEAIVLTVP

GSERSYDLTGLKPGTEYLVTIYGVKGCYSDPLSAIFTT

SEQ ID NO: 208 ISOP193HR9P1B7
LPAPKNLVVSRVTEDSARLSWTAPDAAFDSFEIYYFELRLGGEAIVLTVP

GSERSYDLTGLKPGTEYLVSIYGVKGCYSDPLSAIFTT

SEQ ID NO: 209 ISOP193HR9P1C7
LPAPKNLVVSRVTEDSARLSWTAPDAAFDSFEIYYLELDSDGEAIVLTVP

GSERSYDLTGLKPGTEYIVTIYGVKVCTGSRPLSAIFTT

SEQ ID NO: 210 ISOP193HR9P1C8
LPAPKNLVVSRVTEDSARLSWTAPDAAFDSFEIYYFELRLGGEAIVLTVP

GSERSYDLTGLKPGTEYLVTIYGVKGGGYSTPLSAIFTT

SEQ ID NO: 211 ISOP193HR9P1D11
LPAPKNLVVSRVTEDSARLSWTAPDAAFDSFDIYYYELRLGGEAIVLTVP

GSERSYDLTGLKPGTEYLVTIYGVKVCEQSYPLSAIFTT

SEQ ID NO: 212 ISOP193HR9P1D8
LPAPKNLVVSRVTEDSARLSWTAPDAAFDSFDIYYLESGRDGEAIVLTVP

GSERSYDLTGLKPGTEYLVSIYGVKGCYSDPLSAIFTT

SEQ ID NO: 213 ISOP193HR9P1E2
LPAPKNLVVSRVTEDSARLSWTAPDAAFDSFEIYYLEWCSGGEAIVLTVP

GSERSYDLTGLKPGTEYLVTIYGVKGCAASDPLSAIFTT

SEQ ID NO: 214 ISOP193HR9P1E3
LPAPKNLVVSRVTEDSARLSWTAPDAAFDSFEIYYFELRLGGEAIVLTVP

GSERSYDLTGLKPGTEYLVTIYGVKGGAYSNPLSAIFTT

SEQ ID NO: 215 ISOP193HR9P1E6
LPAPKNLVVSRVTEDSARLSWTAPDAAFDSFEIYYAEFGYYGEAIVLTVP

GSERSYDLTGLKPGTEYLVTIYGVKGCAASDPLSAIFTT

SEQ ID NO: 216 ISOP193HR9P1E8
LPAPKNLVVSRVTEDSARLSWTAPDAAFDSFDIYYYELRLGGEAIVLTVP

GSERSYDLTGLKPGTEYLVTIYGVKGGDYSPPLSAIFTT

SEQ ID NO: 217 ISOP193HR9P1F10
LPAPKNLVVSRVTEDSARLSWTAPDAAFDSFDIYYYELRLGGEAIVLTVP

GSERSYDLTGLKPGTEYLVTIYGVKGGYYSGPLSAIFTT

SEQ ID NO: 218 ISOP193HR9P1F8
LPAPKNLVVSRVTEDSARLSWTAPDAAFDSFDIYYYELRLGGEAIVLTVP

GSERSYDLTGLKPGTEYLVTIYGVKVCYYSTPLSAIFTT

SEQ ID NO: 219 ISOP193HR9P1G10
LPAPKNLVVSRVTEDSARLSWTAPDAAFDSFEIYYFELRLGGEAIVLTVP

GSERSYDLTGLKPGTEYLVTIYGVKGGDYSPPLSAISTT

SEQ ID NO: 220 ISOP193HR9P1G4
LPAPKNLVVSRVTEDSARLSWTAPDAAFDSFEIYYFELRLGGEAIVLTVP

GSERSYDLTGLKPGTEYLVTIYGVKGGDYSPPLSAIFTT

SEQ ID NO: 221 ISOP193HR9P1G5
LPAPKNLVVSRVTEDSARLSWTAPDAAFDSFDIYYYELRLGGEAIVLTVP

GSERSYDLTGLKPGTEYLVTIYGVKGCAASDPLSAIFTT

SEQ ID NO: 222 ISOP193HR9P1G6
LPAPKNLVVSRVTEDSARLSWTAPDAAFDSFDIYYYELRLGGEAIVLTVP

GSERSYDLTGLKPGTEYLVTIYGVKVCEQSYPLSAISTT

SEQ ID NO: 223 ISOP193HR9P1H10
LPAPKNLVVSRVTEDSARLSWTAPDAAFDSFDIYYYELRLGGEAIVLTVP

GSERSYDLTGLKPGTEYLVTIYGVKVCLGSNPLSAIFTT

SEQ ID NO: 224 ISOP193HR9P1H7
LPAPKNLVVSRVTEDSARLSWTAPDAAFDSFEIYYREPHYGGEAIVLTVP

GSERSYDLTGLKPGTEYWVTIYGVKVCLGSNPLSAIFTT

---

What is claimed:

1. An isolated protein comprising an amino acid sequence selected from the group consisting of SEQ ID NOs: 45, 46, 47, 48, 49, 50, 51, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, and 224.

2. The isolated protein of claim 1, wherein the isolated protein is conjugated to a detectable label, a cytotoxic agent, or both.

3. The isolated protein of claim 2, wherein the detectable label is a radioactive isotope, magnetic beads, metallic beads, colloidal particles, a fluorescent dye, an electron-dense reagent, an enzyme, biotin, digoxigenin, or hapten.

4. The isolated protein of claim 2, wherein the detectable label is auristatin, monomethyl auristatin phenylalanine, dolostatin, chemotherapeutic agent, a drug, a growth inhibitory agent, a toxin, or a radioactive isotope.

5. The isolated protein of claim 1, further comprising a methionine at the N-terminus of the isolated protein.

6. The isolated protein of claim 5, wherein the isolated protein is coupled to a half-life extending moiety.

7. The isolated protein of claim 6, wherein the half-life extending moiety is an albumin binding molecule, a polyethylene glycol (PEG), albumin, albumin variant, or at least a portion of an Fc region of an immunoglobulin.

8. A composition comprising the isolated protein of claim 1 and a pharmaceutically acceptable carrier.

9. A kit comprising the isolated protein of claim 1.

10. A method of detecting CD137-expressing cancer cells in a tumor tissue, comprising
obtaining a sample of the tumor tissue from a subject; and
detecting whether CD137 is expressed in the tumor tissue by contacting the sample of the tumor tissue with an isolated protein comprising the amino acid sequence of one of SEQ ID NOs: 45-51 and 53-224 and detecting the binding between CD137 and the isolated protein.

11. A method of isolating CD137 expressing cells, comprising
obtaining a sample from a subject;
contacting the sample with an isolated protein comprising the amino acid sequence of one of SEQ ID NOs: 45-51 and 53-224, and
isolating the cells bound to the isolated protein.

* * * * *

SEQUENCE LISTING

```
<160> NUMBER OF SEQ ID NOS: 224

<210> SEQ ID NO 1
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60
```

```
Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 2
<211> LENGTH: 94
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (75)..(86)
<223> OTHER INFORMATION: Any amino acid
<220> FEATURE:
<221> NAME/KEY: MISC_FEATURE
<222> LOCATION: (75)..(86)
<223> OTHER INFORMATION: This region may encompass 7-12 residues

<400> SEQUENCE: 2

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
                20                  25                  30

Ile Gln Tyr Gln Glu Ser Glu Lys Val Gly Glu Ala Ile Asn Leu Thr
                35                  40                  45

Val Pro Gly Ser Glu Arg Ser Tyr Asp Leu Thr Gly Leu Lys Pro Gly
            50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Pro Leu Ser Ala Glu Phe Thr Thr
                85                  90

<210> SEQ ID NO 3
<211> LENGTH: 89
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (22)..(27)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (28)..(28)
<223> OTHER INFORMATION: Phe, Ile, Leu, Val or Tyr
<220> FEATURE:
<221> NAME/KEY: MOD_RES
<222> LOCATION: (29)..(29)
<223> OTHER INFORMATION: Asp, Glu or Thr
<220> FEATURE:
<221> NAME/KEY: MOD_RES
<222> LOCATION: (75)..(79)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (81)..(82)
<223> OTHER INFORMATION: Ala, Arg, Asn, Asp, Glu, Gln, Gly, His, Ile,
      Leu, Lys, Phe, Pro, Ser, Thr, Trp, Tyr or Val
```

<400> SEQUENCE: 3

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Ser Phe Leu
            20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val Xaa Xaa Xaa Xaa Ser
65                  70                  75                  80

Xaa Xaa Leu Ser Ala Glu Phe Thr Thr
                85

<210> SEQ ID NO 4
<211> LENGTH: 89
<212> TYPE: PRT
<213> ORGANISM: Artificial Sequence
<220> FEATURE:
<223> OTHER INFORMATION: Synthetic polypeptide

<400> SEQUENCE: 4

Leu Pro Ala Pro Lys Asn Leu Val Val Ser Arg Val Thr Glu Asp Ser
1               5                   10                  15

Ala Arg Leu Ser Trp Thr Ala Pro Ala Ala Phe Asp Ser Phe Leu
            20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85

<210> SEQ ID NO 5
<211> LENGTH: 97
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (22)..(30)
<223> OTHER INFORMATION: Ala, Asp, Glu, Phe, Gly, His, Ile, Lys, Leu,
    Asn, Pro, Gln, Arg, Ser, Thr, Val, Trp or Tyr
<220> FEATURE:
<221> NAME/KEY: MISC_FEATURE
<222> LOCATION: (22)..(30)
<223> OTHER INFORMATION: This region may encompass 6-9 residues
<220> FEATURE:
<221> NAME/KEY: MOD_RES
<222> LOCATION: (78)..(87)
<223> OTHER INFORMATION: Ala, Asp, Glu, Phe, Gly, His, Ile, Lys, Leu,
    Asn, Pro, Gln, Arg, Ser, Thr, Val, Trp or Tyr
<220> FEATURE:
<221> NAME/KEY: MISC_FEATURE
<222> LOCATION: (78)..(87)
<223> OTHER INFORMATION: This region may encompass 7-9 residues

<400> SEQUENCE: 5

Leu Pro Ala Pro Lys Asn Leu Val Val Ser Arg Val Thr Glu Asp Ser
1               5                   10                  15

```
Ala Arg Leu Ser Trp Xaa Xaa Xaa Xaa Xaa Xaa Xaa Xaa Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Xaa Xaa Xaa
65                  70                  75                  80

Xaa Xaa Xaa Xaa Xaa Xaa Xaa Ser Asn Pro Leu Ser Ala Ile Phe Thr
                85                  90                  95

Thr

<210> SEQ ID NO 6
<211> LENGTH: 96
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (75)..(86)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MOD_RES
<222> LOCATION: (75)..(86)
<223> OTHER INFORMATION: This region may encompass 7-12 residues

<400> SEQUENCE: 6

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Ser Asn Pro Leu Ser Ala Ile Phe Thr Thr
                85                  90                  95

<210> SEQ ID NO 7
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (34)..(34)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (36)..(36)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
```

```
<222> LOCATION: (38)..(41)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (68)..(68)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (70)..(70)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (72)..(72)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (78)..(79)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (81)..(81)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met

<400> SEQUENCE: 7

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Xaa Xaa Ser
65                  70                  75                  80

Xaa Pro Leu Ser Ala Ile Phe Thr Thr
                85

<210> SEQ ID NO 8
<211> LENGTH: 89
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (32)..(32)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (34)..(34)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (36)..(36)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (38)..(41)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (46)..(46)
```

```
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (48)..(48)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (68)..(68)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (70)..(70)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (72)..(72)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (78)..(79)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (81)..(81)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (84)..(84)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (86)..(86)
<223> OTHER INFORMATION: Ala, Asp, Glu, Phe, Gly, His, Ile, Lys, Leu,
      Asn, Pro, Gln, Arg, Ser, Thr, Val, Tyr or Trp

<400> SEQUENCE: 8

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Xaa Leu Xaa
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Xaa Ala Xaa Phe Thr Thr
                85

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
gtgacacggc ggttagaac                                              19

<210> SEQ ID NO 10
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 10
gcctttggga agcttctaag                                                      20

<210> SEQ ID NO 11
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 11
cggcggttag aacgcggcta caattaatac                                           30

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
catgattacg ccaagctcag aa                                                   22

<210> SEQ ID NO 13
<211> LENGTH: 385
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (198)..(224)
<223> OTHER INFORMATION: a, c, t, g, unknown or other
<220> FEATURE:
<221> NAME/KEY: misc_feature
<222> LOCATION: (198)..(224)
<223> OTHER INFORMATION: n is a, c, g, or t

<400> SEQUENCE: 13
gtgacacggc ggttagaacg cggctacaat taatacataa ccccatcccc ctgttgacaa          60
ttaatcatcg gctcgtataa tgtgtggaat tgtgagcgga taacaatttc acacaggaaa         120
caggatctac catgctgccg gcgccgaaaa acctggttgt ttctgaagtt accgaagact         180
ctctgcgtct gtcttggnnn nnnnnnnnn nnnnnnnnnn nnnnttygac tctttcctga         240
tccagtacca ggaatctgaa aaagttggtg aagcgatcaa cctgaccgtt ccgggttctg         300
aacgttctta cgacctgacc ggtctgaaac cgggtaccga atacaccgtt tctatctacg         360
gtgttcttag aagcttccca aaggc                                              385

<210> SEQ ID NO 14
<211> LENGTH: 382
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (198)..(221)
<223> OTHER INFORMATION: a, c, t, g, unknown or other
<220> FEATURE:
<221> NAME/KEY: misc_feature
<222> LOCATION: (198)..(221)
<223> OTHER INFORMATION: n is a, c, g, or t
```

<400> SEQUENCE: 14

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctgaagtt accgaagact   180
ctctgcgtct gtcttggnnn nnnnnnnnn nnnnnnnnn nttygactct ttcctgatcc    240
agtaccagga atctgaaaaa gttggtgaag cgatcaacct gaccgttccg ggttctgaac   300
gttcttacga cctgaccggt ctgaaaccgg taccgaata caccgtttct atctacggtg   360
ttcttagaag cttcccaaag gc                                            382
```

<210> SEQ ID NO 15
<211> LENGTH: 379
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (198)..(218)
<223> OTHER INFORMATION: a, c, t, g, unknown or other
<220> FEATURE:
<221> NAME/KEY: misc_feature
<222> LOCATION: (198)..(218)
<223> OTHER INFORMATION: n is a, c, g, or t

<400> SEQUENCE: 15

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctgaagtt accgaagact   180
ctctgcgtct gtcttggnnn nnnnnnnnn nnnnnnntt ygactctttc ctgatccagt    240
accaggaatc tgaaaaagtt ggtgaagcga tcaacctgac cgttccgggt tctgaacgtt   300
cttacgacct gaccggtctg aaaccgggta ccgaatacac cgtttctatc tacggtgttc   360
ttagaagctt cccaaaggc                                                379
```

<210> SEQ ID NO 16
<211> LENGTH: 376
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (198)..(215)
<223> OTHER INFORMATION: a, c, t, g, unknown or other
<220> FEATURE:
<221> NAME/KEY: misc_feature
<222> LOCATION: (198)..(215)
<223> OTHER INFORMATION: n is a, c, g, or t

<400> SEQUENCE: 16

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctgaagtt accgaagact   180
ctctgcgtct gtcttggnnn nnnnnnnnn nnnnttyga ctctttcctg atccagtacc    240
aggaatctga aaaagttggt gaagcgatca acctgaccgt tccgggttct gaacgttctt   300
acgacctgac cggtctgaaa ccgggtaccg aatacaccgt ttctatctac ggtgttctta   360
```
gaagcttccc aaaggc                                                     376

<210> SEQ ID NO 17
<211> LENGTH: 131
<212> TYPE: DNA
<213> ORGANISM: Artificial Sequence
<220> FEATURE:
<223> OTHER INFORMATION: Synthetic polynucleotide

<400> SEQUENCE: 17
cggcggttag aacgcggcta caattaatac ataaccccat cccctgttg acaattaatc      60 atcggctcgt ataatgtgtg gaattgtgag cggataacaa tttcacacag gaaacaggat   120
ctaccatgct g                                                        131

<210> SEQ ID NO 18
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 18
cggcggttag aacgcggcta caattaatac                                      30

<210> SEQ ID NO 19
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 19
ccaagacaga cgggcagagt cttcggtaac gcgagaaaca accaggtttt tcggcgccgg     60
cagcatggta gatcctgttt c                                               81

<210> SEQ ID NO 20
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 20
ccgaagactc tgcccgtctg tcttgg                                          26

<210> SEQ ID NO 21
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 21
cagtggtctc acggattcct ggtactggat caggaaagag tcgaa                     45

<210> SEQ ID NO 22
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 22
catgcggtct cttccgaaaa agttggtgaa gcgatcgtcc tgaccgttcc ggt            54

<210> SEQ ID NO 23
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 23
ggtggtgaag atcgcagaca gcgggttag                               29

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
cggcggttag aacgcggcta c                                       21

<210> SEQ ID NO 25
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 25
aagatcagtt gcggccgcta gactagaacc gctgccaccg ccggtggtga agatcgcaga    60
c                                                                  61

<210> SEQ ID NO 26
<211> LENGTH: 485
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(392)
<223> OTHER INFORMATION: a, c, t, g, unknown or other
<220> FEATURE:
<221> NAME/KEY: misc_feature
<222> LOCATION: (357)..(392)
<223> OTHER INFORMATION: n is a, c, g, or t

<400> SEQUENCE: 26
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360
nnnnnnnnnn nnnnnnnnnn nnnnnnnnnn nntctaaccc gctgtctgcg atcttcacca   420
ccggcggtca ccatcaccat caccatggca gcggttctag tctagcggcc gcaactgatc   480
ttggc                                                              485

<210> SEQ ID NO 27
<211> LENGTH: 482
<212> TYPE: DNA

```
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(389)
<223> OTHER INFORMATION: a, c, t, g, unknown or other
<220> FEATURE:
<221> NAME/KEY: misc_feature
<222> LOCATION: (357)..(389)
<223> OTHER INFORMATION: n is a, c, g, or t

<400> SEQUENCE: 27
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg cgccgaaaa  acctggttgt ttctcgcgtt accgaagact   180
ctgcgcgtct gtcttggacc cgccggacg  cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360
nnnnnnnnnn nnnnnnnnnn nnnnnnnnnt ctaacccgct gtctgcgatc ttcaccaccg   420
gcggtcacca tcaccatcac catggcagcg gttctagtct agcggccgca actgatcttg   480
gc                                                                  482

<210> SEQ ID NO 28
<211> LENGTH: 479
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(386)
<223> OTHER INFORMATION: a, c, t, g, unknown or other
<220> FEATURE:
<221> NAME/KEY: misc_feature
<222> LOCATION: (357)..(386)
<223> OTHER INFORMATION: n is a, c, g, or t

<400> SEQUENCE: 28
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg cgccgaaaa  acctggttgt ttctcgcgtt accgaagact   180
ctgcgcgtct gtcttggacc cgccggacg  cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360
nnnnnnnnnn nnnnnnnnnn nnnnnntcta acccgctgtc tgcgatcttc accaccggcg   420
gtcaccatca ccatcaccat ggcagcggtt ctagtctagc ggccgcaact gatcttggc    479

<210> SEQ ID NO 29
<211> LENGTH: 476
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(383)
<223> OTHER INFORMATION: a, c, t, g, unknown or other
<220> FEATURE:
<221> NAME/KEY: misc_feature
```

<222> LOCATION: (357)..(383)
<223> OTHER INFORMATION: n is a, c, g, or t

<400> SEQUENCE: 29

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn nnntctaacc cgctgtctgc gatcttcacc accggcggtc     420
accatcacca tcaccatggc agcggttcta gtctagcggc cgcaactgat cttggc         476
```

<210> SEQ ID NO 30
<211> LENGTH: 473
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(380)
<223> OTHER INFORMATION: a, c, t, g, unknown or other
<220> FEATURE:
<221> NAME/KEY: misc_feature
<222> LOCATION: (357)..(380)
<223> OTHER INFORMATION: n is a, c, g, or t

<400> SEQUENCE: 30

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn tctaacccgc tgtctgcgat cttcaccacc ggcggtcacc     420
atcaccatca ccatggcagc ggttctagtc tagcggccgc aactgatctt ggc            473
```

<210> SEQ ID NO 31
<211> LENGTH: 470
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (357)..(377)
<223> OTHER INFORMATION: a, c, t, g, unknown or other
<220> FEATURE:
<221> NAME/KEY: misc_feature
<222> LOCATION: (357)..(377)
<223> OTHER INFORMATION: n is a, c, g, or t

<400> SEQUENCE: 31

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
```

```
ctgcgcgtct gtcttggacc gcgccggacg cggcgttcga ctctttcctg atccagtacc    240
aggaatctga aaagttggt gaagcgatcg tgctgaccgt tccgggttct gaacgttctt    300
acgacctgac cggtctgaaa ccgggtaccg aatacaccgt ttctatctac ggtgttnnnn    360
nnnnnnnnnn nnnnnnntct aacccgctgt ctgcgatctt caccaccggc ggtcaccatc    420
accatcacca tggcagcggt tctagtctag cggccgcaac tgatcttggc               470
```

\<210> SEQ ID NO 32
\<211> LENGTH: 88
\<212> TYPE: PRT
\<213> ORGANISM: Unknown
\<220> FEATURE:
\<223> OTHER INFORMATION: 3rd FN3 domain of tenascin C polypeptide

\<400> SEQUENCE: 32

```
Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Glu Leu
            20                  25                  30

Thr Tyr Gly Ile Lys Asp Val Pro Gly Asp Arg Thr Thr Ile Asp Leu
        35                  40                  45

Thr Glu Asp Glu Asn Gln Tyr Ser Ile Gly Asn Leu Lys Pro Asp Thr
    50                  55                  60

Glu Tyr Glu Val Ser Leu Ile Ser Arg Arg Gly Asp Met Ser Ser Asn
65                  70                  75                  80

Pro Ala Lys Glu Thr Phe Thr Thr
                85
```

\<210> SEQ ID NO 33
\<211> LENGTH: 89
\<212> TYPE: PRT
\<213> ORGANISM: Unknown
\<220> FEATURE:
\<223> OTHER INFORMATION: Fibcon polypeptide

\<400> SEQUENCE: 33

```
Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
            20                  25                  30

Ile Thr Tyr Thr Pro Ser Asn Gly Pro Gly Glu Pro Lys Glu Leu Thr
        35                  40                  45

Val Pro Pro Ser Ser Thr Ser Val Thr Ile Thr Gly Leu Thr Pro Gly
    50                  55                  60

Val Glu Tyr Val Val Ser Leu Tyr Ala Leu Lys Asp Asn Gln Glu Ser
65                  70                  75                  80

Pro Pro Leu Val Gly Thr Gln Thr Thr
                85
```

\<210> SEQ ID NO 34
\<211> LENGTH: 94
\<212> TYPE: PRT
\<213> ORGANISM: Unknown
\<220> FEATURE:
\<223> OTHER INFORMATION: 10th FN3 domain of fibronectin polypeptide

\<400> SEQUENCE: 34

```
Val Ser Asp Val Pro Arg Asp Leu Glu Val Val Ala Ala Thr Pro Thr
1               5                   10                  15
```

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 35
<211> LENGTH: 4
<212> TYPE: PRT
<213> ORGANISM: Artificial Sequence
<220> FEATURE:
<223> OTHER INFORMATION: Synthetic peptide

<400> SEQUENCE: 35

Gly Ser Gly Ser
1

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Gly Gly Gly Ser Gly Gly Gly Ser
1               5

<210> SEQ ID NO 37
<211> LENGTH: 25
<212> TYPE: PRT
<213> ORGANISM: Artificial Sequence
<220> FEATURE:
<223> OTHER INFORMATION: Synthetic peptide

<400> SEQUENCE: 37

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 38
<211> LENGTH: 4
<212> TYPE: PRT
<213> ORGANISM: Artificial Sequence
<220> FEATURE:
<223> OTHER INFORMATION: Synthetic peptide

<400> SEQUENCE: 38

Ala Pro Ala Pro
1

<210> SEQ ID NO 39
<211> LENGTH: 10
<212> TYPE: PRT
<213> ORGANISM: Artificial Sequence
<220> FEATURE:
<223> OTHER INFORMATION: Synthetic peptide

<400> SEQUENCE: 39

```
Ala Pro Ala Pro Ala Pro Ala Pro Ala Pro
1               5                  10
```

<210> SEQ ID NO 40
<211> LENGTH: 20
<212> TYPE: PRT
<213> ORGANISM: Artificial Sequence
<220> FEATURE:
<223> OTHER INFORMATION: Synthetic peptide

<400> SEQUENCE: 40

```
Ala Pro Ala Pro Ala Pro Ala Pro Ala Pro Ala Pro Ala Pro Ala Pro
1               5                  10                  15

Ala Pro Ala Pro
            20
```

<210> SEQ ID NO 41
<211> LENGTH: 40
<212> TYPE: PRT
<213> ORGANISM: Artificial Sequence
<220> FEATURE:
<223> OTHER INFORMATION: Synthetic polypeptide

<400> SEQUENCE: 41

```
Ala Pro Ala Pro Ala Pro Ala Pro Ala Pro Ala Pro Ala Pro Ala Pro
1               5                  10                  15

Ala Pro Ala Pro Ala Pro Ala Pro Ala Pro Ala Pro Ala Pro Ala Pro
                20                  25                  30

Ala Pro Ala Pro Ala Pro Ala Pro
            35                  40
```

<210> SEQ ID NO 42
<211> LENGTH: 28
<212> TYPE: PRT
<213> ORGANISM: Artificial Sequence
<220> FEATURE:
<223> OTHER INFORMATION: Synthetic polypeptide

<400> SEQUENCE: 42

```
Glu Ala Ala Ala Lys Glu Ala Ala Ala Lys Glu Ala Ala Ala Lys Glu
1               5                  10                  15

Ala Ala Ala Lys Glu Ala Ala Lys Ala Ala Ala
                20                  25
```

<210> SEQ ID NO 43
<211> LENGTH: 585
<212> TYPE: PRT
<213> ORGANISM: Artificial Sequence
<220> FEATURE:
<223> OTHER INFORMATION: Synthetic polypeptide

<400> SEQUENCE: 43

```
Asp Ala His Lys Ser Glu Val Ala His Arg Phe Lys Asp Leu Gly Glu
1               5                  10                  15

Glu Asn Phe Lys Ala Leu Val Leu Ile Ala Phe Ala Gln Tyr Leu Gln
                20                  25                  30

Gln Ser Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80
```

-continued

```
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
```

```
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
        530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu
            580                 585

<210> SEQ ID NO 44
<211> LENGTH: 255
<212> TYPE: PRT
<213> ORGANISM: Homo sapiens

<400> SEQUENCE: 44

Met Gly Asn Ser Cys Tyr Asn Ile Val Ala Thr Leu Leu Leu Val Leu
1               5                   10                  15
Asn Phe Glu Arg Thr Arg Ser Leu Gln Asp Pro Cys Ser Asn Cys Pro
                20                  25                  30
Ala Gly Thr Phe Cys Asp Asn Asn Arg Asn Gln Ile Cys Ser Pro Cys
            35                  40                  45
Pro Pro Asn Ser Phe Ser Ser Ala Gly Gly Gln Arg Thr Cys Asp Ile
        50                  55                  60
Cys Arg Gln Cys Lys Gly Val Phe Arg Thr Arg Lys Glu Cys Ser Ser
65                  70                  75                  80
Thr Ser Asn Ala Glu Cys Asp Cys Thr Pro Gly Phe His Cys Leu Gly
                85                  90                  95
Ala Gly Cys Ser Met Cys Glu Gln Asp Cys Lys Gln Gly Gln Glu Leu
                100                 105                 110
Thr Lys Lys Gly Cys Lys Asp Cys Cys Phe Gly Thr Phe Asn Asp Gln
            115                 120                 125
Lys Arg Gly Ile Cys Arg Pro Trp Thr Asn Cys Ser Leu Asp Gly Lys
        130                 135                 140
Ser Val Leu Val Asn Gly Thr Lys Glu Arg Asp Val Val Cys Gly Pro
145                 150                 155                 160
Ser Pro Ala Asp Leu Ser Pro Gly Ala Ser Ser Val Thr Pro Pro Ala
                165                 170                 175
Pro Ala Arg Glu Pro Gly His Ser Pro Gln Ile Ile Ser Phe Phe Leu
                180                 185                 190
Ala Leu Thr Ser Thr Ala Leu Leu Phe Leu Leu Phe Phe Leu Thr Leu
            195                 200                 205
Arg Phe Ser Val Val Lys Arg Gly Arg Lys Lys Leu Leu Tyr Ile Phe
        210                 215                 220
Lys Gln Pro Phe Met Arg Pro Val Gln Thr Thr Gln Glu Glu Asp Gly
225                 230                 235                 240
Cys Ser Cys Arg Phe Pro Glu Glu Glu Glu Gly Gly Cys Glu Leu
                245                 250                 255

<210> SEQ ID NO 45
<211> LENGTH: 92
<212> TYPE: PRT
<213> ORGANISM: Artificial Sequence
```

```
<220> FEATURE:
<223> OTHER INFORMATION: CD137 Binding Centyrin

<400> SEQUENCE: 45

Leu Pro Ala Pro Lys Asn Leu Val Val Ser Arg Val Thr Glu Asp Ser
1               5                   10                  15

Ala Arg Leu Ser Trp Asp Phe Ala Tyr Phe Lys Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Gly Arg Phe Tyr Thr Val
65                  70                  75                  80

Tyr Tyr Ser Asn Pro Leu Ser Ala Ile Phe Thr Thr
                85                  90

<210> SEQ ID NO 46
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 46

Leu Pro Ala Pro Lys Asn Leu Val Val Ser Arg Val Thr Glu Asp Ser
1               5                   10                  15

Ala Arg Leu Ser Trp Ser Pro Val Asp Ala Asp Phe Thr Phe Asp Ser
                20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
        50                  55                  60

Pro Gly Thr Glu Tyr Thr Val Ser Ile Tyr Gly Val Gly Arg His Tyr
65                  70                  75                  80

Thr Val Tyr Asp Ser Asn Pro Leu Ser Ala Ile Phe Thr Thr
                85                  90

<210> SEQ ID NO 47
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 47

Leu Pro Ala Pro Lys Asn Leu Val Val Ser Arg Val Thr Glu Asp Ser
1               5                   10                  15

Ala Arg Leu Ser Trp Lys Trp Ile Ser His Glu Pro Leu Glu Phe Asp
                20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
        50                  55                  60

Lys Pro Gly Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
                85                  90                  95
```

```
<210> SEQ ID NO 48
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 48

Leu Pro Ala Pro Lys Asn Leu Val Val Ser Arg Val Thr Glu Asp Ser
1               5                   10                  15

Ala Arg Leu Ser Trp Ala Phe Gln Trp His Ile Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gly Gln Pro Tyr Thr Val
65                  70                  75                  80

Tyr Asp Ser Asn Pro Leu Ser Ala Ile Phe Thr Thr
                85                  90

<210> SEQ ID NO 49
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 49

Leu Pro Ala Pro Lys Asn Leu Val Val Ser Arg Val Thr Glu Asp Tyr
1               5                   10                  15

Ala Arg Leu Ser Trp Lys Tyr Gly Glu His Ile Ile Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Lys Gly Gln His
65                  70                  75                  80

Asp His Asp Ser Asn Pro Leu Ser Ala Ile Phe Thr Thr
                85                  90

<210> SEQ ID NO 50
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 50

Leu Pro Ala Pro Lys Asn Leu Val Val Ser Arg Val Thr Glu Asp Ser
1               5                   10                  15

Ala Arg Leu Ser Trp Thr Leu Pro Asn Ile His Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gly Arg His Tyr Thr Val
```

```
                65                  70                  75                  80
Tyr Asp Ser Asn Pro Leu Ser Ala Ile Phe Thr Thr
                    85                  90

<210> SEQ ID NO 51
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 51

Leu Pro Ala Pro Lys Asn Leu Val Val Ser Arg Val Thr Glu Asp Ser
1               5                   10                  15

Ala Arg Leu Ser Trp Ser Gln His Tyr Leu Ser Pro Ile Pro Phe Asp
                20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
        50                  55                  60

Lys Pro Gly Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
                85                  90                  95

<210> SEQ ID NO 52
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 52

Leu Pro Ala Pro Lys Asn Leu Val Val Ser Arg Val Thr Glu Asp Ser
1               5                   10                  15

Ala Arg Leu Ser Trp His Ala Thr Phe Gly Asp Pro Phe Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val Gly Arg His Tyr Thr
65                  70                  75                  80

Val Tyr Asp Ser Asn Pro Leu Ser Ala Ile Phe Thr Thr
                85                  90

<210> SEQ ID NO 53
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 53

Leu Pro Ala Pro Lys Asn Leu Val Val Ser Arg Val Thr Glu Asp Ser
1               5                   10                  15

Ala Arg Leu Ser Trp Asn Thr Asp Trp Val His Thr Phe Asp Ser Phe
                20                  25                  30

Leu Ile Gln Tyr Gln Glu Ser Glu Lys Val Gly Glu Ala Ile Val Leu
            35                  40                  45
```

```
Thr Val Pro Gly Ser Glu Arg Ser Tyr Asp Leu Thr Gly Leu Lys Pro
            50                  55                  60

Gly Thr Glu Tyr Thr Val Ser Ile Tyr Gly Val Gly Arg His Tyr Thr
 65                  70                  75                  80

Val Tyr Asp Ser Asn Pro Leu Ser Ala Ile Phe Thr Thr
                 85                  90
```

<210> SEQ ID NO 54
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 54

```
Leu Pro Ala Pro Lys Asn Leu Val Val Ser Arg Val Thr Glu Asp Ser
 1               5                  10                  15

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Ala Thr Glu Tyr Thr Val Ser Ile Tyr Gly Val Gly Arg His
 65                  70                  75                  80

Tyr Thr Val Tyr Asp Ser Asn Pro Leu Ser Ala Ile Phe Thr Thr
                 85                  90                  95
```

<210> SEQ ID NO 55
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 55

```
Leu Pro Ala Pro Lys Asn Leu Val Val Ser Arg Val Thr Glu Asp Ser
 1               5                  10                  15

Ala Arg Leu Ser Trp Asp Gly Asp Lys Trp Ala Asn Phe Lys Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Leu His
 65                  70                  75                  80

Tyr Ile Val Tyr Asp Ser Asn Pro Leu Ser Ala Ile Phe Thr Thr
                 85                  90                  95
```

<210> SEQ ID NO 56
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 56

```
Leu Pro Ala Pro Lys Asn Leu Val Val Ser Arg Val Thr Glu Asp Ser
 1               5                  10                  15
```

Ala Arg Leu Ser Trp Val Arg Glu Asp Ala Tyr Ala Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Thr Val Ser Ile Tyr Gly Val Ser Ser Leu His Trp
65                  70                  75                  80

Val Val His Asp Ser Asn Pro Leu Ser Ala Ile Phe Thr Thr
                85                  90

<210> SEQ ID NO 57
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 57

Leu Pro Ala Pro Lys Asn Leu Val Val Ser Arg Val Thr Glu Asp Ser
1               5                   10                  15

Ala Arg Leu Ser Trp Thr Phe His Pro Thr Phe Glu Gly Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Lys Trp Thr Val
65                  70                  75                  80

Leu Arg Pro Trp Leu Ser Asn Pro Leu Ser Ala Ile Phe Thr Thr
                85                  90                  95

<210> SEQ ID NO 58
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 58

Leu Pro Ala Pro Lys Asn Leu Val Val Ser Arg Val Thr Glu Asp Ser
1               5                   10                  15

Ala Arg Leu Ser Trp Ile Arg Lys His Asn His Val Lys Trp Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Phe Leu
65                  70                  75                  80

Ile Asp Thr Asp Asp Ser Asn Pro Leu Ser Ala Ile Phe Thr Thr
                85                  90                  95

<210> SEQ ID NO 59
<211> LENGTH: 93
<212> TYPE: PRT
<213> ORGANISM: Artificial Sequence
<220> FEATURE:
<223> OTHER INFORMATION: CD137 Binding Centyrin -continued

```
<400> SEQUENCE: 59

Leu Pro Ala Pro Lys Asn Leu Val Val Ser Arg Val Thr Glu Asp Ser
1               5                   10                  15

Ala Arg Leu Ser Trp Ala Gln Glu Leu Asp His Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Tyr Trp Thr Trp Trp Val
65                  70                  75                  80

Arg Trp Asn Ser Asn Pro Leu Ser Ala Ile Phe Thr Thr
                85                  90

<210> SEQ ID NO 60
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 60

Leu Pro Ala Pro Lys Asn Leu Val Val Ser Arg Val Thr Glu Asp Ser
1               5                   10                  15

Ala Arg Leu Ser Trp Thr Phe His Pro Thr Phe Glu Gly Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Lys Trp Tyr Ala
65                  70                  75                  80

Gly Ile Gly Tyr Pro Val Ser Asn Pro Leu Ser Ala Ile Phe Thr Thr
                85                  90                  95

<210> SEQ ID NO 61
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 61

Leu Pro Ala Pro Lys Asn Leu Val Val Ser Arg Val Thr Glu Asp Ser
1               5                   10                  15

Ala Arg Leu Ser Trp Ser Glu His Pro Thr Pro Phe Ala Thr Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Trp Trp Val
65                  70                  75                  80

Glu Asn His Phe Pro Val Ser Asn Pro Leu Ser Ala Ile Phe Thr Thr
                85                  90                  95

<210> SEQ ID NO 62
<211> LENGTH: 94
```

```
<212> TYPE: PRT
<213> ORGANISM: Artificial Sequence
<220> FEATURE:
<223> OTHER INFORMATION: CD137 Binding Centyrin

<400> SEQUENCE: 62

Leu Pro Ala Pro Lys Asn Leu Val Val Ser Arg Val Thr Glu Asp Ser
1               5                   10                  15

Ala Arg Leu Ser Trp Glu Glu Ser Arg Gln Phe Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Val His Arg Ala Trp Leu
65                  70                  75                  80

Arg Trp Asn Gly Ser Asn Pro Leu Ser Ala Ile Phe Thr Thr
                85                  90

<210> SEQ ID NO 63
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 63

Leu Pro Ala Pro Lys Asn Leu Val Val Ser Arg Val Thr Glu Asp Ser
1               5                   10                  15

Ala Arg Leu Ser Trp Asp Asp Gln Phe Glu Asp Trp Phe Asp Ser Phe
            20                  25                  30

Leu Ile Gln Tyr Gln Glu Ser Glu Gln Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Thr Arg Asp Trp
65                  70                  75                  80

Thr Ala Trp Asn Ala Ser Asn Pro Leu Ser Ala Ile Phe Thr Thr
                85                  90                  95

<210> SEQ ID NO 64
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 64

Leu Pro Ala Pro Lys Asn Leu Val Val Ser Arg Val Thr Glu Asp Ser
1               5                   10                  15

Ala Arg Leu Ser Trp Ala Gly His Tyr Arg Lys Ile Arg Asn Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Lys Phe Pro
65                  70                  75                  80

Tyr Tyr Tyr Ala Thr Ala Asp Ser Asn Pro Leu Ser Ala Ile Phe Thr
```

-continued

```
                85                  90                  95

Thr

<210> SEQ ID NO 65
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 65

Leu Pro Ala Pro Lys Asn Leu Val Val Ser Arg Val Thr Glu Asp Ser
1               5                   10                  15

Ala Arg Leu Ser Trp Ala Gly His Tyr Arg Lys Ile Arg Asn Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Lys Arg Ser Tyr Asp Leu Thr Gly Leu
    50                  55                  60

Lys Pro Gly Thr Glu Tyr Thr Val Ser Ile Tyr Gly Val Lys Phe Pro
65                  70                  75                  80

Tyr Tyr Tyr Ala Thr Ala Asp Ser Asn Pro Leu Ser Ala Ile Phe Thr
                85                  90                  95

Thr

<210> SEQ ID NO 66
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 66

Leu Pro Ala Pro Lys Asn Leu Val Val Ser Arg Val Thr Glu Asp Ser
1               5                   10                  15

Ala Arg Leu Ser Trp Leu Glu Gly Ala Asn Ala Glu Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val His Trp Val Gly Pro
65                  70                  75                  80

Trp Tyr Pro Val Ser Asn Pro Leu Ser Ala Ile Phe Thr Thr
                85                  90

<210> SEQ ID NO 67
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 67

Leu Pro Ala Pro Lys Asn Leu Val Val Ser Arg Val Thr Glu Asp Ser
1               5                   10                  15

Ala Arg Leu Ser Trp Gly Ala Lys Thr Arg Gln Phe Asp Ser Phe Leu
            20                  25                  30

Ile Gln Tyr Gln Glu Ser Glu Lys Val Gly Glu Ala Ile Val Leu Thr
```

35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Trp Trp Val Glu Asn His
65                  70                  75                  80

Phe Pro Val Ser Asn Pro Leu Ser Ala Ile Phe Thr Thr
                85                  90

<210> SEQ ID NO 68
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 68

Leu Pro Ala Pro Lys Asn Leu Val Val Ser Arg Val Thr Glu Asp Ser
1               5                   10                  15

Ala Arg Leu Ser Trp Asn Val Thr Gln Lys Glu Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gly Asn Arg Tyr Tyr Thr
65                  70                  75                  80

Val Tyr Asp Ser Asn Pro Leu Ser Ala Ile Phe Thr Thr
                85                  90

<210> SEQ ID NO 69
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 69

Leu Pro Ala Pro Lys Asn Leu Val Val Ser Arg Val Thr Glu Asp Ser
1               5                   10                  15

Ala Arg Leu Ser Trp Lys Asn His Thr Gln Glu Trp Glu Phe Asp Ser
                20                  25                  30

Phe Leu Ile Gln Tyr Gln Glu Ser Glu Lys Val Gly Glu Ala Ile Val
            35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Pro Ile Ala Trp
65                  70                  75                  80

Leu Ala Trp Thr Ser Thr Ser Asn Pro Leu Ser Ala Ile Phe Thr Thr
                85                  90                  95

<210> SEQ ID NO 70
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 70

Leu Pro Ala Pro Lys Asn Leu Val Val Ser Arg Val Thr Glu Asp Ser
1               5                   10                  15

-continued

Ala Arg Leu Ser Trp Asn Gly Gly Glu Tyr Trp Val Pro Arg Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
50                  55                  60

Lys Pro Gly Thr Glu Tyr Thr Val Ser Ile Tyr Gly Val Val Trp Leu
65                  70                  75                  80

Gln Trp Ile Ser Trp Thr Asp Ser Asn Pro Leu Ser Ala Ile Phe Thr
                85                  90                  95

Thr

<210> SEQ ID NO 71
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 71

Leu Pro Ala Pro Lys Asn Leu Val Val Ser Arg Val Thr Glu Asp Ser
1               5                   10                  15

Ala Arg Leu Ser Trp Ala Val Glu Phe Asn Pro Thr Lys Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
50                  55                  60

Pro Gly Thr Glu Tyr Thr Val Ser Ile Tyr Gly Val Trp Trp Phe Glu
65                  70                  75                  80

Gln Trp Tyr Pro Val Ser Asn Pro Leu Ser Ala Ile Phe Thr Thr
                85                  90                  95

<210> SEQ ID NO 72
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 72

Leu Pro Ala Pro Lys Asn Leu Val Val Ser Arg Val Thr Glu Asp Ser
1               5                   10                  15

Ala Arg Leu Ser Trp Ala Trp Asn Arg His Asp Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val His Trp Thr Val Leu Arg
65                  70                  75                  80

Pro Phe Ile Asp Ser Asn Pro Leu Ser Ala Ile Phe Thr Thr
                85                  90

<210> SEQ ID NO 73
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 73

Leu Pro Ala Pro Lys Asn Leu Val Val Ser Arg Val Thr Glu Asp Ser
1               5                   10                  15

Ala Arg Leu Ser Trp Thr Ile Asn Ser His Ile Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Trp Gly Thr Lys Tyr Trp
65                  70                  75                  80

Gln Ala Gln Ser Asn Pro Leu Ser Ala Ile Phe Thr Thr
                85                  90

<210> SEQ ID NO 74
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 74

Leu Pro Ala Pro Lys Asn Leu Val Val Ser Arg Val Thr Glu Asp Ser
1               5                   10                  15

Ala Arg Leu Ser Trp Thr Glu Glu Asp Ile Thr His Leu Arg Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Tyr Trp Thr
65                  70                  75                  80

Trp Trp Val Arg Trp Asn Ser Asn Pro Leu Ser Ala Ile Phe Thr Thr
                85                  90                  95

<210> SEQ ID NO 75
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 75

Leu Pro Ala Pro Lys Asn Leu Val Val Ser Arg Val Thr Glu Asp Ser
1               5                   10                  15

Ala Arg Leu Ser Trp Thr Lys Arg His Phe Tyr Thr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Tyr Leu Thr Gly Leu Lys Pro
    50                  55                  60

Gly Thr Glu Asn Thr Val Ser Ile Tyr Gly Val His Gly Asn His Pro
65                  70                  75                  80

Tyr Thr Asp Ala Pro Ala Asn Pro Leu Ser Ala Ile Phe Thr Thr
                85                  90                  95

<210> SEQ ID NO 76
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 76

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Gln Tyr Ala Glu Asp Ser Ser Trp Gly Glu Ala Ile Asn Leu His
        35                  40                  45

Val Pro Gly Ser Glu Arg Ser Tyr Asp Leu Thr Gly Leu Lys Pro Gly
    50                  55                  60

Thr Glu Tyr His Val His Ile Tyr Gly Val Lys Gly Gly Glu Ala Ser
65                  70                  75                  80

Asn Pro Leu Trp Ala Trp Phe Thr Thr
                85
```

<210> SEQ ID NO 77
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 77

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Arg Tyr Trp Glu Phe Cys His Ser Gly Glu Ala Ile Glu Leu Ser
        35                  40                  45

Val Pro Gly Ser Glu Arg Ser Tyr Asp Leu Thr Gly Leu Lys Pro Gly
    50                  55                  60

Thr Glu Tyr Phe Val Arg Ile Val Gly Val Lys Gly Gly Arg Val Ser
65                  70                  75                  80

Leu Pro Leu Gly Ala Lys Phe Thr Thr
                85
```

<210> SEQ ID NO 78
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 78

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Asp Tyr Trp Glu Val Glu Ser Glu Gly Glu Ala Ile Val Leu Phe
        35                  40                  45

Val Pro Gly Ser Glu Arg Ser Tyr Asp Leu Thr Gly Leu Lys Pro Gly
    50                  55                  60

Thr Glu Tyr His Val His Ile Val Gly Val Lys Gly Gly Thr Pro Ser
```

```
                65                  70                  75                  80
Tyr Pro Leu Trp Ala Asp Phe Thr Thr
                                85

<210> SEQ ID NO 79
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 79

Leu Pro Ala Pro Lys Asn Leu Val Val Ser Arg Val Thr Glu Asp Ser
1               5                   10                  15

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
                85                  90                  95

<210> SEQ ID NO 80
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 80

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Asp Tyr Trp Glu Val Glu Ser Glu Gly Glu Ala Ile Ile Leu Phe
        35                  40                  45

Val Pro Gly Ser Glu Arg Ser Tyr Asp Leu Thr Gly Leu Lys Pro Gly
    50                  55                  60

Thr Glu Tyr His Val His Ile Val Gly Val Lys Gly Thr Pro Ser
65                  70                  75                  80

Tyr Pro Leu Trp Ala Asp Phe Thr Thr
                85

<210> SEQ ID NO 81
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 81

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Pro Tyr Ile Glu Val Glu Thr Ile Gly Glu Ala Ile Trp Leu His
        35                  40                  45
```

Val Pro Gly Ser Glu Arg Ser Tyr Asp Leu Thr Gly Leu Lys Pro Gly
    50                  55                  60

Thr Glu Tyr Ser Val Gly Ile Asn Gly Val Lys Gly Gly His Thr Ser
65                  70                  75                  80

Asn Pro Leu Ser Ala Arg Phe Thr Thr
                85

<210> SEQ ID NO 82
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 82

Leu Pro Ala Pro Lys Asn Leu Val Val Ser Arg Val Thr Glu Asp Ser
1               5                   10                  15

Ala Arg Leu Ser Trp Thr Ala Pro Asp Gly Ala Phe Asp Ser Phe Glu
                20                  25                  30

Ile Pro Tyr Ile Glu Val Glu Thr Ile Gly Glu Ala Ile Trp Leu His
            35                  40                  45

Val Pro Gly Ser Glu Arg Ser Tyr Asp Leu Thr Gly Leu Lys Pro Gly
    50                  55                  60

Thr Glu Tyr Ser Val Gly Ile Asn Gly Val Lys Gly Gly His Thr Ser
65                  70                  75                  80

Asn Pro Leu Ser Ala Arg Phe Thr Thr
                85

<210> SEQ ID NO 83
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 83

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
                20                  25                  30

Ile Pro Tyr Trp Glu Trp Thr Thr Glu Gly Glu Ala Ile Gln Leu Ile
            35                  40                  45

Val Pro Gly Ser Glu Arg Ser Tyr Asp Leu Thr Gly Leu Lys Pro Ala
    50                  55                  60

Thr Glu Tyr His Val His Ile Val Gly Val Lys Gly Gly Ser Phe Ser
65                  70                  75                  80

Glu Pro Leu Pro Ala Asp Phe Thr Thr
                85

<210> SEQ ID NO 84
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 84

Leu Pro Ala Pro Lys Asn Leu Val Val Ser Arg Val Thr Glu Asp Ser
1               5                   10                  15

```
Ala Arg Leu Ser Trp Thr Ala Pro Asp Ala Ala Phe Asp Ser Phe Asn
            20                  25                  30

Ile Lys Tyr Trp Glu Ala Asn Leu Tyr Gly Glu Ala Ile Val Leu Thr
        35                  40                  45

Val Pro Gly Ser Glu Arg Ser Tyr Gly Leu Thr Gly Leu Lys Pro Gly
    50                  55                  60

Thr Glu Tyr Arg Val His Ile Arg Gly Val Lys Gly Ile Asn Ser
65                  70                  75                  80

Phe Pro Leu Val Ala Val Phe Thr Thr
                85
```

<210> SEQ ID NO 85
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 85

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
            20                  25                  30

Ile Ala Tyr Trp Glu Tyr Trp Gly Asn Gly Glu Ala Ile Gly Leu Ile
        35                  40                  45

Val Pro Gly Ser Glu Arg Ser Tyr Asp Leu Thr Gly Leu Lys Pro Gly
    50                  55                  60

Thr Glu Tyr His Val His Ile Val Gly Val Lys Gly Gly Ala Gly Ser
65                  70                  75                  80

Val Pro Leu Trp Ala Asn Phe Thr Thr
                85
```

<210> SEQ ID NO 86
<211> LENGTH: 88
<212> TYPE: PRT
<213> ORGANISM: Artificial Sequence
<220> FEATURE:
<223> OTHER INFORMATION: CD137 Binding Centyrin

<400> SEQUENCE: 86

```
Leu Pro Ala Pro Lys Asn Leu Val Val Ser His Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Leu Glu Gly Gly Arg Gly Glu Ala Ile Val Leu Thr Val
        35                  40                  45

Pro Gly Ser Glu Arg Ser Tyr Asp Leu Thr Val Leu Lys Pro Gly Thr
    50                  55                  60

Glu Tyr Leu Gly Thr Ile Tyr Gly Val Lys Cys Gly Trp Ala Ser Asn
65                  70                  75                  80

Pro Leu Ser Ala Ile Phe Thr Thr
                85
```

<210> SEQ ID NO 87
<211> LENGTH: 89
<212> TYPE: PRT
<213> ORGANISM: Artificial Sequence
<220> FEATURE:
<223> OTHER INFORMATION: CD137 Binding Centyrin -continued

<400> SEQUENCE: 87

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Ala Glu Phe Gly Tyr Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Thr Ile Tyr Gly Val Lys Gly Gly Trp Tyr Ser
65                  70                  75                  80

Thr Pro Leu Ser Ala Ile Phe Thr Thr
                85

<210> SEQ ID NO 88
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 88

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Tyr Tyr Gly Glu Tyr Tyr Asn Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Thr Ile Tyr Gly Val Lys Gly Gly Gly Tyr Ser
65                  70                  75                  80

Asn Pro Leu Ser Ala Ile Phe Thr Thr
                85

<210> SEQ ID NO 89
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 89

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Arg Glu Tyr Trp Tyr Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Trp Tyr Ser
65                  70                  75                  80

Asp Pro Leu Ser Ala Ile Phe Thr Thr
                85

<210> SEQ ID NO 90
<211> LENGTH: 89

```
<212> TYPE: PRT
<213> ORGANISM: Artificial Sequence
<220> FEATURE:
<223> OTHER INFORMATION: CD137 Binding Centyrin

<400> SEQUENCE: 90

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Leu Tyr Leu Glu Pro Tyr Gln Glu Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Tyr Tyr Ser
65                  70                  75                  80

Leu Pro Leu Ser Ala Ile Phe Thr Thr
                85

<210> SEQ ID NO 91
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 91

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
                20                  25                  30

Ile Arg Tyr Ile Glu Glu Gly Tyr Tyr Gly Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr His Val Gly Ile Glu Gly Val Lys Gly Gly Tyr Tyr Ser
65                  70                  75                  80

Tyr Pro Leu Ser Ala Ile Phe Thr Thr
                85

<210> SEQ ID NO 92
<211> LENGTH: 88
<212> TYPE: PRT
<213> ORGANISM: Artificial Sequence
<220> FEATURE:
<223> OTHER INFORMATION: CD137 Binding Centyrin

<400> SEQUENCE: 92

Leu Pro Ala Pro Lys Asn Leu Val Val Ser Arg Val Thr Glu Asp Ser
1               5                   10                  15

Ala Arg Leu Ser Trp Thr Ala Pro Asp Gly Ala Phe Asp Ser Phe Glu
                20                  25                  30

Ile Tyr Tyr Leu Glu Gly Gly Arg Gly Glu Ala Ile Val Leu Thr Val
            35                  40                  45

Pro Gly Ser Glu Arg Ser Tyr Asp Leu Thr Gly Leu Lys Pro Gly Thr
    50                  55                  60

Glu Tyr Leu Val Thr Ile Tyr Gly Ile Lys Cys Gly Trp Ala Ser Asn
65                  70                  75                  80

Pro Leu Ser Ala Ile Phe Thr Thr
```

<210> SEQ ID NO 93
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 93

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Phe Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Leu Asp Ser
65                  70                  75                  80

Gln Pro Leu Ser Ala Ile Phe Thr Thr
            85

<210> SEQ ID NO 94
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 94

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Ala Glu Pro Arg Tyr Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Thr Ile Tyr Gly Val Lys Gly Gly Tyr Tyr Ser
65                  70                  75                  80

Ser Pro Leu Ser Ala Ile Phe Thr Thr
            85

<210> SEQ ID NO 95
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 95

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Leu Glu Ser Trp Thr Arg Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Ser Tyr Ser
65                  70                  75                  80

Arg Pro Leu Ser Ala Ile Phe Thr Thr
                85

<210> SEQ ID NO 96
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 96

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Tyr Tyr Leu Glu Gln Leu Gly Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Val Cys Glu Gln Ser
65                  70                  75                  80

Tyr Pro Leu Ser Ala Ile Phe Thr Thr
                85

<210> SEQ ID NO 97
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 97

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Gly Glu Pro Gly Asn Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Asp Tyr Ser
65                  70                  75                  80

Ser Pro Leu Ser Ala Ile Phe Thr Thr
                85

<210> SEQ ID NO 98
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 98

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Tyr Tyr Ser
 65                  70                  75                  80

Gly Pro Leu Ser Ala Ile Phe Thr Thr
                 85

<210> SEQ ID NO 99
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 99

Leu Pro Ala Pro Lys Asn Leu Val Val Ser Arg Val Thr Glu Asp Ser
 1               5                   10                  15

Ala Arg Leu Ser Trp Thr Ala Pro Asp Ala Ala Phe Asp Ser Phe Asp
                 20                  25                  30

Ile Tyr Tyr Arg Glu Leu Asp Phe Gln Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Leu Val Ile Ile Tyr Gly Val Lys Gly Ser Tyr Ser
 65                  70                  75                  80

Tyr Thr Leu Ser Ala Ile Phe Thr Thr
                 85

<210> SEQ ID NO 100
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 100

Leu Pro Ala Pro Lys Asn Leu Val Val Ser Arg Val Thr Glu Asp Ser
 1               5                   10                  15

Ala Arg Leu Ser Trp Thr Ala Pro Asp Ala Ala Phe Asp Ser Phe Tyr
                 20                  25                  30

Ile Tyr Tyr Arg Glu His Trp Thr Ile Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Gly Ala Tyr Ser
 65                  70                  75                  80

Asn Pro Leu Ser Ala Ile Phe Thr Thr
                 85

<210> SEQ ID NO 101
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 101

Leu Pro Ala Pro Lys Asn Leu Val Val Ser Arg Val Thr Glu Asp Ser

```
                1               5                  10                 15
Ala Arg Leu Ser Trp Thr Ala Pro Asp Ala Ala Phe Asp Ser Phe Ser
                20                 25                 30

Ile Leu Tyr Gly Glu Pro Ala Leu Gly Glu Ala Ile Val Leu Thr
                35                 40                 45

Val Pro Gly Ser Glu Arg Ser Tyr Asp Leu Thr Gly Leu Lys Pro Gly
        50                 55                 60

Thr Glu Tyr Trp Val Thr Ile Tyr Gly Val Lys Gly Val Phe Ser
65                 70                 75                 80

His Pro Leu Ser Ala Ile Phe Thr Thr
                85

<210> SEQ ID NO 102
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 102

Leu Pro Ala Pro Lys Asn Leu Val Val Ser Arg Val Thr Glu Asp Ser
1               5                  10                 15

Ala Arg Leu Ser Trp Thr Ala Pro Asp Ala Ala Phe Asp Ser Phe Val
                20                 25                 30

Ile Arg Tyr Ile Glu Asp Thr Val Met Gly Glu Ala Ile Val Leu Thr
                35                 40                 45

Val Pro Gly Ser Glu Arg Ser Tyr Asp Leu Thr Gly Leu Lys Pro Gly
        50                 55                 60

Thr Glu Tyr His Val Ser Ile Glu Gly Val Lys Gly Pro Ser Ser
65                 70                 75                 80

Leu Pro Leu Ser Ala Ile Phe Thr Thr
                85

<210> SEQ ID NO 103
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 103

Leu Pro Ala Pro Lys Asn Leu Val Val Ser Arg Val Thr Glu Asp Ser
1               5                  10                 15

Ala Arg Leu Ser Trp Thr Ala Pro Asp Ala Ala Phe Asp Ser Phe Asn
                20                 25                 30

Ile Met Tyr Leu Glu Asp Val Gln Cys Gly Glu Ala Ile Val Leu Thr
                35                 40                 45

Val Pro Gly Ser Glu Arg Ser Tyr Asp Leu Thr Gly Leu Lys Pro Gly
        50                 55                 60

Thr Glu Tyr His Val Gly Ile Asn Gly Val Lys Gly Gly Leu Arg Ser
65                 70                 75                 80

Phe Pro Leu Ser Ala Ile Phe Thr Thr
                85

<210> SEQ ID NO 104
<211> LENGTH: 89
<212> TYPE: PRT
<213> ORGANISM: Artificial Sequence
<220> FEATURE:
```

<223> OTHER INFORMATION: CD137 Binding Centyrin

<400> SEQUENCE: 104

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Ser Tyr Leu Glu Asp Val Tyr Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr His Val Gly Ile His Gly Val Lys Gly Gly Ile Asp Ser
65                  70                  75                  80

Phe Pro Leu Ser Ala Ile Phe Thr Thr
                85

<210> SEQ ID NO 105
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 105

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Gly Glu His Trp Lys Leu Gly Glu Ala Ile Val Leu Thr
        35                  40                  45

Val Gln Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Gln Trp Ser
65                  70                  75                  80

Phe Pro Leu Ser Ala Ile Phe Thr Thr
                85

<210> SEQ ID NO 106
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 106

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
            20                  25                  30

Ile Tyr Tyr Gly Glu Trp His Ala Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Val Val Thr Ile Tyr Gly Val Lys Gly Gly Thr Tyr Ser
65                  70                  75                  80

Leu Pro Leu Ser Ala Ile Ser Thr Thr
                85

```
<210> SEQ ID NO 107
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 107

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
                20                  25                  30

Ile Tyr Tyr Gly Glu Trp His Ala Leu Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Val Val Thr Ile Tyr Gly Val Lys Gly Thr Tyr Ser
65                  70                  75                  80

Leu Pro Leu Ser Ala Ile Phe Thr Thr
                85

<210> SEQ ID NO 108
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 108

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
                20                  25                  30

Ile Gly Tyr Tyr Glu Arg Ile Ile Pro Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Ser Val Leu Ile Cys Gly Val Lys Gly Gly Lys Gly Ser
65                  70                  75                  80

Ile Pro Leu Ser Ala Ile Phe Thr Thr
                85

<210> SEQ ID NO 109
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 109

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Phe Glu His Pro Val Gly Gly Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Tyr Leu Ser
65                  70                  75                  80
```

```
Met Pro Leu Ser Ala Ile Phe Thr Thr
                85

<210> SEQ ID NO 110
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 110

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Met Glu Asp Phe His Ser Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Thr Ile Tyr Gly Val Glu Gly Thr Gly Ser
65                  70                  75                  80

Leu Pro Leu Ser Ala Ile Phe Thr Thr
                85

<210> SEQ ID NO 111
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 111

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Lys Glu Leu Arg Ala Glu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Ser Val Ser
65                  70                  75                  80

Ile Pro Leu Ser Ala Ile Phe Thr Thr
                85

<210> SEQ ID NO 112
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 112

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Tyr Tyr Ile Glu Trp Thr Ala Tyr Gly Glu Ala Ile Val Leu Thr
        35                  40                  45
```

Val Pro Gly Ser Glu Arg Ser Tyr Asp Leu Thr Gly Leu Lys Pro Gly
            50                  55                  60

Thr Glu Tyr Val Val Arg Ile Ser Gly Val Lys Cys Gly Ile Val Ser
65                  70                  75                  80

Phe Pro Leu Ser Ala Ile Phe Thr Thr
                85

<210> SEQ ID NO 113
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 113

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Tyr Tyr Phe Glu Asn Glu Asn Gly Gly Glu Ala Ile Val Leu Thr
        35                  40                  45

Val Pro Gly Ser Glu Arg Ser Tyr Asp Leu Thr Gly Leu Lys Pro Gly
            50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 114
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 114

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Asn Tyr Phe Glu Gln Pro Lys Gly Gly Glu Ala Ile Val Leu Thr
        35                  40                  45

Val Pro Gly Ser Glu Arg Ser Tyr Asp Leu Thr Gly Leu Lys Pro Gly
            50                  55                  60

Thr Glu Tyr Leu Val Thr Ile Tyr Gly Val Lys Gly Gly Pro Tyr Ser
65                  70                  75                  80

Pro Pro Leu Ser Ala Ile Phe Thr Thr
                85

<210> SEQ ID NO 115
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 115

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Leu Gln

```
                20                  25                  30
Ile Tyr Tyr Phe Glu Trp Val Val Gly Gly Glu Ala Ile Val Leu Thr
            35                  40                  45
Val Pro Gly Ser Glu Arg Ser Tyr Asp Leu Thr Gly Leu Lys Leu Gly
        50                  55                  60
Thr Glu Tyr Leu Val Thr Ile Tyr Gly Val Lys Gly Gly Asn Phe Ser
65                  70                  75                  80
Asp Pro Leu Ser Ala Ile Phe Thr Thr
                85

<210> SEQ ID NO 116
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 116

Leu Pro Ala Pro Lys Asn Leu Val Val Ser Arg Val Thr Glu Asp Ser
1               5                   10                  15
Ala Arg Leu Ser Trp Thr Ala Pro Asp Ala Ala Phe Asp Ser Phe Ile
            20                  25                  30
Ile Arg Tyr Leu Glu Asp Ile Ser Tyr Gly Glu Ala Ile Val Leu Thr
        35                  40                  45
Val Pro Gly Ser Glu Arg Ser Tyr Asp Leu Thr Gly Leu Lys Pro Gly
    50                  55                  60
Thr Glu Tyr His Val Gly Ile Glu Gly Val Lys Gly Gly Asn Val Ser
65                  70                  75                  80
Phe Pro Leu Ser Ala Ile Phe Thr Thr
                85

<210> SEQ ID NO 117
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 117

Leu Pro Ala Pro Lys Asn Leu Val Val Ser Arg Val Thr Glu Asp Ser
1               5                   10                  15
Ala Arg Leu Ser Trp Thr Ala Pro Asp Ala Ala Phe Asp Ser Phe Gly
            20                  25                  30
Ile Pro Tyr Leu Glu Asp Ile Glu Val Gly Glu Ala Ile Val Leu Thr
        35                  40                  45
Val Pro Gly Ser Glu Arg Ser Tyr Asp Leu Ala Gly Leu Lys Pro Gly
    50                  55                  60
Thr Glu Tyr His Val Gly Ile Tyr Gly Val Lys Gly Gly Glu Gln Ser
65                  70                  75                  80
Phe Pro Leu Ser Ala Ile Phe Thr Thr
                85

<210> SEQ ID NO 118
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 118
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Arg Tyr Leu Glu Asp Ile Ser Tyr Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Gly Ile Glu Gly Val Lys Gly Gly Asn Val Ser
65                  70                  75                  80

Trp Pro Leu Ser Ala Ile Phe Thr Thr
                85

<210> SEQ ID NO 119
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 119

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Arg Tyr Leu Glu Asp Ile Ser Tyr Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Gly Ile Glu Gly Val Lys Gly Gly Asn Val Ser
65                  70                  75                  80

Trp Pro Leu Ser Ala Ile Phe Thr Thr
                85

<210> SEQ ID NO 120
<211> LENGTH: 87
<212> TYPE: PRT
<213> ORGANISM: Artificial Sequence
<220> FEATURE:
<223> OTHER INFORMATION: CD137 Binding Centyrin

<400> SEQUENCE: 120

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Tyr Tyr Pro Glu Tyr Ile Ser Asn Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Thr Ile Gly Val Lys Gly Gly His Ser Trp Pro
65                  70                  75                  80

Leu Ser Ala Ile Phe Thr Thr
                85

<210> SEQ ID NO 121
<211> LENGTH: 88
<212> TYPE: PRT

<213> ORGANISM: Artificial Sequence
<220> FEATURE:
<223> OTHER INFORMATION: CD137 Binding Centyrin

<400> SEQUENCE: 121

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile His Tyr Thr Glu Gln Pro Ser Lys Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Gln Val Pro Ile Gly Val Lys Gly Gly Thr Gln Ser Cys
65                  70                  75                  80

Pro Leu Ser Ala Ile Phe Thr Thr
                85

<210> SEQ ID NO 122
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 122

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Tyr Tyr Phe Glu Asn Glu Asn Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly His Trp Ser
65                  70                  75                  80

Arg Pro Leu Ser Ala Ile Phe Thr Thr
                85

<210> SEQ ID NO 123
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 123

Leu Pro Ala Pro Lys Asn Leu Val Val Ser Arg Val Thr Glu Asp Ser
1               5                   10                  15

Ala Arg Leu Ser Trp Ala Leu Ser Ser Val His Ala Tyr Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Gln Tyr Val Asp
65                  70                  75                  80

Gly Phe Phe Lys Ser Asn Pro Leu Ser Ala Ile Phe Thr Thr
                85                  90

<210> SEQ ID NO 124
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 124

Leu Pro Ala Pro Lys Asn Leu Val Val Ser Arg Val Thr Glu Asp Ser
1               5                   10                  15

Ala Arg Leu Ser Trp Lys Phe Gly Glu Val Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gly Arg His Tyr Thr Val
65                  70                  75                  80

Tyr Asp Ser Asn Pro Leu Ser Ala Ile Phe Thr Thr
                85                  90

<210> SEQ ID NO 125
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 125

Leu Pro Ala Pro Lys Asn Leu Val Val Ser Arg Val Thr Glu Asp Ser
1               5                   10                  15

Ala Arg Leu Ser Trp Ala Phe Gln Trp His Ile Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gly Arg His Tyr Thr Val
65                  70                  75                  80

Tyr Asp Ser Asn Pro Leu Ser Ala Ile Phe Thr Thr
                85                  90

<210> SEQ ID NO 126
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 126

Leu Pro Ala Pro Lys Asn Leu Val Val Ser Arg Val Thr Glu Asp Ser
1               5                   10                  15

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Ala Pro
65                  70                  75                  80

Tyr Thr Val Tyr Asp Ser Asn Pro Leu Ser Ala Ile Phe Thr Thr
                85                  90                  95

<210> SEQ ID NO 127
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 127

Leu Pro Ala Pro Lys Asn Leu Val Val Ser Arg Val Thr Glu Asp Ser
1               5                   10                  15

Ala Arg Leu Ser Trp Arg Asp Leu Gln Tyr His Thr Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Gly Arg His Tyr Thr
65                  70                  75                  80

Val Tyr Asp Ser Asn Pro Leu Ser Ala Ile Phe Thr Thr
                85                  90

<210> SEQ ID NO 128
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 128

Leu Pro Ala Pro Lys Asn Leu Val Val Ser Arg Val Thr Glu Asp Ser
1               5                   10                  15

Ala Arg Leu Ser Trp Pro Asn His Ile Ser Ile Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Gly Arg Phe Tyr Thr Val
65                  70                  75                  80

Phe Asp Ser Asn Pro Leu Ser Ala Ile Phe Thr Thr
                85                  90

<210> SEQ ID NO 129
<211> LENGTH: 92
<212> TYPE: PRT
<213> ORGANISM: Artificial Sequence
<220> FEATURE:
<223> OTHER INFORMATION: CD137 Binding Centyrin

<400> SEQUENCE: 129

Leu Pro Ala Pro Lys Asn Leu Val Val Ser Arg Val Thr Glu Asp Ser
1               5                   10                  15

Ala Arg Leu Ser Trp Lys Phe His Ser Pro Thr Phe Asp Ser Phe Leu
            20                  25                  30

Ile Gln Tyr Gln Glu Ser Glu Lys Val Gly Glu Ala Ile Val Leu Thr

```
            35                  40                  45

Val Pro Gly Ser Glu Arg Ser Tyr Asp Leu Thr Gly Leu Lys Pro Gly
     50                  55                  60

Thr Glu Tyr Thr Val Ser Ile Tyr Gly Val Gly Arg His Tyr Thr Val
65                  70                  75                  80

Tyr Asp Ser Asn Pro Leu Ser Ala Ile Val Thr Thr
                85                  90
```

<210> SEQ ID NO 130
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 130

```
Leu Pro Ala Pro Lys Asn Leu Val Val Ser Arg Val Thr Glu Asp Ser
1               5                   10                  15

Ala Arg Leu Ser Trp Leu Glu Gln Glu Gln Phe Val Asn His Phe Asp
                20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
     50                  55                  60

Lys Pro Gly Thr Glu Tyr Thr Val Ser Ile Tyr Gly Val Gln Tyr Val
65                  70                  75                  80

Asp Gly Phe Phe Lys Ser Asn Pro Leu Ser Ala Ile Phe Thr Thr
                85                  90                  95
```

<210> SEQ ID NO 131
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 131

```
Leu Pro Ala Pro Lys Asn Leu Val Val Ser Arg Val Thr Glu Asp Ser
1               5                   10                  15

Ala Arg Leu Ser Trp Pro Leu Phe Ala Ser Asp Leu Asn Ile Phe Asp
                20                  25                  30

Ser Phe Leu Ile Gln Tyr Gln Glu Ser Glu Lys Val Gly Glu Ala Ile
            35                  40                  45

Val Leu Thr Val Pro Gly Ser Glu Arg Ser Tyr Asp Leu Thr Gly Leu
     50                  55                  60

Lys Pro Gly Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
                85                  90                  95
```

<210> SEQ ID NO 132
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 132

```
Leu Pro Ala Pro Lys Asn Leu Val Val Ser Arg Val Thr Glu Asp Ser
1               5                   10                  15
```

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
50                  55                  60

Lys Pro Gly Thr Glu Tyr Thr Val Ser Ile Tyr Gly Val Gly Arg His
65                  70                  75                  80

Tyr Thr Val Tyr Asp Ser Asn Pro Leu Ser Ala Ile Phe Thr Thr
            85                  90                  95

<210> SEQ ID NO 133
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 133

Leu Pro Ala Pro Lys Asn Leu Val Val Ser Arg Val Thr Glu Asp Ser
1               5                   10                  15

Ala Arg Leu Ser Trp Arg Ile Ser Asp Arg Leu Pro Leu Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Gly Arg His Tyr
65                  70                  75                  80

Thr Val Tyr Asp Ser Asn Pro Leu Ser Ala Ile Phe Thr Thr
            85                  90

<210> SEQ ID NO 134
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 134

Leu Pro Ala Pro Lys Asn Leu Val Val Ser Arg Val Thr Glu Asp Ser
1               5                   10                  15

Ala Arg Leu Ser Trp His Ala Thr Phe Gly Asp Pro Phe Asp Ser Phe
            20                  25                  30

Leu Ile Gln Tyr Gln Glu Ser Glu Lys Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Ser Ile Tyr Gly Val Gly Arg His Tyr Thr
65                  70                  75                  80

Val Tyr Asp Ser Asn Pro Leu Ser Ala Ile Phe Thr Thr
            85                  90

<210> SEQ ID NO 135
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 135

Leu Pro Ala Pro Lys Asn Leu Val Val Ser Arg Val Thr Glu Asp Ser
1               5                   10                  15

Ala Arg Leu Ser Trp Thr Asn Glu Gln Ile Thr Lys Tyr Gly Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Gly Arg Phe
65                  70                  75                  80

Tyr Thr Val Phe Asp Ser Asn Pro Leu Ser Ala Ile Phe Thr Thr
                85                  90                  95

<210> SEQ ID NO 136
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 136

Leu Pro Ala Pro Lys Asn Leu Val Val Ser Arg Val Thr Glu Asp Ser
1               5                   10                  15

Ala Arg Leu Ser Trp Ala Trp Asn Arg His Asp Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val His Trp Thr Val Leu Arg
65                  70                  75                  80

Pro Phe Ile Asp Ser Asn Pro Leu Ser Ala Ile Phe Thr Thr
                85                  90

<210> SEQ ID NO 137
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 137

Leu Pro Ala Pro Lys Asn Leu Val Val Ser Arg Val Thr Glu Asp Ser
1               5                   10                  15

Ala Arg Leu Ser Trp Pro Asp Glu Ser Arg Pro Val Arg Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Leu Arg Pro Trp
65                  70                  75                  80

Ile Tyr Ala Thr Asn Asp Ser Asn Pro Leu Ser Ala Ile Phe Thr Thr
                85                  90                  95

<210> SEQ ID NO 138

```
<211> LENGTH: 94
<212> TYPE: PRT
<213> ORGANISM: Artificial Sequence
<220> FEATURE:
<223> OTHER INFORMATION: CD137 Binding Centyrin

<400> SEQUENCE: 138

Leu Pro Ala Pro Lys Asn Leu Val Val Ser Arg Val Thr Glu Asp Ser
1               5                   10                  15

Ala Arg Leu Ser Trp Gly Ala Ile Thr Ala Leu Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Phe Pro Tyr Tyr Tyr
65                  70                  75                  80

Ala Thr Ala Asp Ser Asn Pro Leu Ser Ala Ile Phe Thr Thr
                85                  90

<210> SEQ ID NO 139
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 139

Leu Pro Ala Pro Lys Asn Leu Val Val Ser Arg Val Thr Glu Asp Ser
1               5                   10                  15

Ala Arg Leu Ser Trp Ala Gly His Tyr Arg Lys Ile Arg Asn Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Lys Phe Pro
65                  70                  75                  80

Tyr Tyr Tyr Ala Thr Ala Asp Ser Asn Pro Leu Ser Ala Ile Phe Thr
                85                  90                  95

Thr

<210> SEQ ID NO 140
<211> LENGTH: 97
<212> TYPE: PRT
<213> ORGANISM: Artificial Sequence
<220> FEATURE:
<223> OTHER INFORMATION: CD137 Binding Centyrin

<400> SEQUENCE: 140

Leu Pro Ala Pro Lys Asn Leu Val Val Ser Arg Val Thr Glu Asp Ser
1               5                   10                  15

Ala Arg Leu Ser Trp Ala Gly His Tyr Arg Lys Ile Arg Asn Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Ala Glu His
```

```
65                  70                  75                  80
Trp Tyr Tyr Ala Thr Gln Asp Ser Asn Pro Leu Ser Ala Ile Phe Thr
                85                  90                  95

Thr

<210> SEQ ID NO 141
<211> LENGTH: 93
<212> TYPE: PRT
<213> ORGANISM: Artificial Sequence
<220> FEATURE:
<223> OTHER INFORMATION: CD137 Binding Centyrin

<400> SEQUENCE: 141

Leu Pro Ala Pro Lys Asn Leu Val Val Ser Arg Val Thr Glu Asp Ser
1               5                   10                  15

Ala Arg Leu Ser Trp Ala Gln Ser Asn Gln Phe Asp Ser Phe Leu
                20                  25                  30

Ile Gln Tyr Gln Glu Ser Glu Lys Val Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Thr Val Ser Ile Tyr Gly Val Val Trp Gln Asn Trp Val
65                  70                  75                  80

Ala Tyr Asn Ser Asn Pro Leu Ser Ala Ile Phe Thr Thr
                85                  90

<210> SEQ ID NO 142
<211> LENGTH: 95
<212> TYPE: PRT
<213> ORGANISM: Artificial Sequence
<220> FEATURE:
<223> OTHER INFORMATION: CD137 Binding Centyrin

<400> SEQUENCE: 142

Leu Pro Ala Pro Lys Asn Leu Val Val Ser Arg Val Thr Glu Asp Ser
1               5                   10                  15

Ala Arg Leu Ser Trp Asp Asp Gln Phe Glu Asp Trp Phe Asp Ser Phe
                20                  25                  30

Leu Ile Gln Tyr Gln Glu Ser Glu Gln Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val His Thr Arg Asp Trp
65                  70                  75                  80

Thr Ala Trp Asn Ala Ser Asn Pro Leu Ser Ala Ile Phe Thr Thr
                85                  90                  95

<210> SEQ ID NO 143
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 143

Leu Pro Ala Pro Lys Asn Leu Val Val Ser Arg Val Thr Glu Asp Ser
1               5                   10                  15

Ala Arg Leu Ser Trp Lys Gln Val Thr Val Ala Pro Glu Phe Asp Ser
                20                  25                  30
```

```
Phe Leu Ile Gln Tyr Gln Glu Ser Glu Lys Val Gly Glu Ala Ile Val
             35                  40                  45
Leu Thr Val Pro Gly Ser Glu Arg Ser Tyr Asp Leu Thr Gly Leu Lys
 50                  55                  60
Pro Gly Thr Glu Tyr Thr Val Ser Ile Tyr Gly Val Lys Phe Pro Tyr
 65                  70                  75                  80
Tyr Tyr Ala Thr Ala Asp Ser Asn Pro Leu Ser Ala Ile Phe Thr Thr
                 85                  90                  95
```

<210> SEQ ID NO 144
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 144

```
Leu Pro Ala Pro Lys Asn Leu Val Val Ser Arg Val Thr Glu Asp Ser
 1               5                  10                  15
Ala Arg Leu Ser Trp Pro Asp Glu Ser Arg Pro Val Arg Phe Asp Ser
                 20                  25                  30
Phe Leu Ile Gln Tyr Gln Glu Ser Glu Lys Val Gly Glu Ala Ile Val
             35                  40                  45
Leu Thr Val Pro Gly Ser Glu Arg Ser Tyr Asp Leu Thr Gly Leu Lys
 50                  55                  60
Pro Gly Thr Glu Tyr Thr Val Ser Ile Tyr Gly Val His Thr Arg Asp
 65                  70                  75                  80
Trp Thr Ala Trp Asn Ala Ser Asn Pro Leu Ser Ala Ile Phe Thr Thr
                 85                  90                  95
```

<210> SEQ ID NO 145
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 145

```
Leu Pro Ala Pro Lys Asn Leu Val Val Ser Arg Val Thr Glu Asp Ser
 1               5                  10                  15
Ala Arg Leu Ser Trp Asn Arg Leu Asp Ser Glu Trp Val Ala Phe Asp
                 20                  25                  30
Ser Phe Leu Ile Gln Tyr Gln Glu Ser Glu Lys Val Gly Glu Ala Ile
             35                  40                  45
Val Leu Thr Val Pro Gly Ser Glu Arg Ser Tyr Asp Leu Thr Gly Leu
 50                  55                  60
Lys Pro Gly Thr Glu Tyr Thr Val Ser Ile Tyr Gly Val Val Phe Arg
 65                  70                  75                  80
Pro Trp Leu Ala Tyr Asn Ser Asn Pro Leu Ser Ala Ile Phe Thr Thr
                 85                  90                  95
```

<210> SEQ ID NO 146
<211> LENGTH: 96
<212> TYPE: PRT
<213> ORGANISM: Artificial Sequence
<220> FEATURE:
<223> OTHER INFORMATION: CD137 Binding Centyrin

<400> SEQUENCE: 146

```
Leu Pro Ala Pro Lys Asn Leu Val Val Ser Arg Val Thr Glu Asp Ser
```

```
                1               5                  10                 15
Ala Arg Leu Ser Trp Pro Asp Glu Ser Arg Pro Val Arg Phe Asp Ser
                 20                 25                 30

Phe Leu Ile Gln Tyr Gln Glu Ser Glu Lys Val Gly Glu Ala Ile Val
                 35                 40                 45

Leu Thr Val Pro Gly Ser Glu Arg Ser Tyr Asp Leu Thr Gly Leu Lys
                 50                 55                 60

Pro Gly Thr Glu Tyr Thr Val Ser Ile Tyr Gly Val Val Gly Gln Trp
 65                 70                 75                 80

Lys Tyr Ala Thr Ala Asp Ser Asn Pro Leu Ser Ala Ile Phe Thr Thr
                 85                 90                 95

<210> SEQ ID NO 147
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 147

Leu Pro Ala Pro Lys Asn Leu Val Val Ser Arg Val Thr Glu Asp Ser
 1               5                  10                 15

Ala Arg Leu Ser Trp Thr Ala Pro Asp Ala Ala Phe Asp Ser Phe Asp
                 20                 25                 30

Ile Tyr Tyr Phe Glu His Pro Val Gly Gly Glu Ala Ile Val Leu Thr
                 35                 40                 45

Val Pro Gly Ser Glu Arg Ser Tyr Asp Leu Thr Gly Leu Lys Pro Gly
                 50                 55                 60

Thr Glu Tyr Leu Val Thr Ile Tyr Gly Val Lys Gly His Phe Ser
 65                 70                 75                 80

Gly Pro Leu Ser Ala Ile Phe Thr Thr
                 85

<210> SEQ ID NO 148
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 148

Leu Pro Ala Pro Lys Asn Leu Val Val Ser Arg Val Thr Glu Asp Ser
 1               5                  10                 15

Ala Arg Leu Ser Trp Thr Ala Pro Asp Ala Ala Phe Asp Ser Phe Ala
                 20                 25                 30

Ile Gln Tyr Gln Glu Tyr Val Ala His Gly Glu Ala Ile Val Leu Thr
                 35                 40                 45

Val Pro Gly Ser Glu Arg Ser Tyr Asp Leu Thr Gly Leu Lys Pro Gly
                 50                 55                 60

Thr Glu Tyr His Val Arg Ile Ser Gly Val Lys Gly Gly Gly Val Ser
 65                 70                 75                 80

Trp Pro Leu Ser Ala Ile Phe Thr Thr
                 85

<210> SEQ ID NO 149
<211> LENGTH: 89
<212> TYPE: PRT
<213> ORGANISM: Artificial Sequence
<220> FEATURE:
```

<223> OTHER INFORMATION: CD137 Binding Centyrin

<400> SEQUENCE: 149

Leu Pro Ala Pro Lys Asn Leu Val Val Ser Arg Val Thr Glu Asp Ser
1               5                   10                  15

Ala Arg Leu Ser Trp Thr Thr Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Tyr Leu Ser
65                  70                  75                  80

Lys Pro Leu Ser Ala Ile Phe Thr Thr
                85

<210> SEQ ID NO 150
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 150

Leu Pro Ala Pro Lys Asn Leu Ile Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Lys Glu Leu Arg Ala Glu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Ser Val Ser
65                  70                  75                  80

Ile Pro Leu Ser Ala Ile Phe Thr Thr
                85

<210> SEQ ID NO 151
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 151

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Leu Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Tyr Leu Ser
65                  70                  75                  80

Met Pro Leu Ser Ala Ile Phe Thr Thr
                85

```
<210> SEQ ID NO 152
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 152

Leu Pro Ala Pro Lys Asn Leu Val Val Ser His Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Tyr Leu Ser
65                  70                  75                  80

Met Pro Leu Ser Ala Ile Phe Thr Thr
                85

<210> SEQ ID NO 153
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 153

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Gln Tyr Gln Glu Tyr Val Ala His Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Arg Ile Ser Gly Val Lys Gly Gly Gly Val Ser
65                  70                  75                  80

Trp Pro Leu Ser Ala Ile Val Thr Thr
                85

<210> SEQ ID NO 154
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 154

Leu Leu Ala Pro Lys Asn Leu Val Val Ser Arg Val Thr Glu Asp Ser
1               5                   10                  15

Ala Arg Leu Ser Trp Ile Ala Pro Asp Ala Ala Phe Asp Ser Phe Glu
                20                  25                  30

Ile Tyr Tyr Lys Glu Leu Arg Ala Glu Gly Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Ser Val Ser
65                  70                  75                  80
```

```
Ile Pro Leu Ser Ala Ile Phe Thr Thr
                85

<210> SEQ ID NO 155
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 155

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Ile Trp Ser
65                  70                  75                  80

Val Pro Leu Ser Ala Ile Phe Thr Thr
                85

<210> SEQ ID NO 156
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 156

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Thr Tyr Ser
65                  70                  75                  80

Leu Pro Leu Ser Ala Ile Phe Thr Thr
                85

<210> SEQ ID NO 157
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 157

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45
```

```
Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Glu Leu Ser
65                  70                  75                  80

Lys Pro Leu Ser Ala Ile Ser Thr Thr
                85
```

<210> SEQ ID NO 158
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 158

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Thr Tyr Ser
65                  70                  75                  80

Pro Pro Leu Ser Ala Ile Phe Thr Thr
                85
```

<210> SEQ ID NO 159
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 159

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Gly Glu His Trp Lys Leu Gly Glu Ala Ile Val Leu Thr
            35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Met Ser Ser
65                  70                  75                  80

Asn Pro Leu Ser Ala Ile Phe Thr Thr
                85
```

<210> SEQ ID NO 160
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 160

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
```

```
            20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Ser Val Ser
65                  70                  75                  80

Ile Pro Leu Ser Ala Ile Phe Thr Thr
                85

<210> SEQ ID NO 161
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 161

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Phe Trp Ser
65                  70                  75                  80

Gln Pro Leu Ser Ala Ile Phe Thr Thr
                85

<210> SEQ ID NO 162
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 162

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Ile Tyr Gln Glu Tyr Val Lys Ser Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Arg Ile Gly Gly Val Lys Gly Gly Leu Leu Ser
65                  70                  75                  80

Leu Pro Leu Ser Ala Ile Phe Thr Thr
                85

<210> SEQ ID NO 163
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 163
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Glu Leu Ser
65                  70                  75                  80

Lys Pro Leu Ser Ala Ile Phe Thr Thr
                85

<210> SEQ ID NO 164
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 164

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Gln Tyr Gln Glu Tyr Val Ala His Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Arg Ile Ser Gly Val Lys Gly Gly Val Ser
65                  70                  75                  80

Trp Pro Leu Ser Ala Ile Ser Thr Thr
                85

<210> SEQ ID NO 165
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 165

Leu Pro Ala Pro Lys Asn Leu Val Val Ser Arg Val Thr Glu Asp Ser
1               5                   10                  15

Ala His Leu Ser Trp Thr Ala Pro Asp Ala Ala Phe Asp Ser Phe Asp
                20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Tyr Leu Ser
65                  70                  75                  80

Met Pro Leu Ser Ala Ile Phe Thr Thr
                85

<210> SEQ ID NO 166
<211> LENGTH: 89
<212> TYPE: PRT

<213> ORGANISM: Artificial Sequence
<220> FEATURE:
<223> OTHER INFORMATION: CD137 Binding Centyrin

<400> SEQUENCE: 166

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile Tyr Tyr Gly Glu His Tyr Asn Leu Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Phe Trp Ser
65                  70                  75                  80

Thr Pro Leu Ser Ala Ile Phe Thr Thr
                85

<210> SEQ ID NO 167
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 167

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Tyr Leu Ser
65                  70                  75                  80

Met Pro Leu Ser Ala Ile Phe Thr Thr
                85

<210> SEQ ID NO 168
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 168

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu Gln Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Tyr Leu Ser
65                  70                  75                  80

Met Pro Leu Ser Ala Ile Phe Thr Thr
                85

<210> SEQ ID NO 169
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 169

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Asn Phe Ser
65                  70                  75                  80

Phe Pro Leu Ser Ala Ile Phe Thr Thr
                85

<210> SEQ ID NO 170
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 170

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Tyr Leu Ser
65                  70                  75                  80

Met Pro Leu Ser Ala Ile Phe Thr Thr
                85

<210> SEQ ID NO 171
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 171

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Phe Glu His Pro Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly Asn Gly Ser
65                  70                  75                  80

Ser Pro Leu Ser Ala Ile Phe Thr Thr
                85

<210> SEQ ID NO 172
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 172

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Phe Glu His Pro Val Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Ala Ile Tyr Gly Val Lys Gly Gly Val Phe Ser
65                  70                  75                  80

His Pro Leu Ser Ala Ile Phe Thr Thr
                85

<210> SEQ ID NO 173
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 173

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
                20                  25                  30

Ile Ser Tyr Leu Glu Asp Val Tyr Tyr Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr His Val Gly Ile His Gly Val Lys Gly Gly Ile Asp Ser
65                  70                  75                  80

Phe Pro Leu Ser Ala Ile Phe Thr Thr
                85

<210> SEQ ID NO 174
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 174

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Leu Glu Val Arg Asn Arg Gly Glu Ala Ile Val Leu Thr

```
                 35                  40                  45

Val Pro Gly Ser Glu Arg Ser Tyr Asp Leu Thr Gly Leu Lys Pro Gly
         50                  55                  60

Thr Glu Tyr His Val Gly Ile Ala Gly Val Lys Gly Gly Phe His Ser
 65                  70                  75                  80

Phe Pro Leu Ser Ala Ile Phe Thr Thr
                 85

<210> SEQ ID NO 175
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 175

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
             20                  25                  30

Ile Gln Tyr Trp Glu Gly Trp Glu Trp Gly Glu Ala Ile Val Leu Thr
         35                  40                  45

Val Pro Gly Ser Glu Arg Ser Tyr Asp Leu Thr Gly Leu Lys Pro Gly
         50                  55                  60

Thr Glu Tyr Leu Val Thr Ile Tyr Gly Val Lys Gly Gly His Trp Ser
 65                  70                  75                  80

Arg Pro Leu Ser Ala Ile Phe Thr Thr
                 85

<210> SEQ ID NO 176
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 176

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Glu
             20                  25                  30

Ile Tyr Tyr Ile Glu Pro Ile Ala Pro Gly Glu Ala Ile Val Leu Thr
         35                  40                  45

Val Pro Gly Ser Glu Arg Ser Tyr Asp Leu Thr Gly Leu Lys Pro Gly
         50                  55                  60

Thr Glu Tyr Trp Val Thr Ile Tyr Gly Val Lys Gly Cys Asp Trp Ser
 65                  70                  75                  80

Asp Pro Leu Ser Ala Ile Phe Thr Thr
                 85

<210> SEQ ID NO 177
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 177

Leu Pro Ala Pro Lys Asn Leu Val Val Ser Arg Val Thr Glu Asp Ser
 1               5                  10                  15
```

```
Ala Arg Leu Ser Trp Thr Ala Pro Asp Ala Ala Phe Asp Ser Phe Glu
            20                  25                  30

Ile Tyr Tyr Phe Glu Asn Glu Asn Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 178
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 178

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile Tyr Tyr Leu Glu Gln Tyr Ser Arg Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 179
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 179

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Tyr Tyr Phe Glu Trp Val Val Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 180
<211> LENGTH: 89
<212> TYPE: PRT
<213> ORGANISM: Artificial Sequence
<220> FEATURE:
<223> OTHER INFORMATION: CD137 Binding Centyrin
```

<400> SEQUENCE: 180

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
                20                  25                  30

Ile Gln Tyr Leu Glu Asp Val Thr Asn Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Arg Val Pro Ile Ala Gly Val Lys Gly Arg Asp Ser
65                  70                  75                  80

Gln Pro Leu Ser Ala Ile Phe Thr Thr
                85

<210> SEQ ID NO 181
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 181

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Arg Tyr Ile Glu Asp Val Asp Phe Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 182
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 182

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Ala Glu Tyr Phe Lys Asn Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Asp Trp Ser
65                  70                  75                  80

Asp Pro Leu Ser Ala Ile Ser Thr Thr
                85

<210> SEQ ID NO 183

```
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 183

Leu Pro Ala Pro Lys Asn Leu Val Val Ser Arg Val Thr Glu Asp Ser
1               5                   10                  15
Ala Arg Leu Ser Trp Thr Ala Pro Asp Ala Ala Phe Asp Ser Phe Ile
            20                  25                  30
Ile Arg Tyr Leu Glu Asp Ile Ser Tyr Gly Glu Ala Ile Val Leu Thr
        35                  40                  45
Val Pro Gly Ser Glu Arg Ser Tyr Asp Leu Thr Gly Leu Lys Pro Gly
    50                  55                  60
Thr Glu Tyr His Val Gly Ile Glu Gly Val Lys Gly Gly Asn Val Ser
65                  70                  75                  80
Trp Pro Leu Ser Ala Ile Phe Thr Thr
                85

<210> SEQ ID NO 184
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 184

Leu Pro Ala Pro Lys Asn Leu Val Val Ser Arg Val Thr Glu Asp Ser
1               5                   10                  15
Ala Arg Leu Ser Trp Thr Thr Pro Asp Ala Ala Phe Asp Ser Phe His
            20                  25                  30
Ile His Tyr Leu Glu Gly Glu Trp Gly Gly Glu Ala Ile Val Leu Thr
        35                  40                  45
Val Pro Gly Ser Glu Arg Ser Tyr Asp Leu Thr Gly Leu Lys Pro Gly
    50                  55                  60
Thr Glu Tyr Leu Val Thr Ile Tyr Gly Val Lys Gly Cys Asp Trp Ser
65                  70                  75                  80
Asp Pro Leu Ser Ala Ile Phe Thr Thr
                85

<210> SEQ ID NO 185
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 185

Leu Pro Ala Pro Lys Asn Leu Val Val Ser Arg Val Thr Glu Asp Ser
1               5                   10                  15
Ala Arg Leu Ser Trp Thr Ala Pro Asp Ala Ala Phe Asp Ser Phe Asp
            20                  25                  30
Ile Asn Tyr Phe Glu Asn Glu Leu Gly Gly Glu Ala Ile Val Leu Thr
        35                  40                  45
Val Pro Gly Ser Glu Arg Ser Tyr Asp Leu Thr Gly Leu Lys Pro Gly
    50                  55                  60
Thr Glu Tyr Leu Val Thr Ile Tyr Gly Val Lys Gly Cys Asp Trp Ser
65                  70                  75                  80
```

Asp Pro Leu Ser Ala Ile Phe Thr Thr
                85

<210> SEQ ID NO 186
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 186

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Tyr Tyr Phe Glu Asn Glu Asn Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Gly His Trp Ser
65                  70                  75                  80

Arg Pro Leu Ser Ala Ile Phe Thr Thr
                85

<210> SEQ ID NO 187
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 187

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Tyr Tyr Phe Glu Asn Glu Asn Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85

<210> SEQ ID NO 188
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 188

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
            20                  25                  30

Ile Tyr Tyr Phe Glu Asn Glu Asn Gly Gly Glu Ala Ile Val Leu Thr
        35                  40                  45

Val Pro Gly Ser Glu Arg Ser Tyr Asp Leu Thr Gly Leu Lys Pro Asp

```
                   50                  55                  60
Thr Glu Tyr Leu Val Thr Ile Tyr Gly Val Lys Gly Gly His Trp Ser
 65                  70                  75                  80

Arg Pro Leu Ser Ala Ile Phe Thr Thr
                 85
```

<210> SEQ ID NO 189
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 189

```
Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Glu
                 20                  25                  30

Ile Tyr Tyr Phe Glu Asn Glu Leu Gly Gly Glu Ala Ile Val Leu Thr
             35                  40                  45

Val Pro Gly Ser Glu Arg Ser Tyr Asp Leu Thr Gly Leu Lys Pro Gly
         50                  55                  60

Thr Glu Tyr Leu Val Thr Ile Tyr Gly Val Lys Gly Gly Asp Trp Ser
 65                  70                  75                  80

Asp Pro Leu Ser Ala Ile Phe Thr Thr
                 85
```

<210> SEQ ID NO 190
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 190

```
Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe His
                 20                  25                  30

Ile His Tyr Leu Glu Gly Glu Trp Gly Gly Glu Ala Ile Val Leu Thr
             35                  40                  45

Val Pro Gly Ser Glu Arg Ser Tyr Asp Leu Thr Gly Leu Lys Pro Gly
         50                  55                  60

Thr Glu Tyr Leu Val Thr Ile Tyr Gly Val Lys Gly Cys Asp Trp Ser
 65                  70                  75                  80

Asp Pro Leu Ser Ala Ile Phe Thr Thr
                 85
```

<210> SEQ ID NO 191
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 191

```
Leu Pro Ala Pro Lys Asn Leu Val Val Ser Arg Val Thr Glu Asp Ser
  1               5                  10                  15

Ala Arg Leu Ser Trp Thr Ala Pro Asp Ala Ala Phe Asp Ser Phe Glu
                 20                  25                  30
```

```
Ile Tyr Tyr Phe Glu Asn Glu Leu Gly Gly Glu Ala Ile Val Leu Thr
            35                  40                  45

Val Pro Gly Ser Glu Arg Ser Tyr Asp Leu Thr Gly Leu Lys Pro Gly
     50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85
```

<210> SEQ ID NO 192
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 192

```
Leu Pro Ala Pro Lys Asn Leu Phe Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Tyr Tyr Arg Glu Gln Trp Trp Asp Gly Glu Ala Ile Val Leu Thr
            35                  40                  45

Val Pro Gly Ser Glu Arg Ser Tyr Asp Leu Thr Gly Leu Lys Pro Gly
     50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85
```

<210> SEQ ID NO 193
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 193

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Asn Tyr Phe Glu Gln Pro Lys Gly Gly Glu Ala Ile Val Leu Thr
            35                  40                  45

Val Pro Gly Ser Glu Arg Ser Tyr Asp Leu Thr Gly Leu Lys Pro Gly
     50                  55                  60

Thr Glu Tyr Leu Val Thr Ile Tyr Gly Val Lys Gly Cys Asp Trp Ser
65                  70                  75                  80

Asp Pro Leu Ser Ala Ile Phe Thr Thr
                85
```

<210> SEQ ID NO 194
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 194

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Asp Glu Leu Arg Asn Pro Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Ala Val Thr Ile Tyr Gly Val Lys Gly Gly Arg Tyr Ser
65                  70                  75                  80

Pro Pro Leu Ser Ala Ile Phe Thr Thr
                85
```

<210> SEQ ID NO 195
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 195

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Phe Tyr His Glu Phe Ala Asn Pro Gly Glu Ala Ile Asp Leu Pro
        35                  40                  45

Val Pro Gly Ser Glu Arg Ser Tyr Asp Leu Thr Gly Leu Lys Pro Gly
    50                  55                  60

Thr Glu Tyr Asp Val Arg Ile Tyr Gly Val Lys Gly Gly Thr Ala Ser
65                  70                  75                  80

Ile Pro Leu Asp Ala Glu Phe Thr Thr
                85
```

<210> SEQ ID NO 196
<211> LENGTH: 90
<212> TYPE: PRT
<213> ORGANISM: Artificial Sequence
<220> FEATURE:
<223> OTHER INFORMATION: CD137 Binding Centyrin

<400> SEQUENCE: 196

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Val Glu Trp Thr Ala Asn Gly Glu Ala Ile Val Leu Ile
        35                  40                  45

Val Pro Gly Ser Glu Arg Ser Tyr Asp Leu Thr Gly Leu Lys Pro Gly
    50                  55                  60

Thr Glu Tyr Val Val Arg Ile Arg Gly Val Lys Gly Gly Asp Ser
65                  70                  75                  80

Ser Phe Pro Leu Arg Ala Asp Phe Thr Thr
                85                  90
```

<210> SEQ ID NO 197
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 197

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Ser Tyr Thr Glu Ser Ile Arg Gln Gly Glu Ala Ile Trp Leu Trp
            35                  40                  45

Val Pro Gly Ser Glu Arg Ser Tyr Asp Leu Thr Gly Leu Lys Pro Gly
        50                  55                  60

Thr Glu Tyr Glu Val Thr Ile Gly Gly Val Lys Gly Ile Arg Ser
65                  70                  75                  80

Tyr Pro Leu Trp Ala Trp Phe Thr Thr
                85

<210> SEQ ID NO 198
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 198

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Asp Tyr Trp Glu Val Glu Ser Glu Gly Glu Ala Ile Val Leu Phe
            35                  40                  45

Val Pro Gly Ser Glu Arg Ser Tyr Asp Leu Thr Gly Leu Lys Pro Gly
        50                  55                  60

Thr Glu Tyr His Val His Ile Val Gly Val Lys Gly Gly Thr Pro Ser
65                  70                  75                  80

Tyr Pro Leu Trp Ala Asp Phe Thr Thr
                85

<210> SEQ ID NO 199
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 199

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Pro Tyr Val Glu Tyr Tyr Pro Ser Gly Glu Ala Ile Val Leu Asn
            35                  40                  45

Val Pro Gly Ser Glu Arg Ser Tyr Asp Leu Thr Gly Leu Lys Pro Gly
        50                  55                  60

Thr Glu Tyr Gly Val Thr Ile Trp Gly Ile Lys Gly Gly Asn Glu Ser
65                  70                  75                  80

Val Pro Leu Thr Ala Arg Phe Thr Thr
                85

<210> SEQ ID NO 200
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 200

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Phe Tyr His Glu Phe Ala Asn Ser Gly Glu Ala Ile Asp Leu Pro
        35                  40                  45

Val Pro Gly Ser Glu Arg Ser Tyr Asp Leu Thr Gly Leu Lys Pro Gly
    50                  55                  60

Thr Glu Tyr Asp Val Arg Ile Tyr Gly Val Lys Gly Gly Thr Ala Ser
65                  70                  75                  80

Ile Pro Leu Asp Ala Glu Phe Thr Thr
                85

<210> SEQ ID NO 201
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 201

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Pro Tyr Ile Glu Val Glu Thr Ile Gly Glu Ala Ile Trp Leu His
        35                  40                  45

Val Pro Gly Ser Glu Arg Ser Tyr Asp Leu Thr Gly Leu Lys Pro Gly
    50                  55                  60

Thr Glu Tyr Ser Val Gly Ile Asn Gly Val Lys Gly Gly His Thr Ser
65                  70                  75                  80

Asn Pro Leu Ser Ala Arg Phe Thr Thr
                85

<210> SEQ ID NO 202
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 202

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Leu Glu Pro Trp Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Trp Val Thr Ile Tyr Gly Val Lys Val Cys Leu Gly Ser 65                  70                  75                  80

Asn Pro Leu Ser Ala Ile Phe Thr Thr
                85

<210> SEQ ID NO 203
<211> LENGTH: 88
<212> TYPE: PRT
<213> ORGANISM: Artificial Sequence
<220> FEATURE:
<223> OTHER INFORMATION: CD137 Binding Centyrin

<400> SEQUENCE: 203

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Leu Glu Gly Gly Arg Gly Glu Ala Ile Val Leu Thr Val
        35                  40                  45

Pro Gly Ser Glu Arg Ser Tyr Asp Leu Thr Gly Leu Lys Pro Gly Thr
    50                  55                  60

Glu Tyr Leu Val Thr Ile Tyr Gly Val Lys Cys Gly Trp Ala Ser Asn
65                  70                  75                  80

Pro Leu Ser Ala Ile Phe Thr Thr
                85

<210> SEQ ID NO 204
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 204

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Gly Tyr Ser
65                  70                  75                  80

Ala Pro Leu Ser Ala Ile Val Thr Thr
                85

<210> SEQ ID NO 205
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 205

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

```
Val Pro Gly Ser Glu Arg Ser Tyr Asp Leu Thr Gly Leu Lys Pro Gly
     50                  55                  60

Thr Glu Tyr Leu Val Ser Ile Tyr Gly Val Lys Cys Gly Tyr Ser
 65                  70                  75                  80

Asp Pro Leu Ser Ala Ile Phe Thr Thr
                 85

<210> SEQ ID NO 206
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 206

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
             35                  40                  45

Val Pro Gly Ser Glu Arg Ser Tyr Asp Leu Thr Gly Leu Lys Pro Gly
     50                  55                  60

Thr Glu Tyr Leu Val Thr Ile Tyr Gly Val Lys Val Cys Asn Ala Ser
 65                  70                  75                  80

Thr Pro Leu Ser Ala Ile Phe Thr Thr
                 85

<210> SEQ ID NO 207
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 207

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Glu
                20                  25                  30

Ile Tyr Tyr Phe Glu Leu Arg Leu Gly Gly Glu Ala Ile Val Leu Thr
             35                  40                  45

Val Pro Gly Ser Glu Arg Ser Tyr Asp Leu Thr Gly Leu Lys Pro Gly
     50                  55                  60

Thr Glu Tyr Leu Val Thr Ile Tyr Gly Val Lys Gly Cys Gly Tyr Ser
 65                  70                  75                  80

Asp Pro Leu Ser Ala Ile Phe Thr Thr
                 85

<210> SEQ ID NO 208
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 208

Leu Pro Ala Pro Lys Asn Leu Val Val Ser Arg Val Thr Glu Asp Ser
 1               5                  10                  15
```

Ala Arg Leu Ser Trp Thr Ala Pro Asp Ala Ala Phe Asp Ser Phe Glu
            20                  25                  30

Ile Tyr Tyr Phe Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Leu Val Ser Ile Tyr Gly Val Lys Gly Cys Gly Tyr Ser
65                  70                  75                  80

Asp Pro Leu Ser Ala Ile Phe Thr Thr
                85

<210> SEQ ID NO 209
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 209

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Leu Glu Leu Asp Ser Asp Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Ile Val Thr Ile Tyr Gly Val Lys Val Cys Thr Gly Ser
65                  70                  75                  80

Arg Pro Leu Ser Ala Ile Phe Thr Thr
                85

<210> SEQ ID NO 210
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 210

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Phe Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
 50                  55                  60

Thr Glu Tyr Leu Val Thr Ile Tyr Gly Val Lys Gly Gly Gly Tyr Ser
65                  70                  75                  80

Thr Pro Leu Ser Ala Ile Phe Thr Thr
                85

<210> SEQ ID NO 211
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 211

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Val Cys Glu Gln Ser
65                  70                  75                  80

Tyr Pro Leu Ser Ala Ile Phe Thr Thr
                85

<210> SEQ ID NO 212
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 212

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Leu Glu Ser Gly Arg Asp Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Ser Ile Tyr Gly Val Lys Gly Cys Gly Tyr Ser
65                  70                  75                  80

Asp Pro Leu Ser Ala Ile Phe Thr Thr
                85

<210> SEQ ID NO 213
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 213

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Leu Glu Trp Cys Ser Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Ala Ala Ser
65                  70                  75                  80

Asp Pro Leu Ser Ala Ile Phe Thr Thr
                85

```
<210> SEQ ID NO 214
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 214

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Phe Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Ala Tyr Ser
65                  70                  75                  80

Asn Pro Leu Ser Ala Ile Phe Thr Thr
                85

<210> SEQ ID NO 215
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 215

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
            20                  25                  30

Ile Tyr Tyr Ala Glu Phe Gly Tyr Tyr Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Leu Val Thr Ile Tyr Gly Val Lys Gly Cys Ala Ala Ser
65                  70                  75                  80

Asp Pro Leu Ser Ala Ile Phe Thr Thr
                85

<210> SEQ ID NO 216
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 216

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Tyr Tyr Tyr Glu Leu Arg Leu Gly Gly Glu Ala Ile Val Leu Thr
        35                  40                  45

Val Pro Gly Ser Glu Arg Ser Tyr Asp Leu Thr Gly Leu Lys Pro Gly
    50                  55                  60
```

Thr Glu Tyr Leu Val Thr Ile Tyr Gly Val Lys Gly Gly Asp Tyr Ser
65                  70                  75                  80

Pro Pro Leu Ser Ala Ile Phe Thr Thr
                85

<210> SEQ ID NO 217
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 217

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
                35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Gly Tyr Tyr Ser
65                  70                  75                  80

Gly Pro Leu Ser Ala Ile Phe Thr Thr
                85

<210> SEQ ID NO 218
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 218

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
                35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Val Cys Tyr Tyr Ser
65                  70                  75                  80

Thr Pro Leu Ser Ala Ile Phe Thr Thr
                85

<210> SEQ ID NO 219
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 219

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Phe Glu Leu Arg Leu Gly Gly Glu Ala Ile Val Leu Thr
                35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Asp Tyr Ser
65                  70                  75                  80

Pro Pro Leu Ser Ala Ile Ser Thr Thr
                85

<210> SEQ ID NO 220
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 220

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Phe Glu Leu Arg Leu Gly Gly Glu Ala Ile Val Leu Thr
                35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Asp Tyr Ser
65                  70                  75                  80

Pro Pro Leu Ser Ala Ile Phe Thr Thr
                85

<210> SEQ ID NO 221
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 221

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
                35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Gly Cys Ala Ala Ser
65                  70                  75                  80

Asp Pro Leu Ser Ala Ile Phe Thr Thr
                85

<210> SEQ ID NO 222
<211> LENGTH: 89
<212> TYPE: PRT
<213> ORGANISM: Artificial Sequence
<220> FEATURE:
<223> OTHER INFORMATION: CD137 Binding Centyrin

```
<400> SEQUENCE: 222

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Val Cys Glu Gln Ser
65                  70                  75                  80

Tyr Pro Leu Ser Ala Ile Ser Thr Thr
                85

<210> SEQ ID NO 223
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 223

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
                20                  25                  30

Ile Tyr Tyr Tyr Glu Leu Arg Leu Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Leu Val Thr Ile Tyr Gly Val Lys Val Cys Leu Gly Ser
65                  70                  75                  80

Asn Pro Leu Ser Ala Ile Phe Thr Thr
                85

<210> SEQ ID NO 224
<211> LENGTH: 89
<212> TYPE: PRT
<213> ORGANISM: Artificial Sequence
<220> FEATURE:
<223> OTHER INFORMATION: CD137 Binding Centyrin

<400> SEQUENCE: 224

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Glu
                20                  25                  30

Ile Tyr Tyr Arg Glu Pro His Tyr Gly Gly Glu Ala Ile Val Leu Thr
            35                  40                  45

Val Pro Gly Ser Glu Arg Ser Tyr Asp Leu Thr Gly Leu Lys Pro Gly
        50                  55                  60

Thr Glu Tyr Trp Val Thr Ile Tyr Gly Val Lys Val Cys Leu Gly Ser
65                  70                  75                  80

Asn Pro Leu Ser Ala Ile Phe Thr Thr
                85
```